US009326698B2

(12) United States Patent
Blanco et al.

(10) Patent No.: US 9,326,698 B2
(45) Date of Patent: May 3, 2016

(54) METHOD FOR AUTOMATIC, UNSUPERVISED CLASSIFICATION OF HIGH-FREQUENCY OSCILLATIONS IN PHYSIOLOGICAL RECORDINGS

(75) Inventors: Justin Blanco, Annapolis, MD (US); Brian Litt, Bala Cynwyd, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 1112 days.

(21) Appl. No.: 13/385,413

(22) Filed: Feb. 17, 2012

(65) Prior Publication Data
US 2012/0245481 A1    Sep. 27, 2012

Related U.S. Application Data

(60) Provisional application No. 61/444,560, filed on Feb. 18, 2011.

(51) Int. Cl.
*A61B 5/04*     (2006.01)
*A61B 5/0476*   (2006.01)
*A61B 5/048*    (2006.01)
*A61B 5/00*     (2006.01)

(52) U.S. Cl.
CPC .............. *A61B 5/048* (2013.01); *A61B 5/4094* (2013.01); *A61B 5/7264* (2013.01); *A61B 5/0476* (2013.01); *A61B 5/7203* (2013.01); *A61B 5/7267* (2013.01); *A61B 5/7275* (2013.01)

(58) Field of Classification Search
CPC .... A61B 5/048; A61B 5/4094; A61B 5/7203; A61B 5/7264; A61B 5/7267; A61B 5/7275; A61B 5/7282; A61B 5/0476; A61B 5/0482; A61B 5/4088; A61B 5/72; A61B 5/7235; A61B 5/7271; A61B 5/04012
See application file for complete search history.

(56) References Cited

U.S. PATENT DOCUMENTS

| | | | | |
|---|---|---|---|---|
| 6,070,098 | A  * | 5/2000 | Moore-Ede et al. | 600/544 |
| 8,065,011 | B2 * | 11/2011 | Echauz et al. | 607/45 |
| 8,934,965 | B2 * | 1/2015 | Rogers et al. | 600/544 |
| 2003/0158587 | A1 * | 8/2003 | Esteller et al. | 607/45 |
| 2013/0072775 | A1 * | 3/2013 | Rogers et al. | 600/378 |
| 2015/0080695 | A1 * | 3/2015 | Rogers et al. | 600/378 |

OTHER PUBLICATIONS

Akaike, H., "A new look at the statistical model identification," IEEE Transactions on Automatic Control, Dec. 1974, 19(6), 716-723.

(Continued)

*Primary Examiner* — Navin Natnithithadha
(74) *Attorney, Agent, or Firm* — Baker & Hostetler LLP

(57) ABSTRACT

Oscillatory signals may be used to determine a region of a patient's body that is associated with a medical condition. As described herein, oscillatory signals may be detected using a high sensitivity, low specificity detector. The oscillatory signals may be representative of discrete events in a patient's body. The detected signals may be tested in the context of surrounding background activity to identify anomalous discrete physiologic events that are sufficiently different from the surrounding background activity. The anomalous discrete physiologic events having correlative morphological, time, or location characteristics may be automatically clustered and clusters of anomalous physiologic events may be determined that are indicative of at least one region of the patient's body that is associated with a medical condition.

28 Claims, 21 Drawing Sheets
(9 of 21 Drawing Sheet(s) Filed in Color)

(56) References Cited

OTHER PUBLICATIONS

Akiyama et al., "Focal cortical high-frequency oscillations trigger epileptic spasms: Confirmation by digital video subdural EEG", Clinical Neurophysiology, Oct. 2005, 2819-2825.
Allen et al., "Very high-frequency rhythmic activity during SEEG suppression in frontal lobe epilepsy," Electroencephalography and Clinical Neurophysiology, Feb. 1992, 82(2), 155-159.
Bagshaw et al., "Effect of sleep stage on interictal high-frequency oscillations recorded from depth macroelectrodes in patients with focal epilepsy," Epilepsia, Apr. 2009, 50(4), 617-628.
Barkley et al., "Safety and preliminary efficacy of the RNS responsive neurostimulator for the treatment of intractable epilepsy in adults," American Epilepsy Society Abstracts, 2006.
Begley et al., "The cost of epilepsy in the united states: An estimate from population-based clinical and survey data," Epilepsia, Mar. 2000, 41(3), 342-351.
Bien et al., "Characteristics and surgical outcomes of patients with refractory magnetic resonance imaging negative epilepsies," Archives of Neurology, Dec. 2009, 66(12), 1491-1499.
Bragin et al., "High-frequency oscillations after status epilepticus: Epileptogenesis and seizure genesis," Epilepsia, Sep. 2004, 45(9), 1017-1023.
Bragin et al., "High-frequency oscillations in human brain," Hippocampus, 1999, 9(2), 137-142.
Bragin et al., "Hippocampal and entorhinal cortex high-frequency oscillations (100-500 Hz) in human epileptic brain and in kainic acid-treated rats with chronic seizures," Epilepsia, Feb. 1999, 40(2), 127-137.
Bragin et al., "Interictal high-frequency oscillations (80-500 Hz) in the human epileptic brain: Entorhinal cortex," Annals of Neurology, Oct. 2002, 52(4), 407-415.
Bragin et al., "Local generation of fast ripples in epileptic brain," The Journal of Neuroscience, Mar. 2002, 22(5), 2012-2021.
Brinkmann et al., "Large-scale electrophysiology: Acquisition, compression, encryption, and storage of big data," Journal of Neuroscience Methods, May 2009, 180(1), 185-192.
Buzsaki et al., "Cellular bases of hippocampal EEG in the behaving rat," Brain Research, Oct. 1983, 287(2), 139-171.
Buzsaki et al., "High-frequency network oscillation in the hippocampus," Science, May 1992, 256(5059), 1025-1027.
Buzsaki et al., "Hippocampal network patterns of activity in the mouse", Neuroscience, 2003, 116, 201-211.
Chrobak et al., "High-frequency oscillations in the output networks of the hippocampal-entorhinal axis of the freely behaving rat," The Journal of Neuroscience, May 1996, 16(9), 3056-3066.
Cimatti, Z. et al., "Time-frequency analysis reveals decreased high-frequency oscillations in writer's cramp", Brain, Jan. 2007, 130, 198-205.
Clemens, Z. et al., "Temporal coupling of parahippocampal ripples, sleep spindles and slow oscillations in humans", Brain, Jul. 2007, 11 pages.
Cohen, J., "A coefficient of agreement for nominal scales," Education and Psychological Measurement, 1960, 20(1), 37-46.
Crépon et al., "Mapping interictal oscillations greater than 200 Hz recorded with intracranial macroelectrodes in human epilepsy," Brain, Jan. 2010, 133(Pt. 1), 33-45.
Csicsvari et al., "Fast network oscillations in the hippocampal CA1 region of the freely behaving rat," The Journal of Neuroscience, Aug. 1999, 19(16), RC20, 4 pages.
Csicsvari et al., "Oscillatory coupling of hippocampal pyramidal cells and interneurons in the behaving rat," The Journal of Neuroscience, Jan. 1999, 19(1), 274-287.
Curio G. Linking 600-Hz "spikelike" EEG/MEG wavelets ("sigma-bursts") to cellular substrates: concepts and caveats. J Clin Neurophysiol. Jul. 2000;17(4):377-96.
Dempster et al., "Maximum likelihood from incomplete data via the EM algorithm," Journal of the Royal Statistical Society, Series B (Methodological), 1977, 39(1), 1-38.
Draguhn et al., "Electrical coupling underlies high-frequency oscillations in the hippocampus in vitro," Nature, Jul. 1998, 394(6689), 189-192.
Draguhn et al., "Ripple (~200Hz) oscillations in temporal structures," Journal of Clinical Neurophysiology, Jul. 2000, 17(4), 361-376.
Dzhala et al., "Mechanisms of fast ripples in the hippocampus," The Journal of Neuroscience, Oct. 2004, 24(40), 8896-8906.
Engel et al., "High-frequency oscillations: What is normal and what is not?," Epilepsia, Apr. 2009, 50(4), 598-604.
Esteller et al., "Line length: An efficient feature for seizure onset detection," In Proceedings of the 23rd Annual International Conference of the IEEE Engineering in Medicine and Biology Society, Oct. 2001, vol. 2, 1707-1710.
Fisher et al., "High-frequency EEG activity at the start of seizures," Journal of Clinical Neurophysiology, Jul. 1992, 9(3), 441-448.
Foffani et al., "Reduced spike-timing reliability correlates with the emergence of fast ripples in the rat epileptic hippocampus," Neuron, Sep. 2007, 55(6), 930-941.
Gardner et al., "Human and automated detection of high-frequency oscillations in clinical intracranial EEG recordings," Clinical Neurophysiology, May 2007, 118(5), 1134-1143.
Grenier et al., "Focal synchronization of ripples (80-200 Hz) in neocortex and their neuronal correlates," Journal of Neurophysiology, Oct. 2001, 86(4), 1884-1898.
Grenier et al., "Neocortical very fast oscillations (ripples, 80-200 Hz) during seizures: Intracellular correlates," Journal of Neurophysiology, Feb. 2003, 89(2), 841-852.
Haberman et al., "Attenuation of seizures and neuronal death by adeno-associated virus vector galanin expression and secretion," Nature Medicine, Aug. 2003, 9(8), 1076-1080.
Hotelling, H., "Analysis of a complex of statistical variables into principal components," The Journal of Educational Psychology, Sep. 1933, 24(6), 417-441.
Hubert et al., "Comparing partitions," Journal of Classification, 1985, 2(1), 193-218.
Jacobs et al., "High frequency oscillations (80-500 Hz) in the preictal period in patients with focal seizures," Epilepsia, Jul. 2009, 50(7), 1780-1792.
Jacobs et al., "High frequency oscillations in intracranial EEGs mark epileptogenicity rather than lesion type," Brain, Apr. 2009, 132(Pt. 4), 1022-1037.
Jacobs et al., "Interictal high-frequency oscillations (80-500 Hz) are an indicator of seizure onset areas independent of spikes in the human epileptic brain," Epilepsia, Nov. 2008, 49(11), 1893-1907.
Jacobs J, Zijlmans M, Zelmann R, Chatillon CE, Hall J, Olivier A, Dubeau F, Gotman J. High-frequency electroencephalographic oscillations correlate with outcome of epilepsy surgery. Ann Neurol. Feb. 2010;67(2):209-20.
Jirsch et al., "High-frequency oscillations during human focal seizures," Brain, Jun. 2006, 129(Pt. 6), 1593-1608.
Joo et al., "Antiepileptic effects of low-frequency repetitive transcranial magnetic stimulation by different stimulation durations and locations," Clinical Neurophysiology, Mar. 2007, 118(3), 702-708.
Kaiser, J., "On a simple algorithm to calculate the energy of a signal," In International Conference on Acoustics, Speech, and Signal Processing, Albuquerque, NM, USA, Apr. 3-6, 1990, vol. 1, 381-384.
Khosravani H, et al., "Increased high-frequency oscillations precede in vitro low-Mg seizures", Epilepsia. Aug. 2005;46(8):1188-97.
Kobayashi K, et al., "Detection of changes of high-frequency activity by statistical time-frequency analysis in epileptic spikes", Clin Neurophysiol. Jun. 2009;120(6):1070-7.
Kramer MA, et al., "Sharp edge artifacts and spurious coupling in EEG frequency comodulation measures", J Neurosci Methods. May 30, 2008;170(2):352-7.
Kwan et al., "Early identification of refractory epilepsy," The New England Journal of Medicine, Feb. 2000, 342(5), 314-319.
Learned et al., "A wavelet packet approach to transient signal classification," Applied and Computational Harmonic Analysis, Jul. 1995, 2(3), 265-278.

(56) References Cited

OTHER PUBLICATIONS

Mackay, D. J., "Laplace's method: Information Theory, Inference, and Learning Algorithms," Cambridge University Press, 2005, 341-342.
MacQueen, J., "Some methods for classification and analysis of multivariate observations," In Proceedings of the 5th Berkeley Symposium on Mathematical Statistics and Probability, Berkeley, CA, 1967, vol. 1, University of California Press, 281-297.
Mallet, S. G., "A theory of multiresolution signal decomposition: The wavelet representation," IEEE Transactions on Pattern Analysis and Machine Intelligence, Jul. 1989, 11(7), 674-693.
McGill et al., "Variations of box plots," The American Statistician, Feb. 1978, 32(1), 12-16.
McLachlan, G., "Mahalanobis distance," Resonance, Jun. 1999, 4(6), 20-26.
Medtronic: Intercept epilepsy control system clinical trial, 2004, http://www.epilepsycontrol.com.
Mitra et al., "Analysis of dynamic brain imaging data," Biophysical Journal, Feb. 1999, 76(2), 691-708.
Mölle M, et al., "Hippocampal sharp wave-ripples linked to slow oscillations in rat slow-wave sleep",. J Neurophysiol. Jul. 2006;96(1):62-70. Epub Apr. 12, 2006.
Nuttall, A. H., "Near-optimum detection performance of power-law processors for random signals of unknown locations, structure, extent, and arbitrary strengths," Technical Report 11,123: Naval Undersea Warfare Center Newport Division, Apr. 15, 1996, 162 pages.
O'Keefe, J., "Place units in the hippocampus of the freely moving rat," Experimental Neurology, Apr. 1976, 51(1), 78-109.
Osorio et al., "Automated seizure abatement in humans using electrical stimulation," Annals of Neurology, Feb. 2005, 57(2), 258-268.
Pearson, K., "On lines and planes of closest fit to systems of points in space," Philosophical Magazine Series 6, 1901, 2(11), 559-572.
Rampp S, Stefan H. Fast activity as a surrogate marker of epileptic network function? Clin Neurophysiol. Oct. 2006;117(10):2111-7. Epub Jul. 14, 2006.
Rand, W. M., "Objective criteria for the evaluation of clustering methods," Journal of the American Statistical Association, Dec. 1971, 66(336), 846-850.
Roberts, S. J., "Extreme value statistics for novelty detection in biomedical signal processing," IEEE Proceedings Science, Technology, & Measurement, 2000, 47, 363-367.
Sander et al., "Epidemiology of the epilepsies," Journal of Neurology, Neurosurgery, and Psychiatry, Nov. 1996, 61(5), 433-443.
Sante, "Stimulation of the anterior nucleus of the thalamus for epilepsy," Jan. 18, 2005, http://clinicaltrials.gov/ct/show/NCT00101933, 4 pages.
Schevon et al., "Spatial characterization of interictal high frequency oscillations in epileptic neocortex," Brain, Nov. 2009, 132(11), 3047-3059.
Schwarz, G., "Estimating the dimension of a model," The Annals of Statistics, Mar. 1978, 6(2), 461-464.
Slepian et al., "Prolate spheroidal wavefunctions, Fourier analysis and uncertainty—I," Bell System Technical Journal, Jan. 1961, 40(1), 43-63.
Staba et al., "Increased fast ripple to ripple ratios correlate with reduced hippocampal volumes and neuron loss in temporal lobe epilepsy patients," Epilepsia, Nov. 2007, 48(11), 2130-2138.
Staba et al., "Quantitative analysis of high-frequency oscillations (80-500 Hz) recorded in human epileptic hippocampus and entorhinal cortex," Journal of Neurophysiology, Oct. 2002, 88(4), 1743-1752.
Stacey et al., "Technology insight: Neuroengineering and epilepsy-designing devices for seizure control," Nature Clinical Practice Neurology, Apr. 2008, 4(4), 190-201.
Stacey WC, Lazarewicz MT, Litt B. Synaptic noise and physiological coupling generate high-frequency oscillations in a hippocampal computational model. J Neurophysiol. Oct. 2009;102(4):2342-57. doi: 10.1152/jn.00397.2009. Epub Aug. 2009.
Staley, K.J., "Neurons Skip a Beat during Fast Ripples", Neuron, Sep. 20, 2007, 55, 828-830.
Stein et al., "An automated drug delivery system for focal epilepsy," Epilepsy Research, Apr. 2000, 39(2), 103-114.
Tanriverdi et al., "Long-term seizure outcome after mesial temporal lobe epilepsy surgery: corticalamygdalohippocampectomy versus selective amygdalohippocampectomy," Journal of Neurosurgery, Mar. 2008, 108(3), 517-524.
Thomson, D. J., "Spectrum estimation and harmonic analysis," Proceedings of the IEEE, Sep. 1982, 70(9), 1055-1096.
Tibshirani et al., "Estimating the number of clusters in a data set via the gap statistic," Journal of the Royal Statistical Society, Series B, 2001, 63(2), 411-423.
Traub, R. D., "Fast oscillations and epilepsy," Epilepsy Currents, May 2003, 3(3), 77-79.
Traub, R.D. et al., "High-frequency population oscillations are predicted to occur in hippocampal pyramidal neuronal networks interconnected by axoaxonal gap junctions", Neuroscience, 1999, 92(2), 407-426.
Urasaki, E. et al., "Effects of general anesthesia on high-frequency Oscillations in somatosensory evoked potentials", J Clin Neurophysiol, Oct. 2006, 23, 426-430.
Urrestarazu et al., "Interictal high-frequency oscillations (100-500 Hz) in the intracerebral EEG of epile ptic patients," Brain, Jul. 2007, 130(9), 2354-2366.
Urrestarazu et al., "High-frequency intracerebral EEG Activity (100-500 Hz) following interictal spikes", Epilepsia, Sep. 2006, 47(9), 1465-1476.
Usui et al., "Digital low-pass differentiation for biological signal processing," IEEE Transactions on Biomedical Engineering BME, Oct. 1982, 29(10), 686-693.
Van Gompel et al., "Phase I trial: Safety and feasibility of intracranial electroencephalography using hybrid subdural electrodes containing macro- and microelectrode arrays," Neurosurgical Focus, Sep. 2008, 25(3), E23, 1-6.
Vetterli et al., "Wavelets and filter banks: Theory and Design," IEEE Transactions on Signal Processing, Sep. 1992, 40(9), 2207-2232.
Wang et al., "All-purpose and plug-in power-law detectors for transient signals," IEEE Transactions on Signal Processing, Nov. 2001, 49(11), 2454-2466.
Wilson et al., "Reactivation of hippocampal ensemble memories during sleep," Science, Jul. 1994, 265(5172), 676-679.
Worrell et al., "High-frequency oscillations in human temporal lobe: Simultaneous microwire and clinical macroelectrode recording," Brain, Apr. 2008, 131(Pt. 4), 928-937.
Yang et al., "Focal cooling rapidly terminates experimental neocortical seizures," Annals of Neurology, Jun. 2001, 49(6), 721-726.
Ylinen et al., "Sharp wave-associated high-frequency oscillation (200Hz) in the intact hippocampus: Network and intracellular mechanisms," The Journal of Neuroscience, Jan. 1995, 15(Pt. 1), 30-46.
Zelmann, R. et al., "Improving the identification of High Frequency Oscillations", Clinical Neurophysiology, Jul. 2009, 120, 1457-1464.
Zijlmans, M. et al., "High-frequency oscillations mirror disease activity in patients with epilepsy", Neurology, Mar. 2009, 72, 979-986.
Ziflmans, M. et al., "High frequency oscillations and seizure frequency in patients with focal epilepsy", Epilepsy Research, Aug. 2009, 85, 287-292.

* cited by examiner

METHOD FOR AUTOMATIC, UNSUPERVISED CLASSIFICATION OF HIGH-FREQUENCY OSCILLATIONS IN PHYSIOLOGICAL RECORDINGS

CROSS REFERENCE TO RELATED APPLICATIONS

This application claims the benefit of U.S. Provisional Patent Application Ser. No. 61/444,560, filed Feb. 18, 2011, the contents of which are hereby incorporated by reference in their entirety.

GOVERNMENT RIGHTS

This invention was made with government support under grant No. R01 NS048598 and NS041811 awarded by the National Institute of Health. The government has certain rights in the invention.

FIELD OF THE INVENTION

The present invention relates to a method for automatically identifying discrete physiological events such as high-frequency oscillations within the human body and classifying such events for diagnostic purposes.

BACKGROUND

Quality of life for the more than 15 million people worldwide with drug-resistant epilepsy is tied to how precisely the brain areas responsible for generating their seizures can be localized. Current approaches to seizure localization are non-quantitative, and may include human interpretation of magnetic resonance and computed tomography images, neuropsychological test results, and scalp EEG recordings. In cases where these tests are suggestive of focal seizures but precise localization remains elusive, patients are often recommended for an invasive monitoring procedure, intracranial EEG (iEEG), in which recording electrodes are implanted within the skull cavity (typically beneath the dura mater) in order to improve signal fidelity.

Using the iEEG for seizure localization is subjective and labor-intensive. Neurologists trained to recognize stereotypical epileptiform and seizure patterns use commercial software to visualize multielectrode data streams that are often collected continuously over days or weeks. The goal is to manually identify putative channels (i.e., electrode recordings) showing earliest electrographic seizure onset. Qualitative information gleaned from iEEG screening is then used in planning the surgical procedure.

Surgeries based on these current approaches to localization are moderately effective. In one study, for example, focal tissue resections in medically refractory mesial temporal lobe epilepsy patients, guided by iEEG-determined clinical identification of the "seizure onset zone," led to seizure freedom in about 50% of patients at 5 years post-operation. Furthermore, not all patients originally considered for surgery are ultimately deemed eligible: brain areas flagged for excision may overlap with regions vital to everyday functioning (e.g., speech, motor control, etc.), in which case they may not be safely removed.

The marginal outcomes of surgeries based on qualitative seizure localization and the preclusion of qualitative localization within real-time implantable systems (which promise to help patients who are ineligible for surgery) have prompted a search for quantitative signatures of epileptogenic brain. High Frequency Oscillations (HFOs), quasi-sinusoidal bursts of neurophysiological activity that persist for tens of milliseconds and have predominant energy in the frequency range between 100 and 500 Hz, have emerged as a leading candidate.

HFOs may be recorded using metal electrodes placed within the brain parenchyma; on the surface of the cortex, with or without one of the three meningeal layers—the dura mater, the arachnoid membrane, and the pia mater—interposing; or, less likely, on the surface of the skull bone; on the surface of the periosteum; or on the surface of the skin (i.e., the scalp). The recording electrodes typically are, but need not be, in direct physical contact with biological tissue, as the signals of interest may be transmitted capacitively.

The de facto standard in research settings for detection and classification of HFOs is human-intensive data marking. These manual approaches are both unreliable and infeasible within the time horizons for patient care in clinical settings. Described herein are systems, methods, and apparatus that address these problems.

SUMMARY

Various techniques are described herein for automatically detecting, classifying, and processing oscillatory signals for use as a biomarker for a physiological event. According to one embodiment, a method is described for detecting and classifying oscillatory signals representative of discrete events in a patient's body using a high sensitivity, low specificity detector. The detected signals may be tested in the context of surrounding background activity to identify anomalous discrete physiologic events that are sufficiently different from the surrounding background activity. The anomalous discrete physiologic events may be automatically clustered into clusters of anomalous physiologic events having correlative morphological, time, or location characteristics. At least one cluster of anomalous physiologic events may be determined that is indicative of at least one region of the patient's body that is associated with a medical condition.

According to an embodiment, the discrete events may be associated with the patient's brain and at least one cluster of anomalous physiologic events may be determined that is indicative at least one region of the patient's brain that may be involved in generating epileptic seizures.

According to an embodiment, a system is described for automatically detecting, classifying, and processing oscillatory signals for use as a biomarker for a physiological event. The system may include at least one high sensitivity, low specificity detector and a processor. Each high sensitivity, low specificity detector may be configured to detect and classify oscillatory signals representative of discrete events in a patient's body. The processor may be configured to test the detected signals in the context of surrounding background activity to identify anomalous discrete physiologic events that are sufficiently different from the surrounding background activity. The processor may also be configured to automatically cluster anomalous discrete physiologic events into clusters of anomalous physiologic events having correlative morphological, time, or location characteristics. The processor may be further configured to determine at least one cluster of anomalous physiologic events indicative of a region of the patient's body that is associated with a medical condition.

Other features and aspects, as well as other medical applications, of the methods, systems and apparatus described herein will become apparent from the following detailed description and the associated drawings.

BRIEF DESCRIPTION OF THE DRAWINGS

The file of this patent or application contains at least one drawing executed in color. Copies of this patent or patent application publication with color drawings will be provided by the Office upon request and payment of the necessary fee.

The foregoing summary, as well as the following detailed description, is better understood when read in conjunction with the appended drawings. For the purpose of illustrating the method and apparatus described herein, there is shown in the drawings exemplary embodiments; however, the invention is not limited to the specific methods and instrumentalities disclosed. In the drawings.

DETAILED DESCRIPTION OF ILLUSTRATIVE EMBODIMENTS

Figure 1:
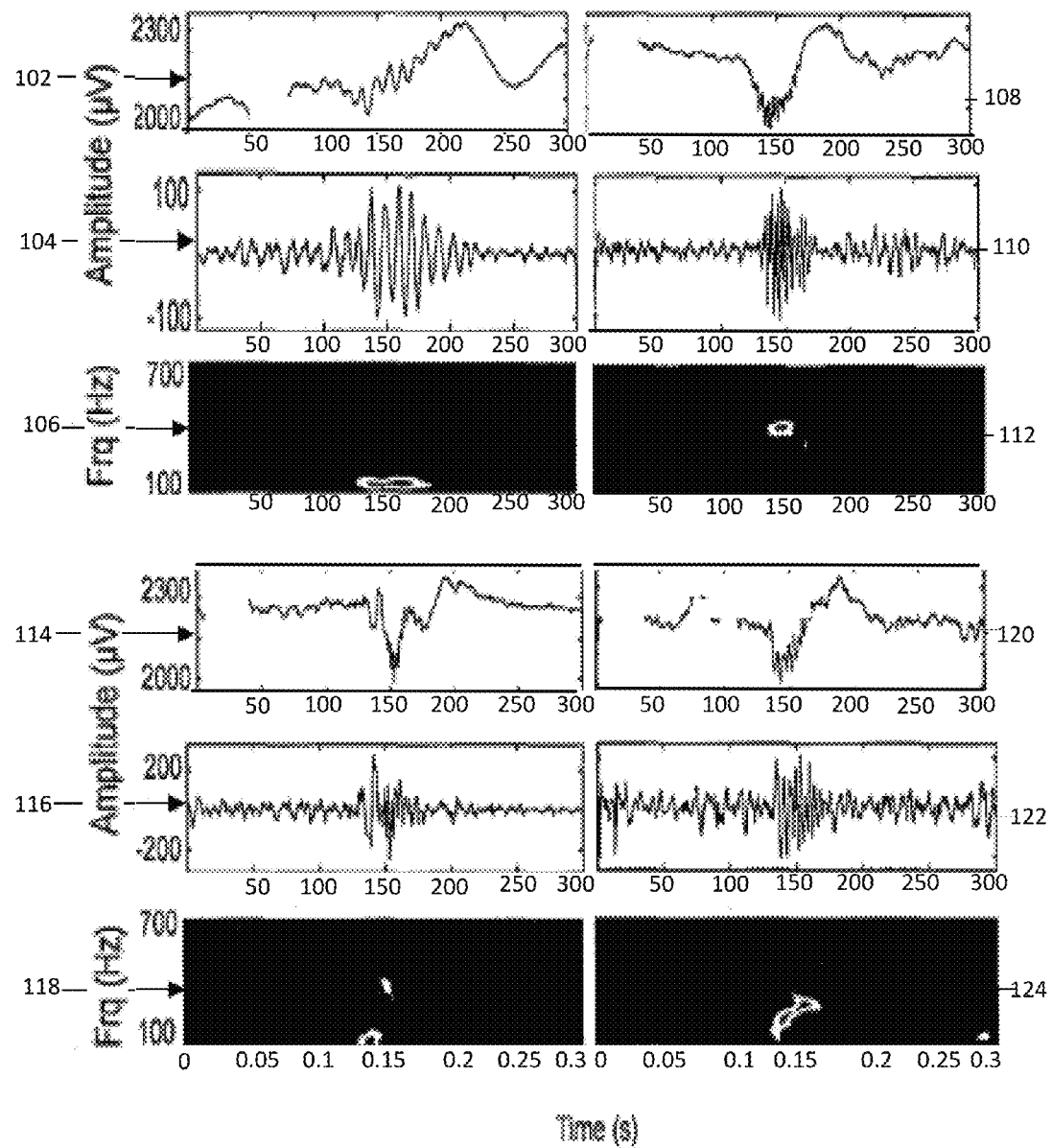
FIG. 1 illustrates examples of 100-500 Hz high-frequency oscillations recorded in patients with mesial temporal lobe epilepsy.

Systems, methods, and apparatus are described herein for determining a region of a brain that may be involved in generating epileptic seizures. According to an example embodiment, a method is described for detecting and/or classifying signals that are representative of discrete physiologic events in the brain using a high sensitivity, low specificity detector. The detected signals may be enhanced by testing the detected signals in the context of surrounding background activity. Such testing may identify anomalous discrete physiologic events that are sufficiently different from the surrounding background activity. For example, it may be determined that the discrete physiologic events are sufficiently different from surrounding background activity if the difference overcomes a given threshold. The anomalous discrete physiologic events may be clustered into anomalous physiologic events having correlative morphological, time, and/or location characteristics. The method may then determine that a cluster of the anomalous physiologic events is indicative of a region of the brain that may be involved in generating epileptic seizures.

Described herein is an unsupervised computational algorithm for automatically detecting and/or classifying electrical signals recorded from the brain. In an exemplary embodiment, the signals are high-frequency oscillations (HFOs) that may be used to delineate the region(s) of human brain involved in initiating epileptic seizures. In natural extensions, the algorithm may be tuned to process brain oscillations of frequencies different than 100-500 Hz HFOs; other forms of paroxysmal brain activity such as action potentials and epileptic spikes; and/or other brain or body-generated (e.g., heart, muscle, bladder, retina, cochlea) transient signals measured with chemical, electrical, optical, thermal, magnetic, and/or mechanical (e.g., pressure) sensors. Applied to HFOs in the exemplified configuration, the algorithm may be implemented in at least two types of medical devices: 1) intracranial electroencephalographic (iEEG) monitoring systems used in pre-surgical evaluation and surgical planning for partial epilepsy patients who are unresponsive to antiepileptic drugs; and 2) brain-implantable devices that monitor, predict, detect, abort, and/or control epileptic seizures by using feedback from sensors to deliver targeted therapy (e.g., electrical or magnetic stimulation, gene therapy, drug delivery, and/or temperature modulation). Devices in category 1 and/or category 2 may be used for clinical purposes.

According to an embodiment, an algorithm described herein may enable quantitative seizure localization in devices in each of the aforementioned categories. According to an embodiment, the algorithm may find application in devices that monitor, predict, detect, abort, and/or control non-epileptic abnormal or normal physiological processes.

The algorithm described herein may be comprised of at least three stages. In the first stage, candidate HFO events may be detected in bandpass filtered brain recordings using a method that is sensitive but highly non-specific. In the second stage, a statistical model of the local background activity surrounding each candidate event may be built, and events bearing too large a spectral similarity to the background according to the model may be discarded from candidacy. In the third stage, computational features may be extracted from the retained candidates and these features may be used, after a dimensionality reduction step for example, as inputs to a classifier. The rates or other characteristics (e.g., amplitudes, durations, and/or morphologies) of events in one or more of the classes found by the algorithm may be used to make machine and/or human decisions about which brain regions are responsible for generating seizures, and should therefore be resected or otherwise targeted for therapy.

The algorithm may be designed and implemented in computer code (e.g., MATLAB®). For example, it may be run on a data set comprised of continuous iEEG recordings from patients, and its ability to identify HFOs of clinical interest may be validated against the markings of expert human data reviewers. The utility of the algorithm in finding classes of HFOs related to clinically determined regions of seizure-onset may also be demonstrated. At least one embodiment may include developing computational efficiency so that more channels may be processed in real-time (such as greater than 30 channels for example), integrating the algorithm with current seizure localization systems and devices, and/or collecting sufficient data to learn appropriate statistical rules for making machine predictions about pathology on an individual-channel basis.

Also described herein are systems, methods, and apparatus for extracting quantitative seizure-localizing information from multi-electrode data automatically. As described above, these systems, methods, and apparatus may be included in at least two types of medical devices: 1) intracranial electroencephalographic (iEEG) monitoring systems used in pre-surgical evaluation and surgical planning for partial epilepsy patients who are unresponsive to antiepileptic drugs; and/or 2) brain-implantable devices that monitor, predict, detect, abort, and/or control epileptic seizures by using feedback from sensors to deliver targeted therapy (e.g., electrical or magnetic stimulation, gene therapy, drug delivery, temperature modulation, etc.). The devices of category 1 may be used in determining the accuracy and precision of seizure localizations, as well as providing an increase in the number of screened patients in whom localizations can be achieved. This may enable more patients to achieve seizure-freedom through resective surgery, with fewer side-effects. The devices of category 2 may enable the use of HFOs as a control signal to drive closed-loop therapy. A class of HFO-responsive neurostimulators may provide therapy for patients who are ineligible for surgery, and/or may provide an effective and less invasive alternative to surgery for patients who are eligible.

Some authors have reported on semi-automated approaches to HFO detection, which use intensive visual pre- and post-processing in conjunction with machine detection. Embodiments described herein may include an algorithm that fully automates extracting and/or classifying 100-500 Hz transient high frequency oscillations in intracranial EEG recordings.

Further described herein is an algorithm for fully automated HFO processing. This algorithm may enable the use of HFOs for seizure localization during pre-surgical evaluation and/or surgical planning. The algorithm may permit the use of HFOs as control signals within implantable seizure control devices. Semi-automated approaches to HFO processing, which may use a high degree of time-consuming manual intervention, may be suitable in research applications.

Some computational implementations for detecting or monitoring physiological activity may utilize supervised learning. For example, they may use human-labeled "training data" to teach a machine to make decisions. These implementations by definition may not look beyond what humans may identify as important. The systems, methods and apparatus described herein may not implement human marking or validation. They may uncover signal sub-types and/or characteristics which may be unknown to humans, but potentially more effective for diagnosis and therapy.

For some individuals, seizures may not be controlled by any combination of traditional therapies—medication and/or focal resection of brain tissue. There have been advances in surgical technology and substantial innovation in antiepileptic drug therapy, which has served to mitigate the side-effects of treatment rather than make more people seizure-free. Alternative treatment technologies may be available as described herein, such as implantable devices designed to detect, predict, prevent, and/or abort seizures.

Seizure control devices may be implemented in clinical trials. The ultimate success and widespread clinical adoption of these devices may depend upon a more complete understanding of where, when, and how to deliver therapy within the brain.

Embodiments described herein may be directed to the first of these three interconnected issues, for example, where to direct treatment. It may be difficult to determine, for example, how the timing and/or structure of newly proposed therapies like controlled electrical or magnetic stimulation, focal cooling, gene therapy, and/or drug-delivery—or the efficacy of present day surgical resections may be optimized without having a reasonable picture of what may be the therapeutic targets.

Research aimed at finding therapeutic targets has been centered primarily on so-called "focal" epilepsies, in part because they may be perceived to be the most clinically tractable. Though diverse in etiology, these epilepsies may share the characteristic that the earliest electrographic abnormalities preceding seizures may consistently be observed on a small and usually compact subset of recorded electroencephalography (EEG) channels. This has led to a conceptual model of seizure generation that posits the existence of an epileptic focus: a time-stable and/or well circumscribed population of cells in which pathologic activity originates before propagating more globally within the brain. Moderate support for this conceptualization of focal epilepsies may be provided by neurosurgical outcomes.

The epileptic focus may be a useful construct. At the same time, it may permit a broader interpretation of what might comprise it. Rather than a single, compact and time-stable group of neurons, the epileptic focus may be a spatially distributed cluster of loci, possibly one whose members may change across time. A more suitably general term for the epileptic focus viewed this way, which may have traction in the epilepsy research community, is "epileptogenic network." Whatever its neural substrate, the epileptogenic network may represent the origin of pathologic activity and may emit a characteristic signature that may be detected using some measurement modality. The intracranial electroencephalogram (iEEG) may be described herein. The use of some tools, such as high bandwidth recordings for example, may indicate that a candidate biomarker for the epileptogenic network is emerging in this modality: transient, quasi-periodic activity with frequency between 100 and 500 Hz, collectively termed, "high-frequency oscillations" (HFOs) to distinguish it from the slower activity (0.1-40 Hz) more commonly studied in the epilepsy and/or used to make clinical decisions. Representative examples of HFOs are shown in FIG. 1.

FIG. 1 shows four examples of 100-500 Hz high-frequency oscillations (illustrated in FIG. 1 as 102-124) recorded in patients with mesial temporal lobe epilepsy. Each HFO is depicted in three different views: unfiltered iEEG with the HFO centered at 0.15 s (102, 108, 114, 120); the corresponding bandpass filtered iEEG (80-1000 Hz) (104, 110, 116,

122); and a spectrogram (2.6 ms window) of the same 0.3 s duration iEEG segment (106, 112, 118, 124). The vertical scaling in the unfiltered (102, 108, 114, 120) and the corresponding bandpass filtered (104, 110, 116, 122) views is approximate.

HFOs may be used (e.g., clinically) to provide accurate information about seizure-generating brain areas, as compared to iEEG-based seizure localization for example: such as visual inspection of recordings for channels showing early seizure onset for example. If a localizing capacity is demonstrated for HFOs using the methods, systems, and apparatus described herein, it may impact clinical practice, which may increase the efficacy of surgical resections to step seizures and/or the number of medically refractory patients who become eligible for surgery.

The ability to mine HFOs from iEEG automatically may be used to study their relationship with seizure onset regions effectively. Automation may reduce clinician workload and/or the potential for human error and/or bias to impact the localization process. Automation may also influence the design of implantable seizure warning and/or control devices, which may be a promising alternative for patients who are ineligible for surgery, for example, either because their seizures are localized to eloquent cortex whose removal may lead to unacceptable neurological deficits, or because their epileptogenic networks may be multi-focal, broadly distributed, and/or dynamically changing. In these cases, HFOs may provide the critical control signal for closed-loop devices, which may indicate where and/or when to deliver therapy for maximal efficacy.

The clinical utility of HFOs as seizure localizing signals may be tested by correlating HFO properties with treatment outcomes and/or by conducting prospective clinical trials in which HFO measures are used to dictate treatment. To enable such studies to be performed, reliable tools may be developed, for the automated detection and/or classification of HFOs for example; proposed machine implementations with human performance may be compared; it may be determined whether there are preferred electrode geometries for recording HFOs; and/or an understanding of which attributes or classes of HFOs are characteristically epileptic and which are normal may be determined.

Systems, methods, and apparatus are described herein for using an algorithm for the fully automated detection and/or classification of HFOs. Also described is the manner in which tools may be assembled and their application to HFO analysis.

One embodiment described herein includes treating the post-processing of an initial set of highly noise-polluted detections in specialized filtering stages. One filtering stage may be designed to address a particular vulnerability of the detector, and/or its role may be framed as a frequency domain outlier detection problem that may be tackled using density estimation techniques. Another filtering stage may include a problem formulation, being a treatment of HFO candidates that uses the exploratory data analysis technique of clustering for example. The computational features from which the inputs to the machine classifier are derived are described herein.

Findings about behavior are also described herein, such as the degree to which human expert reviewers may agree about what constitutes an HFO and/or how the automated classifier compares with their decisions and/or gives insight into their biases. A data-driven argument may be provided for the downplaying of highly coveted "ground truth" data in early stages HFO discovery.

Also described herein is one of a number of investigations of neocortical, rather than mesial temporal for example, HFOs in humans; and a description of spontaneous neocortical HFOs in patients with no history of seizures. As described herein, it may be determined whether HFOs in any of a number of automatically detected clusters may show changes in rate based on their locations within and/or outside the physician-labeled seizure onset-zone. It may be determined whether electrodes with diameters on the micrometer scale may record HFOs of higher frequencies than standard millimeter-scale clinical macroelectrodes. The embodiments described herein may be used in the laboratory and/or the clinic for example.

Narrowband transient field-potential oscillations greater than 100 Hz and/or lasting tens of milliseconds, originally termed "ripples," have been observed in in vivo extracellular microelectrode recordings from mammalian hippocampus. Ripples may be a synonym for "high-frequency oscillations." The term "high-frequency oscillation" may signify the grouping of two putatively distinct classes of oscillations within the range 100-500 Hz ripples (100-200 Hz) and "fast ripples" (250-500 Hz).

Conditions are identified under which ripple-like activity has been described in experiments. One condition may include when local field potentials may be relatively small (e.g., ~200 µV) and principal cells are presumed not to be particularly depolarized. Another condition may include when large depolarizing events like sharp-waves are observed in conjunction with ripples. At least eight subcategories of activity may be delineated within these classes, not necessarily disjoint, to which researchers have attached the "ripple" label. Factors distinguishing these categories may include: spectral composition of the ripples; region of the brain in which they may be observed; influence of the ionic composition of the extracellular fluid (in slice bath); whether they occur spontaneously or after tetanic stimulation; effect of chemical blockage of GABAa receptors by bicuculline; and/or the characteristics of the background activity upon which ripples are superimposed (e.g., sharp-waves, evoked somatosensory potentials, and/or synchronized bursts).

Described herein are embodiments that include spontaneous, transient, quasi-periodic, activity whose peak frequency may fall in the band between 100 and 500 Hz, recorded in vivo using intracranial electrodes. For example, neocortical HFOs may be described herein, as well as findings from the hippocampal-entorhinal axis, with a focus on epileptic humans for example. Described herein is the relationship between ripples and seizure generation. This relationship may be shown through such examples as: 1) those that give relatively strong statistical support for their claims; and 2) those that appear to have been particularly influential in inspiring further research and shaping current clinical opinion, even if their conclusions were based on less quantitative analyses.

Results pertaining to relationships between ripples and unit activity may be deemphasized, including physiological and/or computational investigations of mechanisms by which ripples may be generated. These studies may be performed in highly controlled environments, in anesthetized animals and/or slice preparation, with the full complement of chemical, electrophysiological, and/or histopathological tools for targeting and/or confirming placement of electrodes, and/or identifying cortical layers and specific neuron classes—techniques that may not be used in the clinical environment for a variety of ethical and practical reasons.

Single-patient case studies, studies whose findings may confirm previous results, and/or those whose claims may be based on anecdotal rather than statistical evidence may be neglected.

High-frequency oscillations may be divided into at least two classes. One class may include "ripples," with peak frequency between approximately 80 and approximately 160 Hz. Another class may include "fast ripples," with peak frequency, between approximately 250 and approximately 500 Hz. High-frequency oscillations may also include distinct ripple and fast ripple classes,—which may include approximately 100-130 Hz for the former and approximately 140-200 Hz for the latter. The fast ripple class may be unilateral in a given patient while the ripple class may occur in both hemispheres. Fast ripples may occur during the same behavioral states and "randomly interspersed" with ripples on a given electrode.

The binary classification of detections between ripples and fast ripples may be based on peak spectral frequency. The ratio of fast ripple to ripple rates may be significantly larger for channels ipsilateral to the clinically determined seizure-onset zone than for contralateral channels. The latter difference may be linked to the tendency for hippocampal atrophy to occur on the ipsilateral side. Ripples and fast ripples may be significantly shorter in duration on the ipsilateral side.

Others have found that there may be increases in the rates of both classes ipsilateral to the seizure-onset zone. In addition, attention has been called to the spectral complexity of detected events, noting the difficulty of labeling detections as ripples or fast ripples based on a single value (peak frequency).

The finding in mesial temporal lobe structures of rate increases for ripples and/or fast ripples in the seizure onset zone may be difficult to interpret due to heavy reliance on manual processing, aggregation of patients with neocortical and mesial temporal epilepsy when reporting significance, and/or the use of statistical tests that rely on distributional assumptions where nonparametric methods may be more appropriate. Using the embodiments described herein, properties of high-frequency oscillations, such as ripples or fast ripples for example, may be measured and used to predict the occurrence of seizures.

Narrowband voltage transients with peak frequencies in the range between 100 and 500 Hz may be useful biomarkers for epileptogenic tissue. The subdivision of this band into "ripple" and "fast ripple" oscillations may be physiologically and/or clinically relevant. At least some properties of these transients may carry the information for distinguishing pathologic from non-pathologic tissue. HFOs may have predictive value for signaling seizure occurrence.

The spatial scale over which high-frequency oscillations may be generated and whether electrodes of different sizes preferentially record HFOs of different types is described herein. There is controversy in the field. Some groups hold that pathological HFOs are most readily recorded with electrodes on the order of tens of micrometers or smaller. Others contend that no useful information is lost using standard, millimeter-scale clinical electrodes.

Studies of high-frequency oscillations in epilepsy may suffer from small sample-size, and/or may substitute anecdotal evidence and descriptive statistics for more careful quantitative analysis. Studies that may take more rigorous approaches that may yield enticing results may be hampered by selection bias arising, primarily out of the need to reduce the volume of data available for analysis. Data reduction may be an acute problem because automated HFO analysis may not be good enough to eliminate the burden of human pre-screening and/or post-processing. The reliable automated HFO processors described herein and their blinded deployment across long, continuous records drawn from larger numbers of patients may be used to make definitive statements about the relationship between HFOs and seizure generation.

High-frequency oscillations (HFOs) may be observed in animal and/or human intracranial recordings during normal and/or aberrant brain states. The relationship between subclasses of these oscillations may be used to identify epileptic brain. Studies of HFOs in epilepsy have been hampered by selection bias arising primarily out of the reduction in the volume of data so that clinicians may manually review it. An algorithm may be described herein for detecting and/or classifying HFO signals automatically. The tractability of analyzing a data set of unprecedented size may be demonstrated, such as over 31,000 channel hours of intracranial electroencephalographic recordings (iEEG) from micro- and macro-electrodes in humans for example. Using an unsupervised approach that may not pre-suppose a specific number of clusters in the data, direct evidence may be shown for the existence of distinct classes of transient oscillations within the 100 to 500 Hz frequency range in a population of nine neocortical epilepsy patients and two controls. The four classes found, three plus one putative artifact class for example, may be consistent with the identification of "ripple" and/or "fast ripple" oscillations, and identifies a less examined class of mixed-frequency events.

High-frequency oscillations (HFOs)—narrowband transients recorded on the intracranial electroencephalogram (iEEG), having predominant frequency between roughly 100 and 500 Hz and lasting on the order of tens of milliseconds—may be used to identify epileptogenic brain tissue. From a clinical perspective, HFOs may be used as biomarkers and may improve the outcomes of surgical resections in patients with medication resistant epilepsy, such as by augmenting or replacing signals currently used to delineate epileptogenic cortex for example. HFOs may serve as input signals to controllers within implantable devices designed to deliver therapeutic intervention, such as targeted electrical stimulation, drug delivery, and/or tissue cooling, such as in a closed-loop fashion for example. Such devices may help the population of medically refractory epilepsy patients who are not candidates for resective surgery. Such devices may help candidates because their seizures may appear to emanate from "eloquent" cortical areas with vital function, and/or because epileptiform activity may appear diffuse or multi-focal within the brain.

Studies of HFOs in epilepsy may rely on human-intensive implementations to extract the signals of interest from multichannel iEEG. With the goal of increasing the tractability of labor-intensive marking and analysis tasks and/or improving the interpretability of results, investigators may perform dramatic data reduction steps before committing the data to statistical analysis. Examples of data culling measures may include pre-selecting: 1) subjects, electrodes, channels, and/or time-epochs that, upon visual pre-inspection, may show prominent examples (e.g., high signal-to-noise ratio) of the activity to be analyzed; 2) electrodes or contacts which, according to MRI, may appear located in gray matter or specific brain structures; 3) data recorded during certain states of consciousness, which may be slow-wave sleep; 4) data recorded during specific brain states such as interictal, preictal, and/or ictal periods; 5) data recorded from periods deemed artifact-free, such as by human reviewers; and/or 6) data—or a subsample thereof, such as a 10-minute segment for example—that may satisfy some combination of the above criteria. In another example, machine-based HFO detection may be employed in semi-automated procedures in which similar human screening may occur before the automatic detector is deployed, as well as after, in an attempt to reduce the number of spurious machine detections. Such quasi-automated methods may be designed with the aim of reducing the workload for human reviewers.

Based in large part on human observation, studies of HFOs in epilepsy may presuppose two discrete categories of these oscillations that may be distinguished by the sub-band within 100-500 Hz in which the majority of the transient signal's energy may lie. The two types of high-frequency oscillations are termed "ripples" and "fast ripples," and statistical analyses of HFO properties may be preceded by the forced classification of detected events as one of these two types.

Systems, methods, and apparatus are described for automatically detecting and/or classifying high-frequency oscillations in the human intracranial electroencephalogram. In an example embodiment, no data pre-selection may be used (e.g., beyond the choice to study patients with epilepsy believed to be of neocortical origin and/or control patients) and recorded data may be analyzed from available channels in available patients. The existence of two distinct subpopulations of HFOs may not be presupposed. This may be used to inform the design of some of the features that may be used as inputs to the classifier. An unsupervised rather than supervised scheme may be developed for event classification. This may be because a) what constitutes a physiologically or clinically meaningful HFO are still evolving, and the former framework may be more natural for exploratory analysis; and b) studies in which "expert" human reviewers have been asked to mark HFO-like activity on the iEEG have shown poor inter-rater reliability and reproducibility. The categorization of events may not be constrained to two types. So, classification may not pre-specify the numbers of HFO classes present in the data.

Described herein is a tool for automatically processing and/or organizing large quantities of neurophysiologic data containing spontaneous, transient events, in a manner that may minimize selection bias and/or human subjectivity and/or labor. Distinct classes of oscillations may exist which have been taken for granted, strengthening the use of "ripples" and "fast ripples" as meaningful physiologic labels, and/or suggesting that a third class of oscillations containing components of both frequencies may be investigated.

In an example experiment, nine patients with medically refractory partial epilepsy believed to be of neocortical origin underwent implantation of subdural electrodes to localize the seizure onset zone after noninvasive monitoring was indeterminate. The location, number, and/or type of intracranial electrodes (grid and/or strip and/or depth electrodes) were determined by a multi-disciplinary team, including neurosurgeons, neurologists, netiroradiologists, and neuropsychologists, as part of routine clinical care. Standard clinical grid and strip electrodes were modified under an Institutional Review Board (IRB)-approved research protocol, by adding arrays of non-penetrating platinum-iridium microwires (40 µm diameter, with intra-array spacing of 0.5-1 mm center-to-center) between the clinical, 4 mm diameter contacts. Standard clinical depth leads were similarly modified, in two ways: 1) by embedding microwires around the circumference of the lead-body between the 2 mm long clinical contacts; and 2) by passing a bundle of microwires within the lumen of the lead, so that they protruded by approximately 7-8 mm from the distal tip. Schematic depictions of the electrode modifications and an image of a typical implanted subdural grid are shown in FIG. 2.

Figure 2:
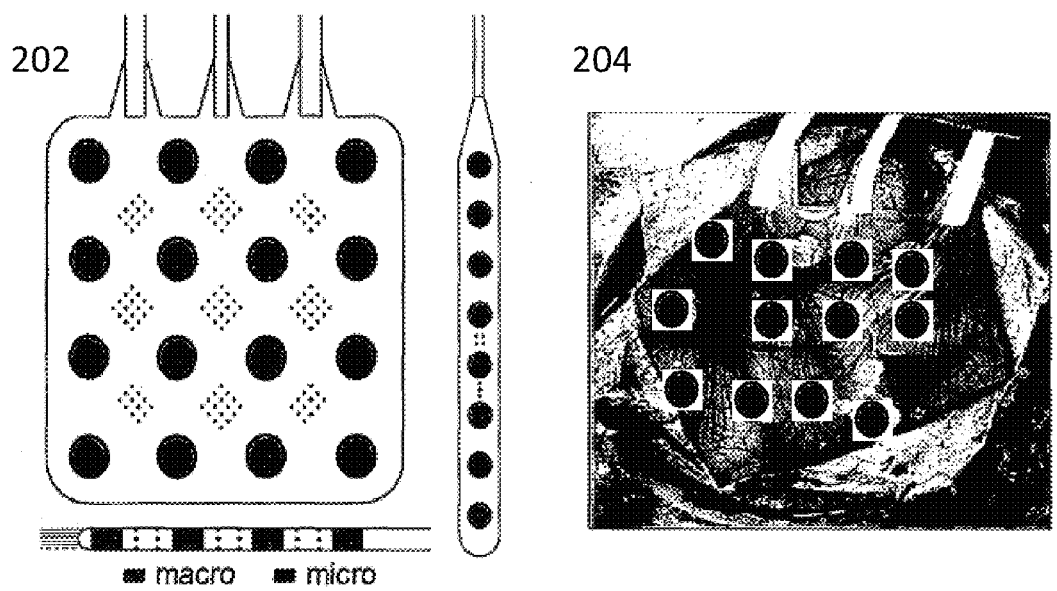
FIG. 2 illustrates schematic depictions of electrode modifications and an image of a typical implanted subdural grid.

FIG. 2, at 202, shows example schematics for hybrid grid and strip (above) and depth (below) electrodes. Arrays of microwire contacts may be located at regular intervals between the larger clinical contacts (drawings are not to scale). FIG. 2 also shows, at 204, an image showing subdural placement of a hybrid grid electrode. The images may be implemented using macro and/or micro recordings. For example, the electrode array illustrated in FIG. 2 may be a macro array, a micro array, or a hybrid macro-micro array (as illustrated in FIG. 2).

Two "control" patients, with chronic intractable facial pain but with no history of seizures, were similarly implanted as part of an unrelated, IRB-approved research protocol investigating electrical stimulation of motor cortex as a potential treatment for their condition.

In addition to intracranial electrodes, a limited montage of standard gold scalp electrodes (EOM1, EOM2, Fp1, Fp2, Fpz, C3, and C4) was placed on all patients, as well as electrodes to record electromyographic signals from the chin and tibialis anterior surface. Two stainless steel surgical sutures were placed at the vertex region of the head at the time of surgery and used as reference and ground, respectively, for both intra and extracranial electrodes.

Continuous, long-term data were acquired at 32,556 samples per second and 20 bits per sample (stored), from up to 144 channels in each patient. The input dynamic range was ±132 mV and the noise level was ~1.3 µV root-mean-square (RMS), yielding approximately 18 effective bits. Recordings were made using direct current (DC) capable amplifiers, and a 9 kHz analog lowpass filter, was employed to minimize aliasing effects. The bandwidth of the raw recordings was thus approximately near-DC –9 kHz.

Figure 3:
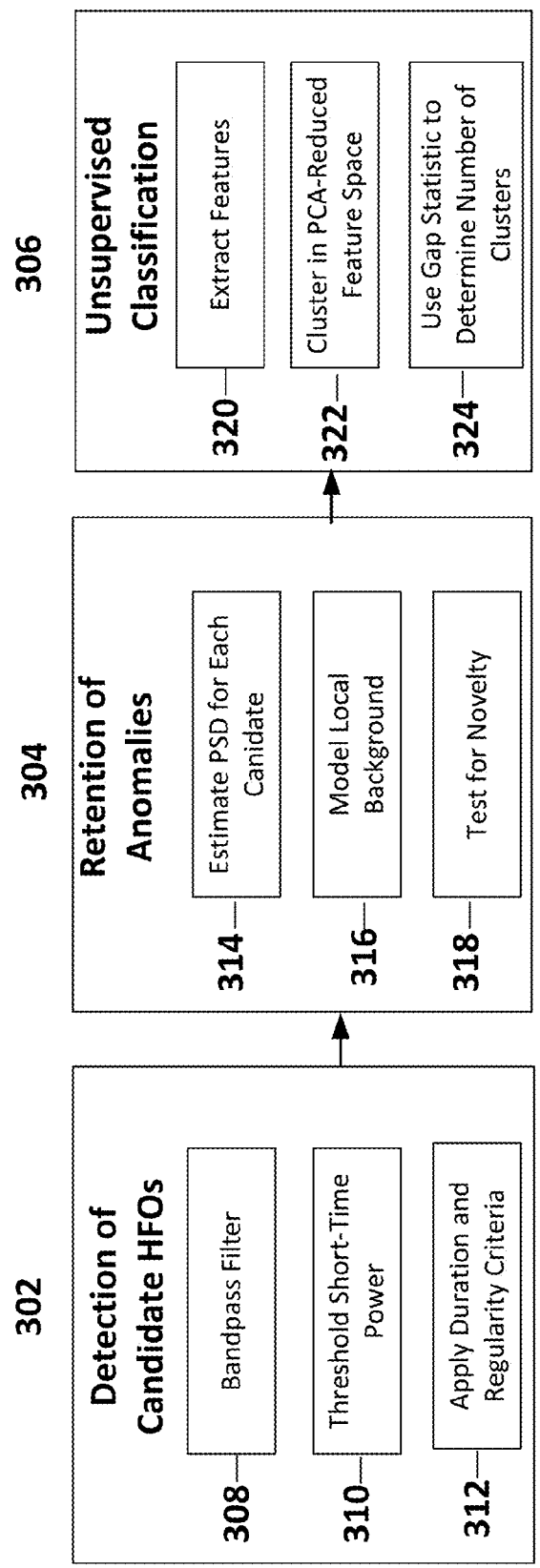
FIG. 3 is a block diagram illustrating a three-stage detection and/or classification algorithm.

The automated HFO detection and/or classification algorithm described herein may be comprised of a number stages, as illustrated in FIG. 3 for example. FIG. 3 is a block diagram illustrating the three-stage detection and/or classification algorithm. An exemplary embodiment of the first, second, and third stages are further described herein.

In one stage, such as a first stage illustrated at 302 for example, candidate HFO events may be detected at 308 in the bandpass filtered iEEG, to be sensitive, but which may be highly non-specific. In this first stage illustrated at 302, a threshold short-time power and/or duration and regularity criteria may be implemented at 310 and/or 312 respectively. This initial pass over the data set may reduce its size. In another stage, such as a second stage illustrated at 304 for example, a statistical model of the local background iEEG surrounding each candidate event may be built, with anomalies being retained. Events bearing too large a spectral similarity to the background activity according to the model may be discarded from candidacy. In the second stage illustrated at 304, a power spectral density estimate (PSD) may be determined for each candidate at 314, a model local background may be determined at 316, and/or a test may be performed for novelty at 318. In another stage, such as a third stage illustrated at 306 for example, computational features may be classified. The computational features may be extracted at 320 from the retained candidates (which may be labeled "anomalies," since they may or may not represent clinically meaningful events for example). These computational features may be used, such as after a dimensionality reduction step for example, as inputs to a classifier. The classifier may automatically determine the number of clusters in the data. For example, clusters may be determined in PCA-reduced feature space at 322. At 324, Gap statistic may be used to determine the number of clusters. The possibility that the data may not cluster at all (i.e., there is a single cluster) may not be excluded.

HFOs may be initially detected using sensors or other methods known to a person of skill in the art. Raw iEEG data may be processed on a per-channel basis. Raw iEEG data may be processed in 10-minute non-overlapping segments. In an example, data may be decimated by a factor of 12 (8th order low pass Chebyshev Type I filter, cutoff frequency of 1085 Hz, forward and reverse filtered to eliminate phase distortion), to 2713 HZ, before bandpass filtering between 100 and 500 Hz (20th order Cauer filter, forward and reverse filtered; specifications: 65 dB minimum lower/upper stop band attenuation, 0.5 dB maximum pass band ripple, 25 Hz lower/upper transition width). Filters may be designed and/or implemented using MATLAB®'s filter design toolbox (The MATHWORKS®, Natick, Mass.) for example.

Using a sliding window (e.g., 3 millisecond sliding window), a running RMS signal may be computed from the bandpass data. The RMS signal may be compared against a threshold (such as the mean of the RMS signal plus 5 standard deviations for example) and successive samples exceeding this threshold for a minimum duration of 6 milliseconds may be delimited by their upward and downward threshold crossing times. Marked events may be subject to the additional criterion that they may have at least six peaks greater than 3 standard deviations from the mean of the rectified bandpass signal. Retained events separated by less than 10 milliseconds may be merged to generate a candidate set of HFOs.

In pilot studies, it was observed that a common putative failure mode for the detector was retaining transients with amplitudes larger than the average global background signal (on which the algorithmic threshold may be based) but similar in morphology to the "local" background iEEG. The term "local" may mean the amount of time that may be displayed when screening for HFOs in raw and/or modestly filtered data (e.g., 1 second per screen with ~0.5 Hz-500 Hz bandwidth, ~1.2 kHz sampling rate, and 7 µV/mm vertical scaling, on a monitor with 1280×1024 pixel resolution). An example of these typical putative false positives is illustrated in FIG. 4.

Figure 4:
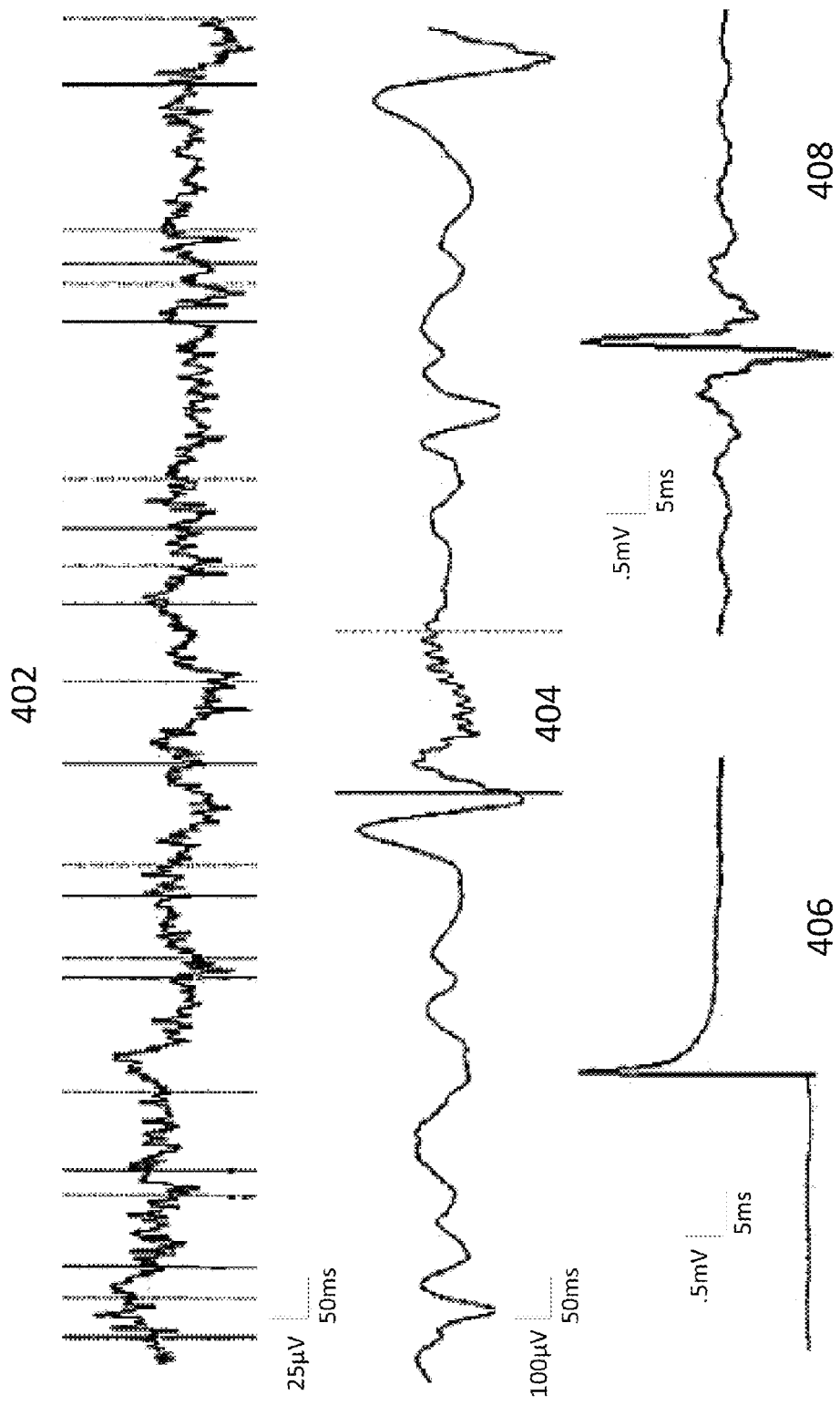
FIG. 4 shows graphs illustrating an example of putative false positives.

FIG. 4 shows examples of the lack of specificity of the stage 1 detector, which may be partial motivation for the design of stages 2 and 3. At the graph illustrated at 402, a run of putative false positive stage 1 detections are shown, none of which appear visually well distinguished from the surrounding iEEG. Individual detections are delimited by solid (start) and dotted (stop) lines. These detections may be contrasted with the single detection in the graph illustrated at 404, a putatively valid HFO. At the graph illustrated at 406, a typical sharp transient artifact is detected by stage 1; unfiltered waveform. At the graph illustrated at 408, a bandpass filtered version of the graph illustrated at 406 is shown. This filter artifact is what the stage 1 detector actually "sees," giving insight into why the event is flagged as an oscillation. The algorithm described herein is designed to discard, in stage 2 for example, events similar to those shown at 402, and to aggregate into a single cluster, in stage 3 for example, events similar to those illustrated at 406 and 408. More interesting events like that in 404 may group naturally into one or more clusters, in stage 3.

The design of the second stage of the algorithm may assume that a key aspect of an HFO's saliency for a human reading iEEG may be its relative amplitude and its spectral distinctiveness—the degree to which its morphology, as opposed to simply its size, "pops out" from the background. Stage 1 detections that fail to meet a spectral novelty criterion, as described herein, may be eliminated.

Candidate HFOs passing through stage 1 may be processed individually in stage 2, which may operate on the decimated data. To simplify notation, in equations (3.1)-(3.14) that follow, the indexing subscripts that indicate that functions and variables are specific to a particular HFO candidate have been suppressed, but these subscripts may be implicit. Twelve hundred milliseconds (after a 5 ms guard time for example) on either flank of a given candidate may be used to build a model of the local background iEEG. Background data may be segmented into clips of length that may be equal to the candidate detection. Detections exceeding 50 ms (~14%) are truncated to 50 ms to place a lower limit on the number of background segments available.

For each background segment, as well as the candidate detection itself, a linear fit may be found using least-squares regression and/or removed by subtraction (i.e., the signal may be detrended). Each segment may be energy-normalized by dividing by its Euclidean length, and a power spectral density estimate may be computed using a multitaper technique (e.g., 3 tapers; 512-point DFT (zero-padded); adaptive nonlinear combination method). The method may involve multiplying the signal by n orthogonal data tapers having optimal spectral concentration properties—discrete prolate spheroidal sequences—before computing the squared magnitude of the discrete Fourier transform in each case. This may produce η independent spectral estimates, which may be additively combined using weighting factors that may be adaptively chosen depending on local characteristics of the spectrum. Multitaper techniques may be well suited to the analysis of short duration signals, as well as signals with spectra having a large dynamic range of amplitudes, which may make them an appropriate choice for the application disclosed herein.

The local background iEEG may be modeled using a mixture of Gaussians, under the assumption that each background segment may be an observation emitted from one of a small number (one to three for example) of multivariate Gaussian components. Thus, the probability of observing any local background segment, ρ(x), may be represented by the density functions:

$$p(x) = \sum_{k=1}^{K} \pi_k \frac{1}{(2\pi)^{\frac{D}{2}} \cdot |\Sigma_k|^{\frac{1}{2}}} \exp\left\{-\frac{1}{2}(x - u_k)^T \sum_{k}^{-1} (x - u_k)\right\} \quad (3.1)$$

where x is the D×1 vector representing the background segment, κ is the number of mixture components, $\pi_k$ is the weight of the $k^{th}$ mixture component ($\Sigma_{k=1}^{k}\pi_k=1$, $\pi_k \geq 0 \forall k \in \{1, 2, \ldots, K\}$), D is the dimensionality of the data, $\Sigma_k$ is the D×D covariance matrix for the $k^{th}$ mixture component, and $u_k$ is the D×1 mean vector for the $k_{th}$ mixture component. The Gaussian Mixture Model (GMM) may be further discussion below.

An objective may be to maximize the (log) probability of the collection of background segments surrounding each candidate HFO. The background segments may be independent and/or identically distributed. This quantity viewed as a function of the model parameters—the component weights, mean vectors, and/or covariance matrices (which may be unconstrained for example)—may be known as the (log) likelihood function, and in this case may be written as:

$$\ln p(X\mid u,\Sigma,\pi)=\sum_{n=1}^{N}\ln\left\{\sum_{k=1}^{K}\pi_k N(x_n\mid u_k,\Sigma_k)\right\} \quad (3.2)$$

where X is the N×D data matrix with N the number of background segments, u is the D×K matrix of horizontally concatenated mean vectors; Σ is the D×(D·K) matrix of horizontally concatenated covariance matrices, π is the 1×K vector of component weights, and N(•) is the multivariate normal distribution (shown uncollapsed in equation (3.1), above—the expression to the right of $\pi_k$).

Maximization may be performed using the Expectation Maximization (EM) algorithm, which may be a two stage iterative numerical procedure. Initial component weights may be set equal to each other (i.e.

$$\pi_k = \frac{1}{K}$$

for each k) and/or mean vectors and covariance matrices may be initialized using the k-means algorithm. The EM update steps, which may result in an increase in the log-likelihood with each iteration, may be performed as follows:

$$\text{E-Step: } \gamma^{(t)}(z_{nk}) = \frac{\pi_k^{(t)} N\left(x_n\mid u_k^{(t)}, \sum_k^{(t)}\right)}{\sum_{j=1}^{K}\pi_j^{(t)} N\left(x_n\mid u_j^{(t)}, \sum_j^{(t)}\right)} \quad (3.3)$$

$$\text{M-Step: } u_k^{(t+1)} = \frac{1}{N_k}\sum_{n=1}^{N}\gamma^{(t)}(z_{nk})x_n \quad (3.4)$$

$$\sum_k^{(t+1)} = \frac{1}{N_k}\sum_{n=1}^{N}\gamma^{(t)}(z_{nk})(x_n - u_k^{(t+1)})(x_n - u_k^{(t+1)})^T \quad (3.5)$$

$$\pi_k^{(t+1)} = \frac{N_k}{N} \quad (3.6)$$

where $$N_k = \sum_{n=1}^{N}\gamma^{(t)}(z_{nk}) \quad (3.7)$$

Note that z is K-dimensional random variable (which may be called a "latent" variable because it may not be explicitly observed) having K possible states, such that whenever a particular element is equal to 1, all others may be equal to zero. Its marginal distribution may be defined in terms of the mixture component weights, such that p ($z_k$=1)=$\pi_k$. It may be introduced in order to achieve a formulation of the likelihood function that is amenable to maximization using EM. $\gamma(z_{nk})$ may be defined as the posterior probability that $z_k$=1 given that data segment $x_n$ has been observed, or, mare colloquially, the probability that mixture component k is "responsible" for generating observation $x_n$. The EM algorithm may allow discovery of the parameters of the model from the data. When it converges, it may converge to at least a local maximum of the likelihood functions. The algorithm may have converged when successive computed values of the likelihood function differ by less than or equal to 1×10$^{-5}$. In cases where numerical issues may arise or where convergence may not be achieved within a pre-specified number of iterations (500), either due to encountering singularities of the likelihood function or to otherwise slow rates of convergence for example, the algorithm may return an "indeterminate" flag, and the HFO candidate in question may pass to the third stage of processing without interruption of the program flow.

Given the small number of background segments relative to the dimension of the data, to combat the curse of dimensionality the number of dimensions of each background segment and/or the candidate segment may be reduced to two (i.e., D=2), prior to learning the Gaussian Mixture Model (GMM). This may be done using principal components analysis (PCA) on the frequency-domain representations of the background segments discussed above, such as after removing the mean and dividing by the standard deviation of the background segments for example.

The principal components may be found by successively seeking out the spatial directions along which the lengths of the orthogonal projections of the data observations have maximal variance, subject to the constraint that each successive direction may be orthogonal to its predecessors. These directions are the eigenvectors of the covariance matrix, C, of the data:

$$C = \frac{1}{N}\sum_{n=1}^{N}(b_n - \bar{b})(b_n - \bar{b})^T \quad (3.8)$$

where $b_n$ is the P×1 power spectral density representation of background segment n, described above, and b is the mean of all N background segments associated with a given HFO candidate (for us, b=0). Since the number of background segments is smaller than their dimensionality, P, the data may lie in a linear subspace whose maximum dimension is N−1. Therefore, at least P−N+1 eigenvalues (projection variances) may be zero, and this may be used to increase the efficiency with which the relevant eigendecomposition may be performed. The coordinates for each background data segment may be computed as:

$$X=BU \quad (3.9)$$

where X is the N×D data matrix of background-segment representations, B is the N×P matrix whose $i^{th}$ row is $b_i^T$, and U is the P×D matrix whose columns are the unit-normalized eigenvectors of C corresponding to the D largest eigenvalues (according to one example, D=2, as described above). The D-dimensional projection for the HFO candidate segment itself may be computed, such as after the mean of the background segments is removed and dividing by their standard deviation, using the same matrix U.

Since there may be no a priori reason to prefer a specific number of mixture components in the GMM (indeed, use of a GMM itself may represent an assumption, such as an assumption about the appropriate model form for example), the parameters for i=1, 2, and 3 component mixtures may be learned, and the Bayesian Information Criterion (BIC) may be used to make the final model selection. The BIC, like other common information criteria (e.g., Akaike's), may include a term that penalizes a model's complexity. It may be used to guard against overfitting; that may be to adjust for increases in the data likelihood that may occur by virtue of having enough parameters to enable precise tuning to the data set at hand, which may presumably be one sample from the space of each of the data sets generable by the process being modeled. The BIC may be derived starting from the Laplace approximation to the "model evidence"—the probability of the data given a particular model after marginalizing over all possible values of the parameters. With some nontrivial assumptions—namely, a) a broad (nearly uniform) Gaussian prior distribution over the parameters; and/or b) a Hessian matrix of the negative log-likelihood function (e.g., evaluated at the optimal parameter vector given the data) that may be of full rank—the evidence for the $i^{th}$ model ($M^i$), denoted by $p(X|M^i)$, may be approximated by:

$$\ln p(X | M^i) \approx \ln p(X | u^i_{ML}, \Sigma^i_{ML}, \pi^i_{ML}) - \frac{1}{2} M^i \ln N \quad (3.10)$$

where the subscript ML stands for the "maximum likelihood" estimates found via EM, and the constant $M^i$ in the second term on the right is the number of free parameters in the $i^{th}$ model. The computation in equation (3.10) is the Bayesian Information Criterion, and the model for which it is largest may be selected.

The goal in stage 2 may be to assign a given HFO candidate to at least one of two classes (e.g., B (background) or A (anomaly)), while the misclassification rate may be minimized. This may be done by assigning h to B whenever $$p(\beta|h) > p(A|h) \quad (3.11),$$

where h is the 2-D representation of the HFO candidate, discussed above. Applying Bayes's Theorem, this condition may be shown to be equivalent to $$p(h|\beta) > \frac{p(h|A)p(A)}{p(\beta)} \quad (3.12)$$

The GMM describing B may allow estimation of the quantity on the left directly, but there may be no such model for A and one may not reasonably be inferred given that there may be at most a single observation from A. The prior probabilities of A and B, respectively, are similarly unknown.

To address these issues a heuristic criterion may be used, which may be based on the squared Mahalanobis distances, $\Delta_k^2$, from the FIFO candidate to the center of each GMM component:

$$\Delta_k^2 = (h - u_k)^T \Sigma_k^{-1} (h - u_k) \quad (3.13)$$

The squared Mahalanobis distances of a random sample drawn from a multivariate normal distribution (which may be computed using the unbiased sample covariance matrix for example) may be distributed approximately as central chi-squared with D degrees of freedom, where D is the dimensionality of the data. Using the assumption that p(h|A) is a monotonic decreasing function of p(h|B), so that the latter is high wherever the former is low, it may be estimated that:

$$p(\beta|\Delta_1^2, \ldots, \Delta_K^2) \approx \sum_{k=1}^{K} \pi_k \int_{\Delta_k^2}^{\infty} q(t)dt \quad (3.14)$$

where q(x) is the central chi-squared density function with v degrees of freedom:

$$q(x) = \begin{cases} \frac{1}{2^{\frac{v}{2}} \Gamma(\frac{v}{2})} x^{\frac{v}{2}-1} \exp\left(-\frac{1}{2}x\right) & x > 0 \\ 0 & x < 0 \end{cases} \quad (3.15)$$

The function $\Gamma(z)$ is the Gamma function, $\Gamma(z) = \int_0^\infty t^{z-1} \exp(-t) dt$ Procedurally, the percentage of the central chi-squared density lying to the right of the calculated Mahalanobis distance from each mixture component may be found. A weighted average of these percentages, with weights equal to those of the corresponding mixture components may be computed. If the resultant estimated probability exceeds 5%, the HFO candidate may be considered to have been generated by the local background process and it may be removed from candidacy. The candidates for which the calculation in equation (3.14), which may be computed with respect to the candidate's unique local background model, falls below the 5% threshold may be passed on to the final clustering stage.

Figure 5:
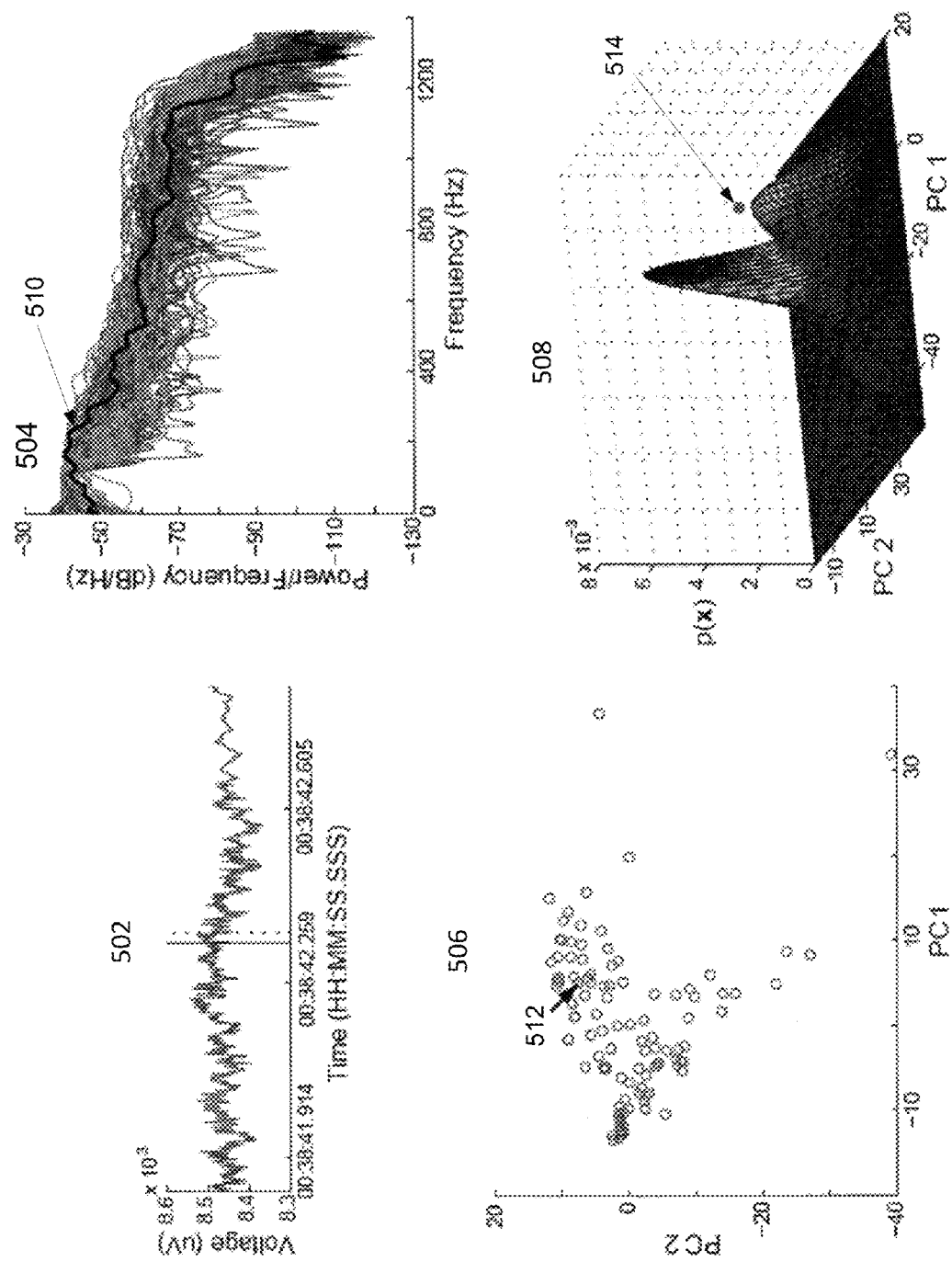
FIG. 5 provides graphical depictions of stage 2 of the algorithm described herein and illustrates an event that is not passed on to stage 3.
Figure 6:
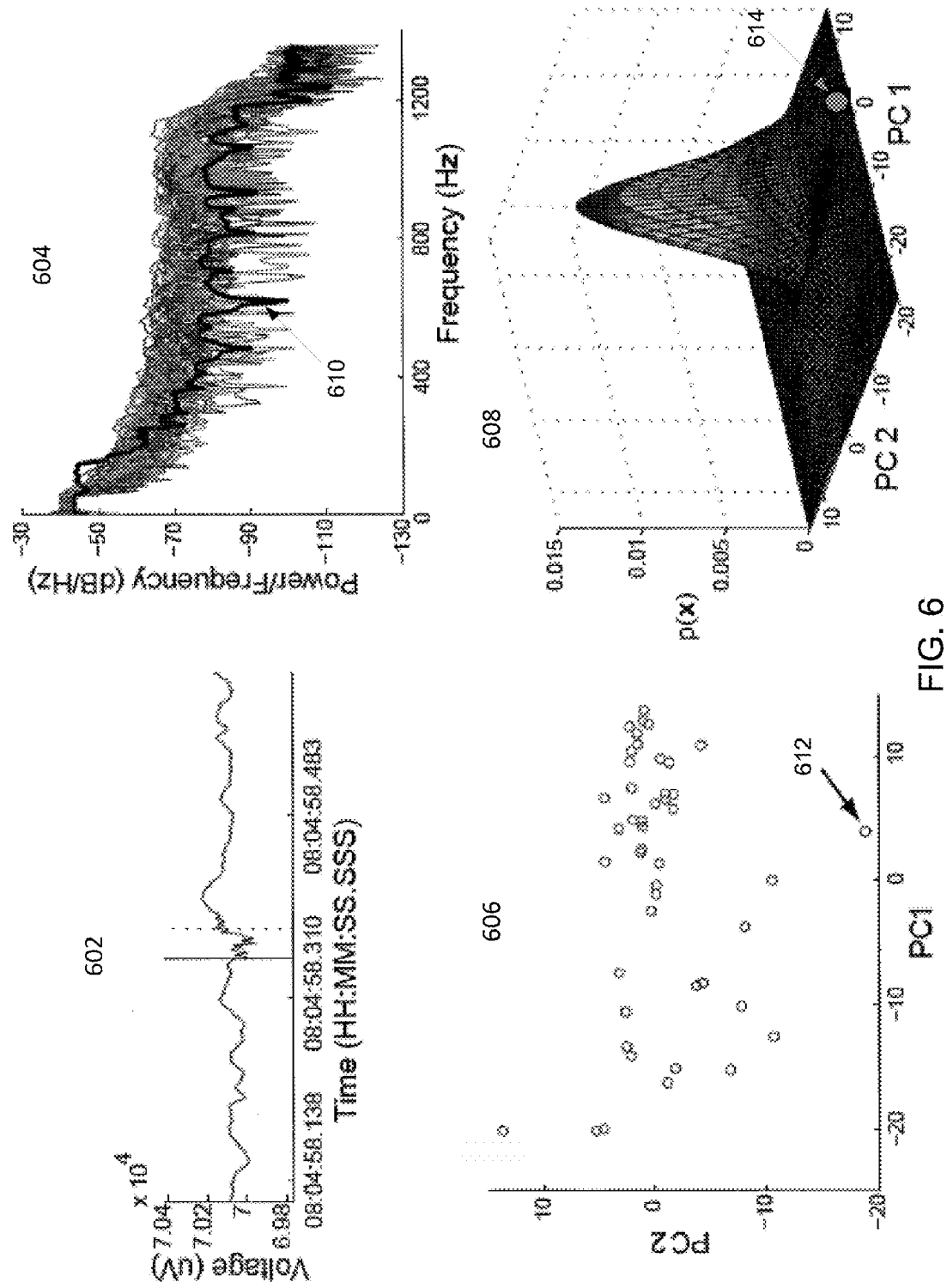
FIG. 6 provides graphical depictions of stage 2 of the algorithm described herein and illustrates an event that is passed on to stage 3.

FIGS. 5 and 6 provide graphical depictions of events of stage 2. FIG. 5 shows an event that was removed from candidacy. FIG. 6 shows an event that was passed on to stage 3.

FIG. 5, at graph 502, shows a putative false positive detection, delimited by vertical lines. Graph 504 illustrates multitaper power spectral density estimates (line 510) of the detection in graph 502 and of the signals obtained by segmenting the data flanking the detection (the lines surrounding line 510). Line 510 falls within the "envelope" of the background spectra. Graph 506 illustrates projections (illustrated as points) of the background spectra in graph 504 onto the plane defined by their first two principal components, along with the projection of the detection (point 512). Graph 508 illustrates a three-component Gaussian mixture model learned from the background data in graph 506. Here the detection is shown as point 514 and elevated above the density function to facilitate visualization. The test detailed herein indicates that the detection is likely to have been generated from the background process described by the mixture model, and the detection may be discarded from candidacy.

FIG. 6, at graph 602, shows a putative valid detection, delimited by vertical lines. Graph 604 illustrates multitaper power spectral density estimates (line 610) of the detection in graph 602 and of the signals obtained by segmenting the data flanking the detection in the manner described herein (the lines surrounding line 610). Line 610 (in particular the values lying between roughly 100 and 200 Hz) falls outside the "envelope" of the background spectra. Graph 606 illustrates projections (illustrated as points) of the background spectra in graph 604 onto the plane defined by their first two principal components, along with the projection of the detection (point 612). Graph 608 illustrates a two-component Gaussian mixture model learned from the background data in graph 606. Here the detection is shown as point 614 to facilitate visualization. The test detailed herein indicates that the detection is unlikely to have been generated from the background process described by the mixture model, and the detection may be passed on to stage 3 for clustering.

Before clustering, features may be computed on the data corresponding to each event passing through stage 2. The features may be designed and/or chosen with at least one of two goals in mind: 1) permit separation of "ripples" and "fast ripples," should there indeed be evidence for such compartmentalization (and not otherwise); and/or 2) aggregate highly stereotypical, sharp transient recording artifacts that were observed in pilot studies (illustrated in graphs 506,606 and

508,608 in FIGS. 5 and 6). Features in category 1 were conceived a priori (blinded to patient data), while features in category 2 were developed and refined using labeled artifacts from two patients. The set of feature vectors $\{F_1, \ldots F_I\}$, where I is the total number of anomalies passing through stage 2 (in our case, I=290, 273), may be the data set that is clustered.

Clustering may be accomplished using a variant of the k-means algorithm. The k-means algorithm seeks to minimize the quantity:

$$W_K = \sum_{k=1}^{K} \frac{1}{2N_k} \sum_{i,i' \in C_k} d_{ii'} \quad (3.16)$$

where K is the number of clusters, $C_k$ denotes the set of indices of the observations in cluster k, (with each observation assigned to a single cluster), and $N_k$ denotes the number of observations in cluster k. $d_{ii'}$ is the squared Euclidean distance between P-dimensional observations $x_i$ and $x_{i'}$:

$$d_{ii'} = \sum_{p=1}^{P} (x_{ip} - x_{i'p})^2 = \|(x_i - x_{i'})\|^2 \quad (3.17)$$

The quantity $W_K$ in equation (3.16) may be viewed as a modified version of the within-cluster point scatter in which each cluster's contribution may be weighted inversely by its membership. Thus, diffuse clusters with few members may not be counted as energetically favorably as compact clusters with many. Minimizing this metric is exactly equivalent to minimizing the pooled within-cluster sum of squared distances from the cluster means (centroids), so that $W_K$ may alternatively be written as (with the technically inert factor of 2 in the denominator of equation (3.16) achieving this equivalence):

$$W_K = \sum_{k=1}^{K} \sum_{i \in C_k} \|X_i - \overline{X}_k\|^2 \quad (3.18)$$

where $\overline{X}_K$ is the mean of the elements in cluster k. An iterative descent algorithm for minimizing the above criterion may be obtained by defining clusters via prototypes $\{u_k\}_{k=1}^{K}$ and/or attempting to minimize, over parameters u and Y, the error function:

$$\in_K (u, Y) = \sum_{ki} Y_{ki} \|x_i - u_k\|^2 \quad (3.19)$$

where u is the P×K matrix of prototypes and Y is a K×I indicator matrix of cluster assignments, with/the total number of data observations. That is, $Y_{ki}=1$ whenever $x_i$ is assigned to cluster k, and 0 otherwise. The algorithm may proceed as follows: (1) Initialize u randomly. Randomly chosen k observations from the data set, X is used. (2) For each $x_i$, compute the nearest prototype.

$$set Y_{ki} = \begin{cases} 1 & \text{if } k = \arg\min_j \|u_j - x_i\|^2 \\ 0 & \text{otherwise} \end{cases} \quad (3.20)$$

(3) Recompute cluster prototypes.

$$set\ u_k = \frac{\sum_i Y_{ki} x_i}{\sum_i Y_{ki}} \quad (3.21)$$

(4) Return to step 2 and repeat until convergence.

As step 2 may minimize the error function with respect to Y and step 3 may minimize the error function with respect to u, $\in$ may decrease with each iteration so that convergence—to a local minimum, at least—may be assured.

Instead of using the L2 norm (Euclidean distance), the classification scheme may use the L1 norm (Manhattan distance) as distance metric, which may yield the k-mediods algorithm. In step two of the algorithm (using equation 3.20), a given point may be assigned to the prototype that is closest in the L1 sense, and in step three (using equation 3.21) the appropriate minimization may be obtained by computing the method, rather than the centroid, for each newly formed cluster. The k-mediods method may be used to achieve a clustering that is more robust against outliers than k-means, but may be at computational expense.

Above, W has been subscripted with "K," the number of clusters, to emphasize that the k-means and k-mediods algorithms may require that the number of clusters in the data be pre-specified. This may be a limitation in some situations, in which the number of clusters, such as "types" of anomalous events passing through stage 2 for example, may be a priori unknown, and may itself be a major goal of the exploratory analysis.

$W_k$ is a monotonically decreasing function of k. This may be intuited by considering the progression to the extreme case, in which each observation may constitute its own cluster and hence $W_k$ may be equal to zero. Plots of $W_k$ versus k may show a characteristic "elbow point," a value for k at which previously large decreases in the function may become markedly flattened. This point may be taken to represent the transition between decreases that represent an evolution toward the data's true underlying structure and decreases that are simply attributable to the inevitably greater compactness of clusters that may be achieved by adding more cluster centroids. This elbow value of k may be taken as the "optimal" number of clusters.

The optimal number of clusters in a data set may be estimated given a similarity metric and error measure, and present a statistical procedure to formalize the elbow heuristic concept described above. For example, the graph of $\log(W_k)$ versus k may be compared with its expectation, $E_I^*[\log(W_k)]$, under a suitable null reference distribution of the data. They define the gap statistic for sample size I, $G_I(k)$, as:

$$G_I(k) = E_I^*[\log(W_k)] - \log(W_k) \quad (3.22)$$

and propose to choose the optimal k as that for which the gap statistic is largest after taking its sampling distribution into account. The null model assumed is a single component model, and the statistical procedure is designed to reject it in favor of a k-component model (k>1), if the strongest evidence for any such k under consideration merits it. The choice of the number of k's over which to probe may vary. A uniform distribution over a box aligned with the principal components of the data may be used as the form of the single-component reference distribution.

The clustering procedure may begin with the data set $\{\hat{F}_1, \ldots, \hat{F}_I\}$—the reduced feature-vector representations of anomalies 1 through I that have passed through stage 2. For number-of-cluster values k=1 through 20, the k-mediods algorithm may be run using 10 random initializations, and the run that yields the lowest $\log(W_k)$ may be chosen for each k. Then, again for each k, an expected value for $\log(W_k)$ under the null reference may be computed, using 20 reference data sets for each value of k for example. A given reference set may be created by performing a PCA rotation of the data, sampling I vectors uniformly over the range of values along each dimension, and then back-rotating the samples into the original coordinate frame. Each reference set may be clustered in an identical manner to the true data set, and the expected value for each $\log(W_k)$ may be taken as the average over the reference sets. A corrected standard deviation, $s_k$, that accounts for the simulation error may be computed as:

$$s_k = sd_k\sqrt{1 + \frac{1}{B}} \qquad (3.23)$$

where $sd_k$ is the standard deviation and B is the number of reference sets (e.g., 20 reference sets as described in example embodiments herein). Taken as the optimal clustering of the data may be that which meets the following criterion:

$$\hat{k} = \min\{k | \mathrm{Gap}(k) \geq \mathrm{Gap}(k+1) - s_{k+1}\} \qquad (3.24)$$

where $\hat{k}$ is the estimated optimal number of clusters. If the above set were empty, $\hat{k}$ may be set equal to the largest value tested, which in this case may be 20 for example.

According to one example, the number of channels and total number of iEEG hours processed per subject are shown in table 3.1. The total iEEG hours is the sum over the channels of the length of time recorded for each channel. Across eleven subjects, a total of 1,423,741 HFO candidates, were detected in stage 1. The summed duration of stage 1 detections was 13.7 hours, or 0.04% of the total data processed, giving an indication of the rarity of stage 1 detections. Among these stage 1 candidates, 290,273 (~20%) were flagged as anomalous events in stage 2, and passed on to stage 3 for clustering. To verify that the stage 2 anomaly detection algorithm was not performing the trivial task, of taking a random subsample of post stage 1 events, the null hypothesis was tested that the proportion of events retained after stage 2 was the same for all patients, finding, as expected, evidence to reject it ($x^2(10, N=1,423,741)=57,088.23$, $p<<<0.0001$).

Four clusters were found in stage 3 by the k-mediod/gap-statistic method. The

TABLE 3.1

Raw data summary

Figure 7:
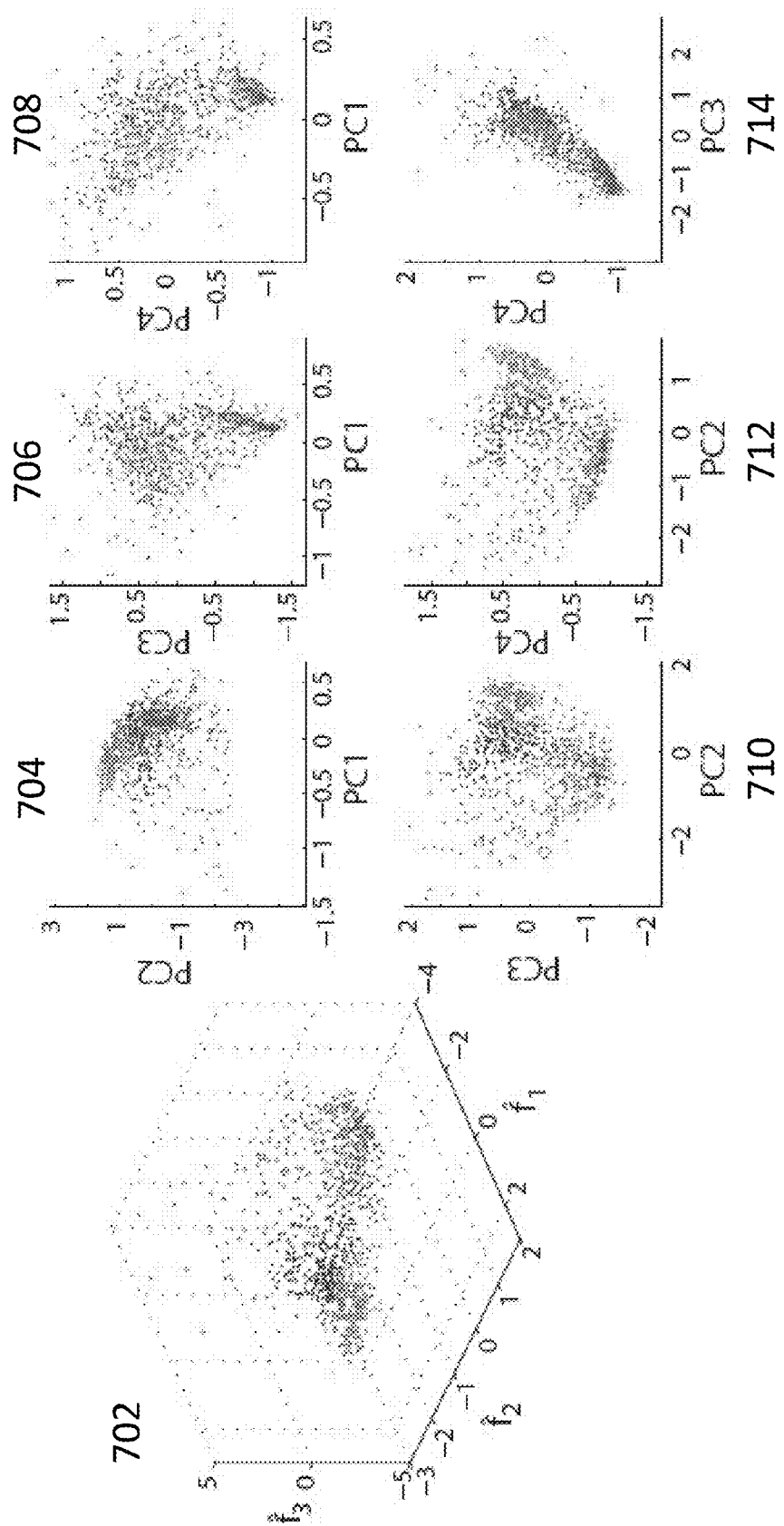
FIG. 7 is a graphical illustration of the results of clustering of 1000 randomly selected events passing through stage 2 of the algorithm described herein.
Figure 8:
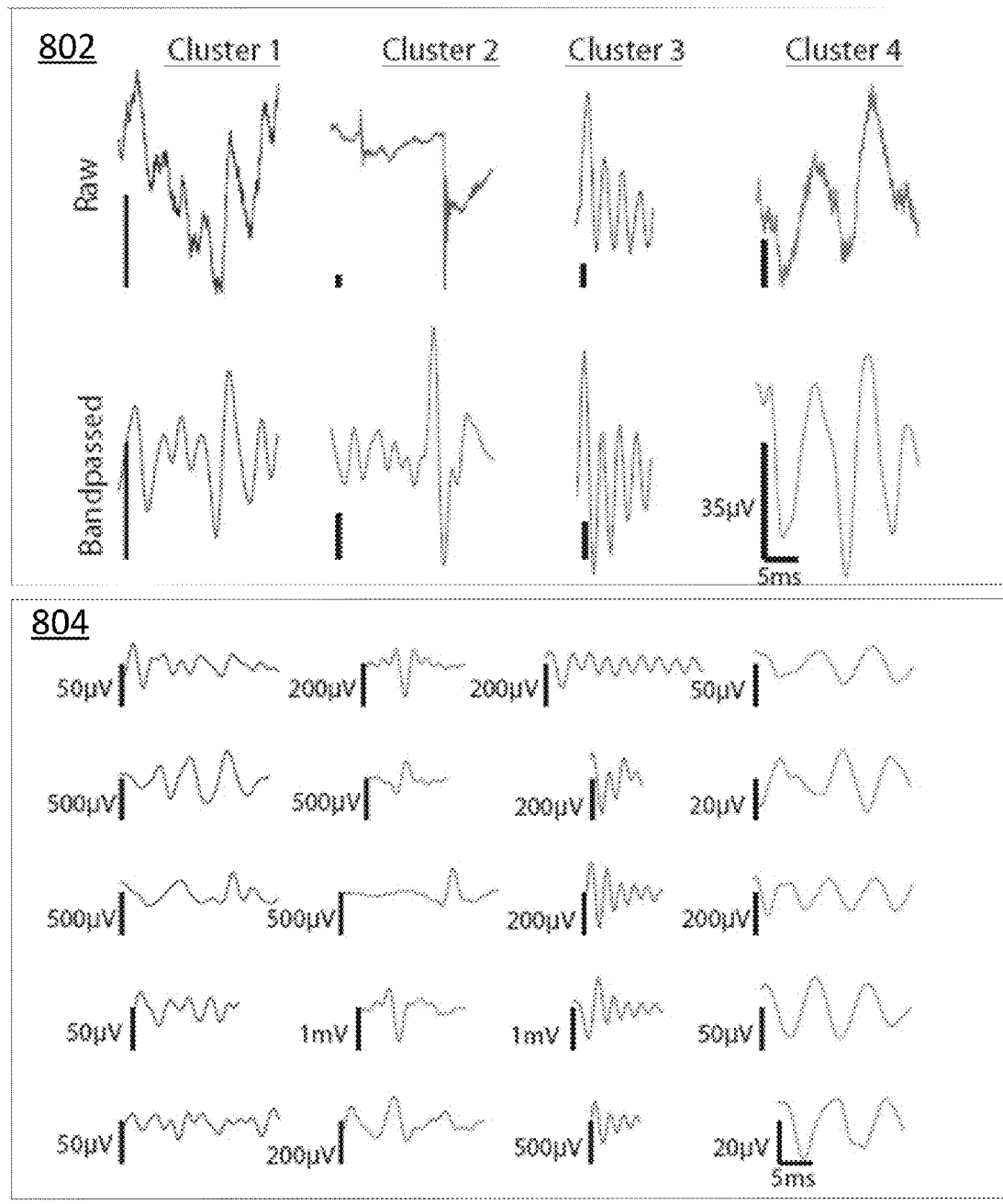
FIG. 8 shows the cluster prototypes for each of the clusters found by applying the algorithm described herein.

| Subject | # Channels | Total iEEG Hrs |
|---|---|---|
| CT 01 | 144 | 1176 |
| CT 02 | 128 | 1877 |
| SZ 01 | 45 | 480 |
| SZ 02 | 126 | 1890 |
| SZ 03 | 69 | 977 |
| SZ 04 | 90 | 2122 |
| SZ 05 | 84 | 5460 |
| SZ 06 | 115 | 10139 |
| SZ 07 | 86 | 5615 |
| SZ 08 | 104 | 812 |
| SZ 09 | 110 | 735 |
| 11 subjects | (1101) | (31283) | results of clustering are illustrated in FIGS. 7 and 8.

FIG. 7, at graph 702, shows a clustering of 1,000 events selected randomly across a number of patients, passing through stage 2, plotted in the space defined by $\hat{f}_1$, $\hat{f}_2$, and $\hat{f}_3$ and according to class label. Each of the four clusters found in the algorithm is colored uniquely. FIG. 7, at graphs 704-714, gives an alternative view of the clustering, projecting the points onto the planes defined by all possible pairs of principle components. The points on the left are projected on to all possible pairs of principal components; axes are scaled to enable better visualization of cluster boundaries, so a small number of outlying points are not visible. Distinct boundaries are apparent between the red, the green, and the blue clusters taken together, while the separation between the light and dark blue clusters is less marked.

FIG. 8 shows the cluster prototypes for each of the four clusters found by applying the algorithm described herein to the 290,273 events passing through stage 2. The prototypes are found by computing the class members nearest (in the Mahalanobis sense) to the cluster mediods in feature space. In FIG. 8, at graph 802, both the raw (top) and the 100-500 Hz bandpass filtered (bottom) detection for each prototype are displayed. At graph 802, vertical scale bars are 35 μV in all cases. In FIG. 8, at graph 804, five randomly selected members (bandpass waveforms) from each cluster are shown. In both graph 802 and graph 804, events may be truncated to 25 ms to put each waveform on the same time scale for easier comparison.

Qualitatively speaking, cluster 1 (n=70, 671) is comprised of irregular, mixed-frequency events; cluster 2 (n=92, 744) is comprised of sharp-rising transients that appear to be artifacts (i.e. whose oscillatory characteristics come from filtering the sharp rise); cluster 3 (n=38, 945) is comprised of fast, regular waveforms of relatively pure frequency; and cluster 4 (n=87, 913) is comprised of slow, regular waveforms of relatively pure frequency.

To investigate the stability of the clustering algorithm and test whether the aggregated clustering results shown in FIGS. 7 and 8 were influenced by individual subjects, two additional experiments were performed.

Figure 9:
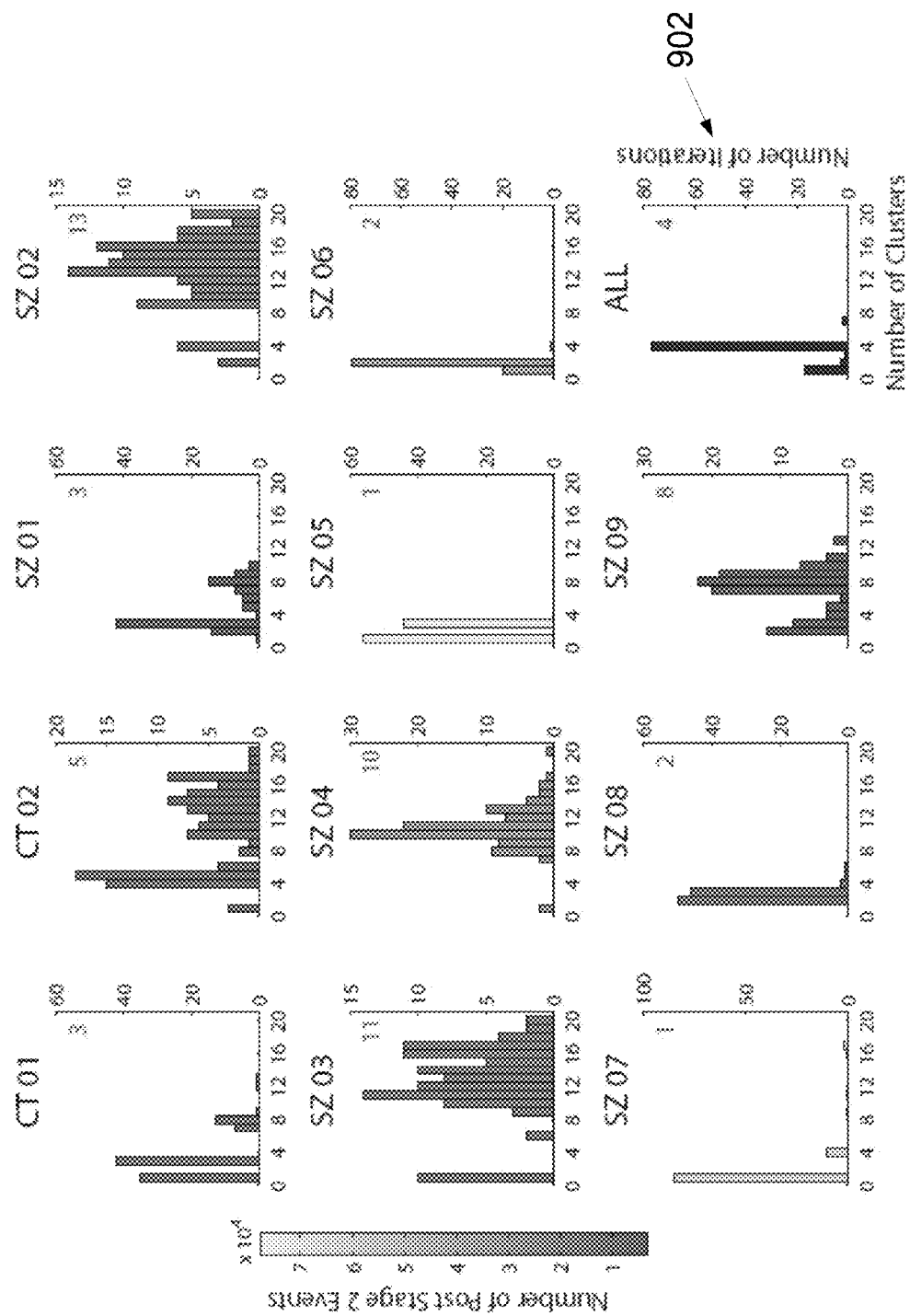
FIG. 9 is a graphical illustration summarizing the outcome of a 100-iteration sampling experiment described herein.

In the first, the clustering algorithm was applied to individual subjects by clustering 100 random samples drawn from the set of events passing through stage 2 for each subject. The size of each of the 100 random samples was 25% of all the subject's post stage 2 events. Results are shown in FIG. 9, which contains one panel for each patient: a histogram summarizing the outcome of the 100-iteration sampling experiment. As shown in FIG. 9, the number of clusters found by the algorithm is plotted on the x-axis, while the number of iterations is plotted on the y-axis. The lower right panel (graph 902) of FIG. 9 represents the results of a similar random sampling experiment performed on the data aggregated across subjects, with the difference being that sample sizes of 5% (15,000 of all 290,273 events passing through stage 2 across all subjects) were used. Each individual subject's histogram is shaded in proportion to the relative number of events passing through stage 2 for that subject. Thus, the shade of the histogram reflects the weight of the subject's contribution to each of the 100 random samples represented in the aggregate histogram in the lower right panel (graph 902). The number in the upper right-hand corner of each graph indicates the mode of the distribution, which may be interpreted as the number of clusters the algorithm yields for that patient. The degree of concentration of the distribution for a given individual reflects the stability of the algorithm for that subject, which may be a function of the variability and shape of the subject's events in feature space, as well as the sample size clustered.

Figure 10:
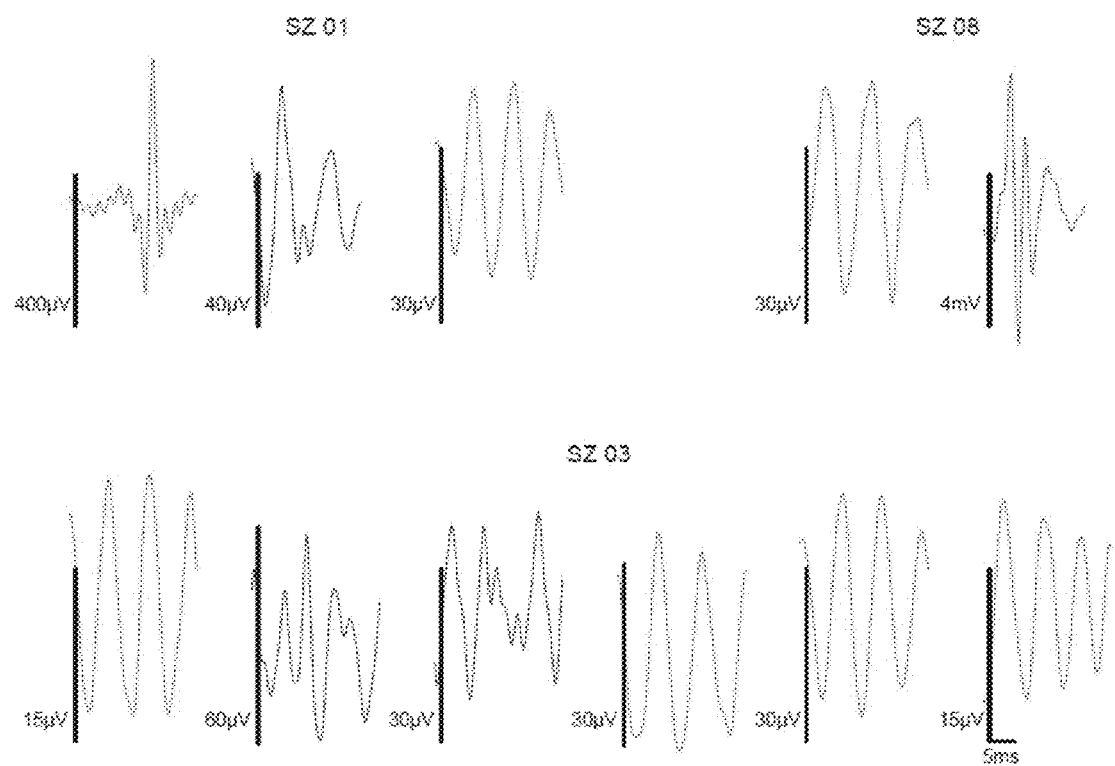
FIG. 10 illustrates example prototypes from individual subject clustering, in 100-500 Hz bandpassed waveforms.

In the six of eleven subjects for whom the algorithm yielded four or fewer clusters (graphs CT 01, SZ 01, SZ 05, SZ 06, SZ 07, and SZ 08) the clusters appeared to be subsets of those found in the aggregated data. In the remaining five subjects (graphs CT02, SZ 02, SZ 03, SZ 04, and SZ 09) for whom there were greater than four clusters, the additional clusters appeared to have resulted from over-splitting some combination of the four clusters found in the aggregated data. These trends are illustrated in FIG. 10, which shows examples of prototypes derived from clustering individual subject data. Prototypes in FIG. 10 are given a color corresponding to the aggregate prototype to which they bear the closest visual resemblance (such as in FIG. 8, at 802, in the bottom set of waveforms for example).

FIG. 10 shows example prototypes from individual subject clustering, in 100-500 Hz bandpassed waveforms. Events are truncated to 25 ms to put each waveform on the same time scale for easier comparison. Subjects illustrated in graph SZ 01 and graph SZ 08 show clusters that appear to be subsets of the four clusters found in the aggregate. Subject illustrated in graph SZ 03 does as well, but in this case two groups have been oversplit by the algorithm, yielding six clusters. The latter type of cluster stability was not seen in the aggregate clustering.

The subject illustrated in graph SZ 01, for whom the algorithm yields strong evidence for three clusters, appears to exhibit the artifact, mixed, and slow oscillation clusters, but not the fast oscillations of the aggregated clustering. The subject illustrated in graph SZ 08, for whom the algorithm weakly suggests two (over three) clusters, exhibits the artifact and slow oscillation clusters prominently. The subject illustrated in graph SZ 03, for whom the algorithm performs relatively poorly, also appears to have clusters that are a subset of those found in the aggregate—namely, the mixed frequency and slow oscillation clusters—but they are often highly split by the algorithm. FIG. 10 shows one iteration in which six clusters were obtained from what appears to be these two.

To quantify these observations about the stability of the algorithm, Rand's c-statistic (Rand's index) may be used as a measure of agreement between two partitionings of a data set. Rand's index is the fraction of the pairs of observations that are treated similarly in both partitionings, where a "similarly treated" pair is one whose members either are in the same cluster or in different clusters in both partitionings:

$$c = \frac{\binom{N}{2} - \left[\frac{1}{2}\left\{\sum_{k=1}^{K}\left(\sum_{k'=1}^{K'} n_{kk'}\right)^2 + \sum_{k'=1}^{K'}\left(\sum_{k=1}^{K} n_{kk'}\right)^2\right\} - \sum_{k=1}^{K}\sum_{k'=1}^{K'} n_{kk'}^2\right]}{\binom{N}{2}} \quad (3.25)$$

K is the number of clusters in the first partitioning, K' is the number of clusters in the second partitioning, and $n_{kk'}$ is the number of observations that were simultaneously in cluster k in the first partitioning and cluster k' in the second partitioning. Being a proportion, Rand's index varies between zero, when no pairs are treated similarly by the two clusterings, and one, when the clusterings are identical.

The similarity of one partitioning to another was determined, within a subject, for iterations on which the algorithm returned more than a single cluster. Because each of the 100 clusterings for a given subject was based on an independent random sample, the samples upon which any two clusterings were based contained some non-overlapping observations. As the Rand index has nothing to say with regard to such unique observations, the intersection of the two clustered samples was considered. For each individual subject, as well as for the aggregated clustering, Rand's index for the pairs of clusterings was computed in which both numbers of clusters were greater than 1. Results are shown in table 3.2. In table 3.2, Rand's c-statistic (Rand's index) is indicated for all pairs of clusterings in which (K,K')>1 (columns 2-5). Shown for each subject are the mean $\bar{c}$, standard deviation sd, size of the sample (i.e. number of clustering pairs) upon which the mean was based, n, and the average number of overlapping data observations in each pair of samples, $\bar{s}$. A value of 1 for any given $\bar{c}$ would indicate a perfect match between all n pairs of clusterings. Columns 6 and 7, included for reference, give the mean value for the Rand index when all 100-choose-2 (4950) pairs of clusterings are considered and its standard deviation, respectively. The average number of overlapping data observations in this case is so close to the value in column 5 (i.e. ±1 observation, typically less) for all subjects that it has not been replicated. For completeness, results are shown for when the condition (K, K')>1 is removed. The latter result may be more interesting if, in cases where more than one cluster was found, the algorithm had a tendency to produce one large cluster along with several small clusters. However, since this was not observed, the (K, K')>1 case may be most relevant.

The high values of $\bar{c}$ in the second column of table 3.2 (and the accompanying low standard deviations in column 3) indicate that in cases where the algorithm returns a number of clusters greater than 1 on different iterations, the clusterings tend to have considerable agreement. This is consistent with the idea that the number-of-cluster-variability for individual subjects comes largely from the bulk splitting and merging of the clusters that were found in the aggregate. The results in table 3.2 may not be overstated. For example, in one embodiment, any multi-cluster result for subject SZ 05 may not be taken seriously despite its "high marks" in columns two and three of the table because the preponderance of its clustering results, as seen in FIG. 9, point toward a single cluster. The low value for n in column three and the data in the last two columns of table 3.2 may serve as a reminder of this. As an alternative to the Rand index, which ranges from zero to one, one may compute the adjusted Rand index. The latter may assume a larger range of values and may be zero when the agreement between two partitionings is equal to its expectation under a chance model (i.e. each partitioning may be picked at random from the set of the partitionings having the same number of clusters and members per cluster as the original). The average adjusted Rand indices for (K, K')>1 in this case take values from 0.5-0.9, from which it may be concluded that the similarities observed are substantially greater than may be expected by chance.

TABLE 3.2

Rand's c-statistic

| Subject | $\bar{c}$ | Sd | n | $\bar{s}$ | $\bar{c}_{(n=4950)}$ | $sd_{(n=4950)}$ |
|---|---|---|---|---|---|---|
| CT 01 | 0.843 | 0.114 | 2080 | 923.280 | 0.610 | 0.314 |
| CT 02 | 0.873 | 0.060 | 4656 | 787.340 | 0.830 | 0.182 |
| SZ 01 | 0.787 | 0.129 | 4851 | 203.597 | 0.778 | 0.146 |

TABLE 3.2-continued

| | Rand's c-statistic | | | | | |
|---|---|---|---|---|---|---|
| Subject | $\bar{c}$ | Sd | n | $\bar{s}$ | $\bar{c}_{(n=4950)}$ | $sd_{(n=4950)}$ |
| SZ 02 | 0.893 | 0.092 | 4950 | 1102.662 | 0.894 | 0.092 |
| SZ 03 | 0.936 | 0.020 | 4005 | 1139.078 | 0.782 | 0.329 |
| SZ 04 | 0.923 | 0.024 | 4753 | 1825.557 | 0.891 | 0.159 |
| SZ 05 | 0.995 | 0.002 | 946 | 4856.309 | 0.670 | 0.329 |
| SZ 06 | 0.935 | 0.054 | 3160 | 2266.261 | 0.797 | 0.209 |
| SZ 07 | 0.895 | 0.085 | 105 | 3919.238 | 0.793 | 0.350 |
| SZ 08 | 0.934 | 0.054 | 4950 | 885.499 | 0.934 | 0.054 |
| SZ 09 | 0.843 | 0.114 | 4950 | 240.703 | 0.843 | 0.115 |
| ALL | 0.950 | 0.074 | 3403 | 774.617 | 0.760 | 0.311 |

Despite the expectedly variable stability on the individual, subject, data apparent in FIG. 9, the algorithm performs robustly on the aggregated data (graph 902), as well as on most patients for whom a relatively large number of events were clustered. Seventy-seven percent of the clustering iterations performed on the aggregated data yielded four clusters. Columns two and three of table 3.2 (last row) show that, furthermore, these 4-cluster partitionings were highly similar to one another.

Figure 11:
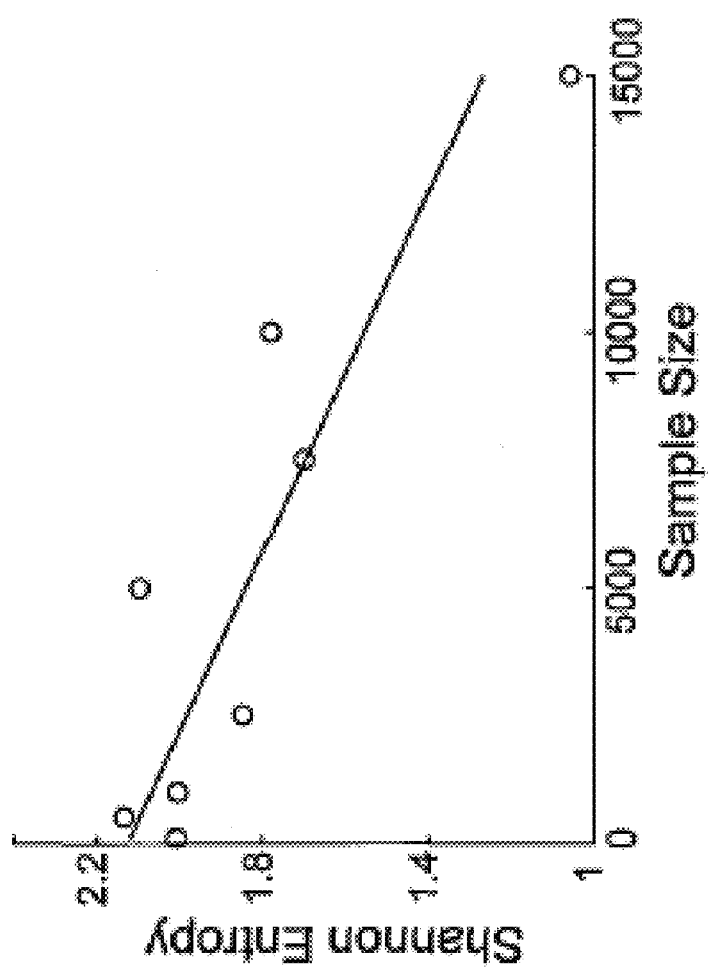
FIG. 11 is a graph illustrating a scatter plot of sample size versus the Shannon entropy of the distribution of a number of clusters.

FIG. 11 is a graph illustrating a scatter plot of sample size versus the Shannon entropy of the distribution of the number of clusters returned by the algorithm for the aggregated data. Distributions were formed at each sample size by making 100 random draws from all post-stage 2 detections. Equation for the regression line is $y=-5.71 \times 10^{-5} \chi + 2.12$.

As illustrated in FIG. 11, Shannon entropy decreases with sample size for the aggregated data. Shannon entropy, S, is defined as $S=-\Sigma_i p_i \log_2 p_i$, where $p_i$ is the probability of being in state i and $P \log_2 P := 0$ when $P=0$. There may be a negative linear relationship (over the range of sample sizes considered) between the Shannon entropy of the distribution of number of clusters returned by the algorithm and sample size ($\beta=-5.71 \times 10^{-5}$, $t(6)=-4.44$, $p=0.004$; $r^2=0.77$). Distributions were formed at each sample size by making 100 random draws from the post-stage 2 detections. This result may provide further quantitative evidence that the stability of the algorithm improves with the addition of data.

Figure 12:
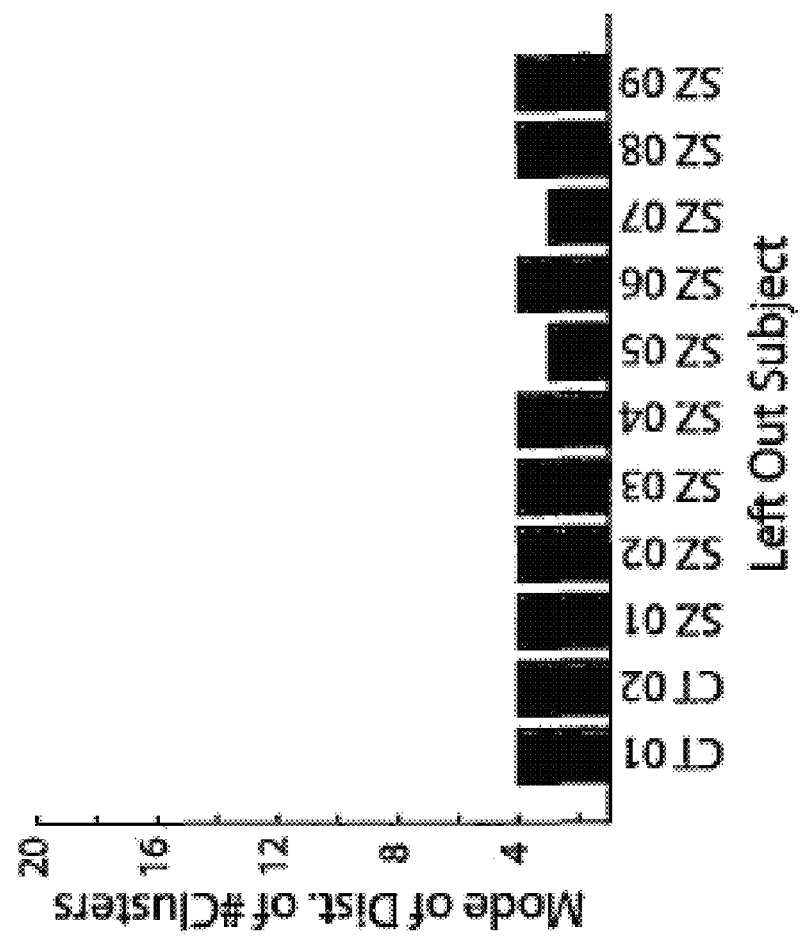
FIG. 12 is a graph illustrating the results corresponding to subjects of an experiment that were left out of a clustering.

In the second experiment, to examine the influences of individual subjects on the aggregate result, "leave-one-out" clustering was performed. Each subject, in turn, had his/her events removed from the pool available for clustering, and 5,000 events were randomly drawn without replacement from the remaining events, in 25 iterations. FIG. 12 shows the results summarized as a bar plot in which the height of each bar represents the mode of the distribution of cluster numbers for the 25 iterations.

FIG. 12 illustrates the results of an experiment in which each subject was left out of the clustering. Five thousand randomly selected events from all those passing through stage 2 in the remaining patients were clustered in 25 iterations. The x-axis shows the subject that was left out. The y-axis shows the mode of the distribution of number of clusters found in each of the 25 iterations.

Patients 5 and 7 altered the result from the in toto result of four clusters, in both cases bringing the number of clusters to three. This may suggest that these two patients were the predominant contributors to at least one of the four clusters. Subjects 5 and 7 account for 73% of the events in cluster 3, whereas they make an average combined contribution of 45% in clusters 1, 2, and 4 (and 48% to the total number of events clustered).

Taken collectively, the results of the individual patient and aggregated clustering experiments are objective evidence in support of the idea that human neocortex is capable of generating distinct classes of transient oscillations within the 100-500 Hz frequency band, and that there are at least three salient classes (excluding the putative artifact class).

Embodiments are described herein for automated identification of HFOs. A methodology is described for automatically detecting and/or clustering high-frequency oscillations on the human intracranial electroencephalogram. The systems, methods, and apparatus described herein may enable such large-scale analyses of data.

The automation may eliminate data pre-selection. Channels in the appropriate brain regions or epochs, during certain states of wakefulness, have been indicated as critical to the interpretability of findings, and/or that interesting results may be masked, in the absence of these steps. Many of the pre-selection steps previously thought to be critical may not be critical.

As described herein, HFOs may be implemented as control signals on board implantable seizure therapy devices.

Provided herein is a description of the existence, in the neocortex of epilepsy and control patients, of distinct classes of transient oscillations in the range between 100 and 500 Hz. Studies of HFOs in epilepsy may presuppose the existence of discrete entities termed "ripples" and "fast ripples." Embodiments are described herein that shown that there is a cluster of mixed-frequency events, and that it appears to be separate from two other clusters that are comprised more purely of a single frequency.

A waveform with a similar time domain characteristic to the mixed-frequency class prototype may be generated by applying a 100-500 Hz bandpass filter to a white Gaussian noise burst, for example. Having examined the spectra of these mixed frequency events and often observed two prominent peaks, they may be further investigated as a legitimately hybrid class of oscillations. As for the other three clusters, one may be comprised largely of clinically uninteresting recording artifacts. The other two may bear sufficient resemblance to what have been labeled ripples and fast ripples so that the oscillations that are recorded may be the same or similar to the oscillations that have been recognized by other researchers in the community.

It has been suggested that the relationship between subclasses of high-frequency oscillations recorded using non-standard, high bandwidth data acquisition systems may be a more reliable indicator of seizure-generating cortex than the waveform morphologies used by clinicians for seizure localization. HFOs are may not be, by default, part of the classical armamentarium of electrographic signatures used for localization because they may be difficult and/or impossible to visualize in standard clinical iEEG due to their short timescales, small relative amplitudes, and/or spectral contents that may exceed the bandwidth that may be recorded. Described herein is an algorithm for detecting and/or classifying these signals in an automatic fashion and/or demonstrating the tractability of exploring a data set of unprecedented volume. Using an unsupervised approach that does not presuppose a specific number of clusters in the data, direct evidence may be shown for the existence of distinct classes of oscillations within the 100 to 500 Hz frequency range in a population of neocortical epilepsy patients and controls. The number of classes found, four (e.g., three plus one artifact cluster), is consistent with studies that distinguish between ripple and fast ripple oscillations, and suggests that a class comprised of hybrid ripple/fast-ripple events may exist.

By minimizing selection bias and/or other human judgment in detecting and/or classifying HFOs, it may be possible to answer the important question of whether they can be used to delineate epileptogenic brain. Also described herein is the tractability of using machine learning techniques to analyze large streams of high resolution neurophysiologic data, that may be used on devices and techniques for mapping and modulating function and dysfunction in neurological disorders, on multiple brain scales for example.

Transient field-potential oscillations in the range of 100-500 Hz have been recorded from both normal and abnormal brain tissue in animals and humans. Subclasses of these high-frequency oscillations (HFOs) may be biomarkers for pathologic tissue. Understanding the potential relationship between HFOs and seizure generation may require the use of reliable automated tools for extracting HFOs from long continuous intracranial electroencephalographic records for example. Described herein is an automated HFO detector. The detector may be used without stringent manual data pre-selection and/or post-processing, which may make conclusions difficult to generalize. Building upon a detector, an HFO classification algorithm is described herein.

Described herein is an algorithm for the fully automated extraction of 100-500 Hz transient high-frequency oscillations (HFOs) from intracranial EEG recordings. Semi-automated approaches to HFO detection may use intensive visual pre- and post-processing in conjunction with machine detection.

HFOs may be described as human constructs categorizations imposed upon observed neurophysiological phenomena because they may aid in the understanding and/or ability to communicate about the workings of the brain. It is also described herein what an HFO embodies. This may be described in the study of HFOs from the ill-posed realm of trying to extract unknown (or at least difficult to agree upon) signals from a background noise whose statistical description may be almost equally elusive, to the more tractable realm of exploratory data analysis that may be driven by the concept of what characterizes HFOs.

The embodiment described herein may use a crude detector. The crude detector may be vetted by clinical opinion for its ability to find at least some things resembling what would catch the eyes of human reviewers for example. The crude detectors imperfect outputs may then be analyzed. If results of clinical importance are found, they may be used to refine the understanding of what the critical properties of HFOs are and/or to optimize the detector, in the hope that more, or different, information may be extracted in the next iteration. This evolutionary view of detector design is further described herein.

Fully automated HFO processing techniques may approximate the successes of semi-automated methods without data pre-selection and post-processing by humans. This may limit the scientific interpretability of conclusions about HFOs and seizure generation, including the ability to assess the generalizability and clinical utility of those findings, to a greater degree than the odd percentage point of sensitivity or specificity.

In an example experiment described herein, three board-certified epileptologists have classified detected HFO candidates and compared their markings with the outputs of the automated classifier described herein. This comparison is described in greater detail below.

Five thousand HFO candidates (~0.4%) were randomly selected among those identified in stage 1, across a number of patients. As a conservative measure, all events were excluded from the two subjects' (CT 02 and SZ 05) files from which a subset of data had been used to develop artifact-distinguishing features. The remaining 4,773 randomly selected events, across ten patients (nine epilepsy and one control), were used in a human labeling experiment. For CT 02, 1 of 1 data file was used in artifact training. For SZ 05, 1 of 8 total files was used in training. The number of patients from which events were drawn for the labeling experiment is one less than the total number of patients, not two.

Three board-certified neurologists independently marked all presented events as either valid (positive) or invalid (negative) HFOs, according to the following criteria for what constitutes a valid HFO: "Any transient, quasi-periodic voltage variation with predominant frequency between 100 and 500 Hz, lasting on the order of tens of milliseconds, standing prominently apart from the background signal, and having apparently physiologic origin."

The criteria were intentionally somewhat vague to reflect the fact that there is currently no standard operational definition of an HFO.

Figure 13:
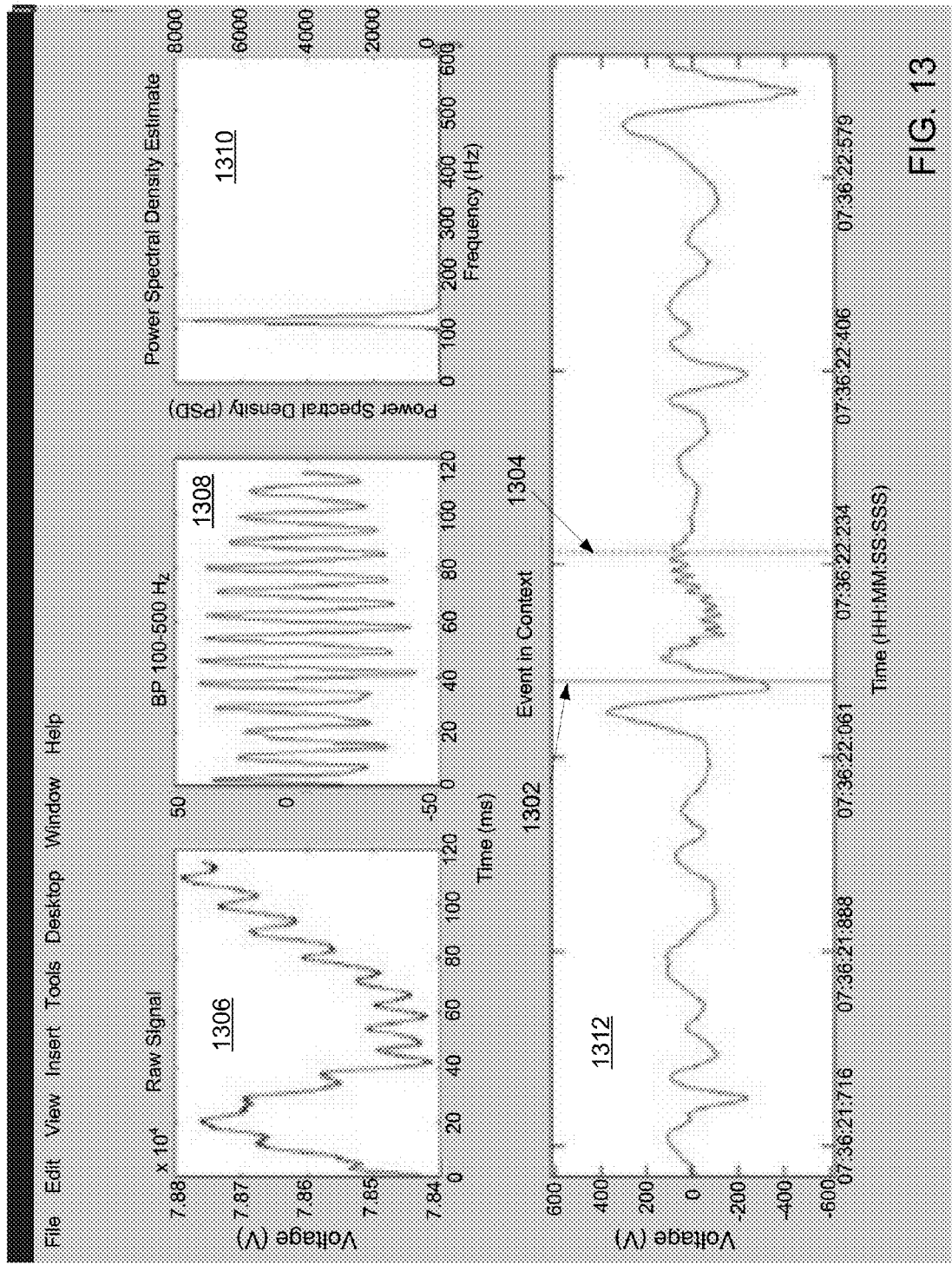
FIG. 13 is a screenshot of a GUI used to present detections to clinical reviewers.

Events were presented to reviewers via a custom MATLAB® graphical user interface (GUI), such as is shown in FIG. 13. FIG. 13 is a screenshot of a custom GUI used to present detections to clinical reviewers.

The GUI in FIG. 13 was comprised of four complementary views (1306-1312) of each HFO candidate. The bottom view 1312 displayed about 1 second (0.5 seconds on either side of the candidate) of 5 Hz-1 kHz single channel iEEG, sampled at 2,713 Hz, with vertical scaling of 21 µV/mm. Display distortion was in practice negligible at this default timescale due to the relatively low signal power above the effective Nyquist frequency of the display. As reviewers were free to zoom in (but not out), this compromise allowed a faithful representation of the full bandwidth across nearly all available time scales without the need for zoom-adaptive filtering. The event under consideration was delimited by vertical lines 1302 (start) and 1304 (stop) and the view could be scrolled for 30 seconds on either side of the default display window. The top, left view 1306 was of the raw data (near DC-9 kHz, 32,556 Hz sampling rate) corresponding to the detection. The top, middle view 1308 was of the bandpass data corresponding to the detection (100-500 Hz; 2,713 Hz sampling rate). The top, right view 1310 was a frequency-domain representation of the middle view. Unlike the bottom view 1312, whose vertical scaling was fixed, all top views 1306, 1308, and 1310 were autoscaled to fit their viewing windows. Reviewers were free to edit their markings until they had labeled every event and declared the task complete.

The human labeling task was binary, while the automated algorithm classified detections into one of five groups: four clusters, plus a fifth group ("Cluster 0") comprised of detections that were eliminated in stage 2. To compare human and machine performance directly, all events in cluster 0 and in cluster 2 were taken as machine-negative, whose centroid bore the closest qualitative resemblance to the artifacts that had features designed to identify. All other clusters were taken as machine-positive. This post-hoc labeling decision was made blinded to the human reviewers' markings. While it was made manually for the present experiment, it may readily be made automatically in the future if desired, such as by storing the coordinates of the cluster 2 centroid and assigning the negative HFO label to an automatic cluster whose centroid was sufficiently nearby for example.

The chi-squared test of homogeneity is used to test whether HFO counts are distributed identically across populations (where "population" is analysis-dependent), and the chi-squared test of independence to test whether marker labels are independent. The chance model used for markers assigns a positive label to each event with probability $p=N_p/N$, with $N_p$ the total number of events actually labeled positive by the marker and N the total number of marked events (4,773).

In describing the results below, the term "reviewer" is used to refer to humans and "marker," more generally, as a term that encompasses both humans and the machine algorithm. The terms "detection" and "event" may be used synonymously.

Human reviewers were not in agreement about the overall prevalence of HFOs in the data set of candidates presented to them. The percentages of detections marked as positive HFOs by reviewers A, B, C, and the machine classifier (M) were 24.6%, 5.5%, 11.5%, and 13.0%, respectively. The null hypothesis that the proportion of detections marked as positive was independent of human reviewer ($x^2(2, N=14,319) =763.84$, $p\ll0.0001$) was rejected. It may be apparent from these numbers that the automated method's propensity to mark events as positive is not extreme relative to humans'.

Figure 14:
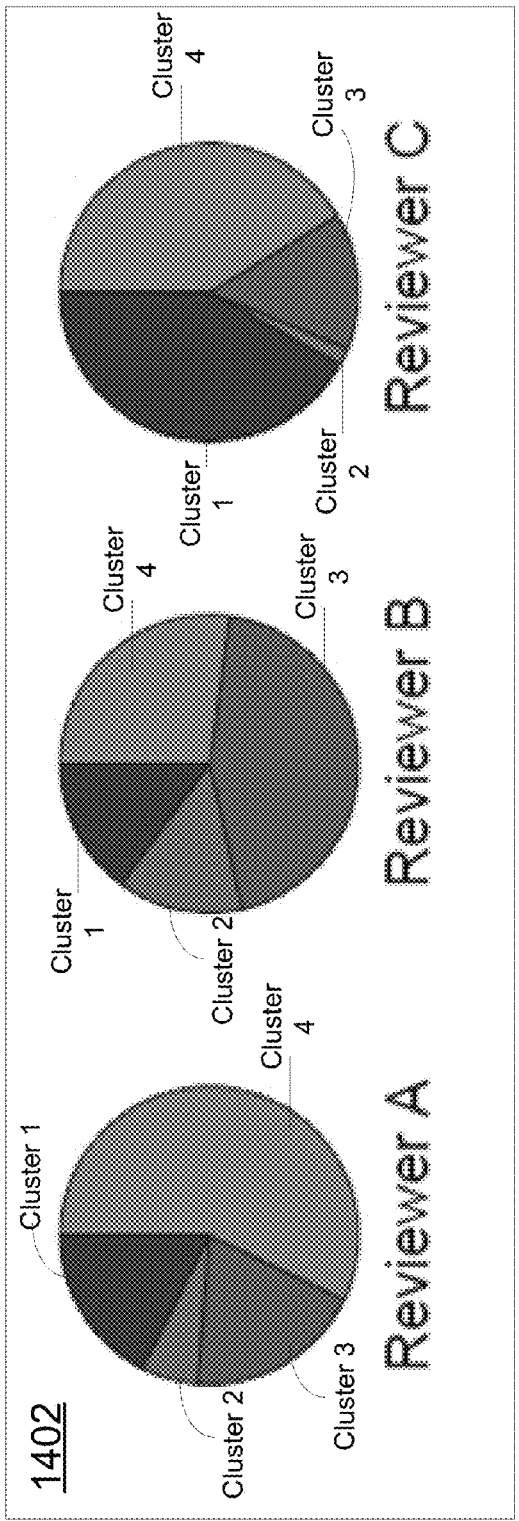
FIG. 14 is a group of pie charts, each illustrating the total number of positively marked HFOs by a human reviewer that were classified by a machine as belonging to a cluster.
Figure 14:
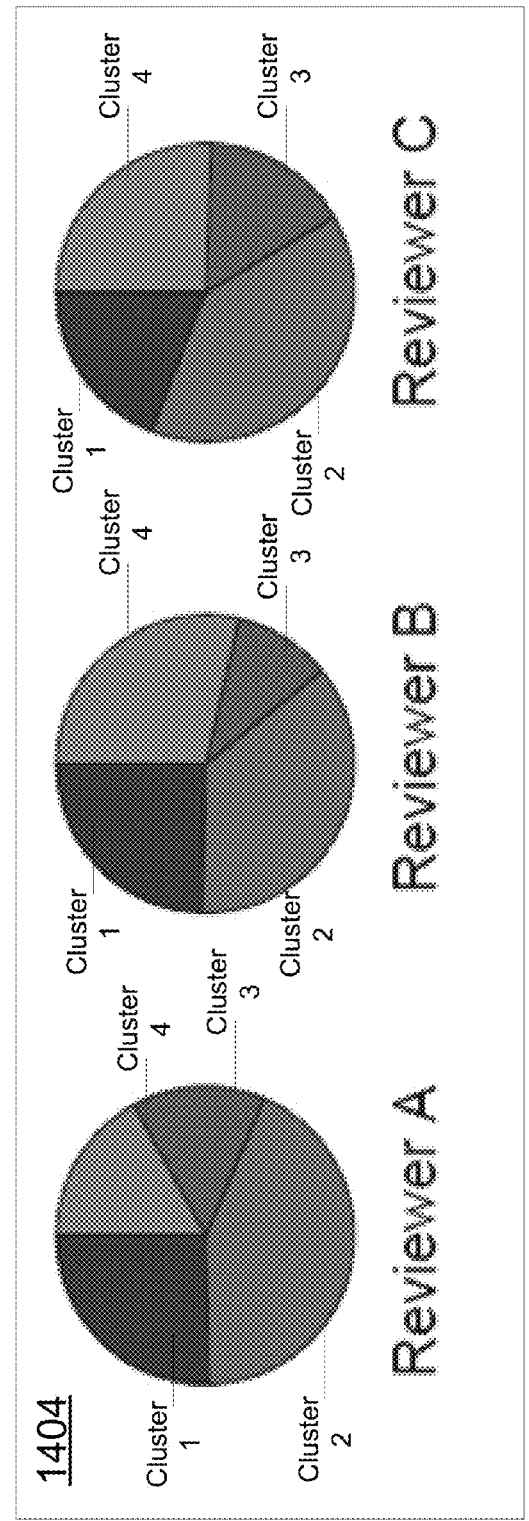

FIG. 14 illustrates a group of pie charts, where each whole pie represents the total number of positively marked HFOs by a human reviewer (Reviewer A; Reviewer B; and Reviewer C) that were classified by a machine as belonging to clusters 1, 2, 3, or 4. Pie wedges represent the proportion of such marks falling into each cluster.

Reviewers had clear and differing cluster preferences. FIG. 14, at 1402, shows, for each human reviewer, events falling into clusters 1-4 that were classified as positive HFOs. For Reviewer A at 1402, the majority of such detections (57.1%) fell into cluster 4. The largest clusters for Reviewer B at 1402 were 3 and 4, with the former (44.3%) favored over the latter (27.1%). Reviewer C, at 1402, displayed yet a third pattern, splitting a majority fairly evenly between clusters 1 (42.0%) and 4 (41.4%). For all three reviewers, the smallest percentage at 1402 was in cluster 2 (6.1%, 13.6%, and 1.9%, for A, B, and C, respectively), the putative artifact class. The null hypothesis that the proportion of detections in each of the four clusters was the same across human reviewers ($x^2(6, N=563) =97.40, p\ll0.0001$) was rejected.

FIG. 14, at 1404, shows, for each human reviewer, events falling into clusters 1-4 that were classified as negative HFOs. The putative artifact cluster dominates for all three reviewers: 43.3%, 36.1%, and 39.3% for Reviewers A, B, and C, respectively. And as is the case for positive labels, the null hypothesis that the proportion of detections in each of the four clusters was the same across human reviewers ($x^2(6, N=2197)=41.47, p\ll0.0001$) is rejected. Not shown in FIG. 14 are events that were marked as "0" by the automated detector—detections that were not classified into clusters 1-4 due to elimination in stage 2. These events are accounted for below, where standard performance metrics are given for the automated classifier against a ground truth set derived from the human reviewers' markings.

A question in defining ground truth data is to what degree the independent human reviewers agree amongst themselves regarding what constitutes an HFO and what does not. Table 4.1 gives contingency tables, including the kappa score (top left) and percentage agreement (top right), for each of the three human-human marker pairs (left) and each of the three machine-human marker pairs. For all tables, at the 5% significance level the null hypothesis that marker labels were independent are rejected, and the kappa values greater than one indicate that differences from chance were in the direction of agreement in all cases (AB: ($x^2(1, N=4773)=260.94$, $p\ll0.0001$); AC: ($x^2(1, N=4773)=25.09, p\ll0.0001$); BC: ($x^2(1, N=4773)=298.50, p\ll0.0001$); MA: ($x^2(1, N\ 4773)= 85.80, p\ll0.0001$); MB: ($x^2(1, N=4773)=270.96$, $p\ll0.0001$); MC: ($x^2(1, N=4773)=139.94, p\ll0.0001$)). The average pairwise percentage agreement among human reviewers was 79%, while that for machine-human pairs was 80%. The average pairwise kappa score among human reviewers was 0.15, while that for machine-human pairs was 0.17. The latter average and the individual kappa scores that comprise it may not be straightforward to interpret given the different biases of the reviewers.

TABLE 4.1

Confusion matrices, all marker pairs

| | | B | | |
|---|---|---|---|---|
| | 0.17 | 1 | 0 | 77% |
| A | 1 | 174 | 1001 | 1175 |
| | 0 | 88 | 3510 | 3598 |
| | | 262 | 4511 | 4773 |
| | | C | | |
| | 0.07 | 1 | 0 | 72% |
| A | 1 | 183 | 992 | 1175 |
| | 0 | 367 | 3231 | 3598 |
| | | 550 | 4223 | 4773 |
| | | C | | |
| | 0.23 | 1 | 0 | 88% |
| B | 1 | 117 | 145 | 262 |
| | 0 | 433 | 4078 | 4511 |
| | | 550 | 4223 | 4773 |
| | | A | | |
| | 0.12 | 1 | 0 | 73% |
| M | 1 | 245 | 374 | 619 |
| | 0 | 930 | 3224 | 4154 |
| | | 1175 | 3598 | 4773 |
| | | B | | |
| | 0.21 | 1 | 0 | 87% |
| M | 1 | 121 | 498 | 619 |
| | 0 | 141 | 4013 | 4154 |
| | | 262 | 4511 | 4773 |
| | | C | | |
| | 0.17 | 1 | 0 | 82% |
| M | 1 | 159 | 460 | 619 |
| | 0 | 391 | 3763 | 4154 |
| | | 550 | 4223 | 4773 |

Subjects have been aggregated across in computing these inter-rater agreement measures. Given the rarity of positive HFOs, sample sizes were too small to compute reliable statistics on an individual subject basis but inspecting kappa scores leads to the hypothesis that the degree of inter-marker agreement and the differences between human-human and machine-human pairs may vary with patient. For example, average human-human kappa for SZ 05 (1627 events) was 0.21 while the machine-human value was 0.27; for SZ 07 (1448 events) average performance was near chance for both human-human (−0.07) and machine-human (0.01) pairs; and for SZ 03 (295 events) average human-human kappa was 0.37, while average machine-human kappa was 0.19. It would be instructive to investigate these differences more systematically by conducting another marking experiment in which larger random samples of equal sizes were drawn from each subject.

As illustrated herein, a given human may be no more consistent with another human in his markings than with a machine.

Ground truth may look different depending on which of several plausible defining rules is adopted. 33.7% (chance, which should be higher=36.9%) of all detections were marked by at least one human reviewer as positive HFOs, while 39.6% (chance, which should be higher=45.1%) of all detections were marked by at least one marker as positive. 6.0% (chance, which should be lower=4.5%) of events were marked by at least two human reviewers (i.e. majority consensus) as positive HFOs, while 10.3% (chance, which should be lower=8.7%) of all events were labeled positively by at least two markers. 2.0% (chance, which should be lower=0.16%) of events were marked by all three viewers (i.e. unanimous consensus) as valid HFOs, while 2.5% (chance, which should be lower 0.74%) of all events were marked by at least three markers as positive. All reported values were different at the 5% level (chi-squared test) from their chance values, which were computed using the marginal probabilities displayed by each marker. These results are tangential to the point of the paragraph. The range of these values, which is affected by both the marginal probabilities displayed by each marker and the degree to which they tend to actually agree, gives one view of the general uncertainty among reviewers about what counts as an HFO.

A ground truth data set was formed by labeling as positive all events marked positively by at least two human reviewers (i.e., majority human vote) and as negative all remaining events. The overall accuracy of the automated classifier against this benchmark was 86.7%. Sensitivity was a moderate 46.8%, reflecting the conservatism of stage 2, which may be designed to retain events with large spectral dissimilarity from the background, a condition not explicitly enforced in the marking instructions for reviewers and to which it was anticipated that not all would adhere. Specificity was 89.2%, reflecting strong classification performance for negative events.

Given the relatively high marginal probability of negative events, however, precision was 21.5%. The $F_1$-measure, the harmonic mean of precision and sensitivity, was 0.30.

The precision metric reported above for the automated procedure may be viewed in light of the sparseness of positive events and in terms of its improvement on stage 1 alone. Moving from a data set that is 6% "pure" (six percent is the probability that a given event emerging from stage 1 would be declared a positive HFO by at least two human reviewers) to one that is 21.5% pure is an improvement of 258%. This effective increase in signal-to-noise ratio may improve the ability to detect differences in the rate at which true HFOs occur within and/or outside the seizure onset zone. Precision, as well as the other performance metrics reported, is dependent on the definition of ground truth. If a ground truth data set is considered whose positively labeled examples are the union of all three human reviewers' positive markings, for example, the precision improves to 54.6% (with the $F_1$-measure improving, indicating that this increase is not completely counterbalanced by a decrease in sensitivity). The precision metric reported above is an aggregated measure with respect to the machine clustering. The precision for each of the four clusters considered individually is different and in some cases higher than this aggregate measure, as described below.

Table 4.2 shows the performance results obtained when the ground truth definition is modified. For example, Table 4.2 shows the modified ground truth data set formed by taking as positive HFOs the stage 1 detections marked positive by at least two detectors. Values in parentheses are chance corrected. The modified ground truth set considers any event marked by at least two markers, human or automated, to be a positive HFO. The table compares the performance of each marker against this hybrid human-machine ground truth, and gives the difference between each metric and that expected under a chance model.

TABLE 4.2

| | Performance metrics, modified ground truth | | | |
|---|---|---|---|---|
| | A | B | C | M |
| Sensitivity (%) | 78.1 (1.2) | 44.2 (17.6) | 55.2 (4.9) | 69.1 (14.0) |
| Specificity (%) | 81.5 (1.1) | 98.9 (2.4) | 93.5 (1.3) | 93.4 (2.3) |
| Accuracy (%) | 81.1 (1.0) | 93.3 (2.9) | 89.5 (1.0) | 90.9 (3.0) |
| Precision (%) | 32.5 (5.2) | 82.4 (40.0) | 49.1 (11.1) | 54.6 (18.0) |
| F-measure | 0.46 (0.057) | 0.58 (0.253) | 0.52 (0.087) | 0.61 (0.167) |

Chance values, which may be computed exactly, were for convenience generated by simulation as described herein. For each rater, 100 random m×n marking matrices were generated, where m was the total number of marked events (4,773) and n was the total number of markers (4). Random marking matrices were drawn according to actual probability mass function displayed by each reviewer. For each trial, performance metrics were computed using the modified ground truth rule described above, and the 100 values in each performance metric category were averaged to yield a final expected value for each. Values in parentheses in the table are the differences between the observed values and these chance values.

Given a machine-positive HFO cluster (such as 1, 3, or 4 for example) the probability that one of its members was marked positive by human reviewers was dependent on cluster. Table 4.3 shows these results for two cases, one in which ground truth positive is taken to be the union of all human reviewers' positive markings and one in which ground truth positive is taken to be a majority vote. For completeness, the values computed for cluster 2 are included. For both the majority ground truth ($x^2(2, N 619)=13.64$, $p=0.0011$) and the union ground truth ($x^2(2,N=619)=33.88$, $p<<0.0001$), the null hypothesis, that the proportion of ground truth positive events occurring in each of the three machine positive clusters is the same, was rejected.

TABLE 4.3

| | Cluster purity | |
|---|---|---|
| | Majority | Union |
| Cluster 1 | 0.15 | 0.40 |
| Cluster 2 | 0.01 | 0.11 |
| Cluster 3 | 0.32 | 0.54 |
| Cluster 4 | 0.21 | 0.67 |

The results of this marking study reinforce that the stages of describing high-frequency oscillations within the brain are nascent. Human reviewers do not agree on the prevalence of HFOs. Nor do they agree on what constitutes an HFO when they see one. It may be suggested that, in addition to poor inter-rater agreement, intra-rater reliability may be moderate at best. Different reviewers demonstrate strong preferences for waveforms with differing characteristics. The level of agreement does exceed chance—there is a core of commonality worth investigating more thoroughly. The evidence makes it clear that "ground truth" HFO data are a false sense of security, and may be regarded as suggestive rather than authoritative.

The automated algorithm described herein performs similarly to humans at the task of culling positive exemplars from a large set of candidate HFOs. Humans agree no more with each other than they do with the machine. The second and third stages of the automated algorithm, taken together, offer improvement in positive predictive value over the stage 1 detector alone. This may be more if individual clusters are considered, some of which may capture waveform features that are more saliently HFO-like to humans than others. The automated approach provides the advantages of being perpetually consistent in its application of detection criteria and/or indefatigable in its marking effort.

The relative uncertainty among humans about what constitutes an HFO gives confidence in framing this type of work as exploratory, and in the value of studying the outputs of the algorithm described herein. Examined herein are the relationship between the clusters that may be found and putative areas of seizure generation.

A quantitative analysis is described for HFO subclasses and their rates of occurrence. An example experiment was performed in a group of nine patients with epilepsy believed to be of neocortical origin and two control patients with no history of seizures. HFOs were detected and classified automatically in continuous long-term micro- and macro-intracranial recordings without performing data pre-selection. The results included the following: (1) a cluster of HFOs with power concentrated in the low end of the 100-500 Hz band (median spectral centroid=137 Hz) is increased in the seizure onset zone; (2) a cluster with power concentrated in the high end of the band (median spectral centroid 305 Hz) is not; (3) no evidence is found that the rates at which HFOs are generated are different for control neocortex and non-seizure onset zone neocortex in epilepsy patients; and (4) while HFOs recorded on parenchyma-penetrating microelectrodes have higher peak 100-500 Hz frequencies than penetrating macroelectrodes, this relationship does not hold for epipial electrodes on the neocortical surface.

Reliable and quantifiable biomarkers for epileptic tissue may include transient, quasi-periodic field potentials within the 100-500 Hz frequency range. These signals, which last on the order of tens of milliseconds, may be observed in hippocampus and parahippocampal structures, as well as in neocortex for example. They may be recorded in normal and epileptic animals and in epileptic humans, using electrodes varying in size from the micron to the millimeter scale. In the epilepsy community (and outside) they are termed "high-frequency oscillations" (HFOs), to distinguish them from the slower activity (0.1-40 Hz) that may be used in making clinical determinations of the SOZ.

HFOs may be subdivided, conceptually and/or for analytical purposes, into "ripples" (100-200 Hz) and "fast ripples" (250-500 Hz). This may reflect differences in their cellular and network-level generating mechanisms, as well as their relationships to epileptogenic areas for example. A further complicating factor is that studies of HFOs in epilepsy have been hampered by selection bias arising primarily out of the need to reduce the volume of data so that clinicians may manually review it.

An algorithm is described herein for the automated detection and/or classification of HFOs that may not need human intervention and/or may not presuppose the existence of any specific number of classes, ripples and/or fast ripples included. The outputs of that algorithm in a group of nine neocortical epilepsy and two control patients implanted subdurally with hybrid macro/micro electrode arrays is quantitatively analyzed herein. Three items are addressed herein about the relationship between neocortical high-frequency oscillations and seizure generation and the sensors used to record them. These items include: 1) whether the rates at which HFOs are generated are different in control patient neocortical regions and the non-seizure onset-zone (NSOZ) neocortical regions of epilepsy patients; 2) whether the rates at which HFOs are generated are different within and outside the SOZ in epilepsy patients; and 3) whether microelectrodes tend to record HFOs of higher frequency than macroelectrodes, as may be expected if fast ripples were a more local phenomenon than ripples.

In an experiment described herein, the data set analyzed is comprised of 219,756 putative high-frequency oscillations recorded from the neocortices of eleven human subjects with subdurally implanted electrode arrays. Nine subjects had medically refractory partial epilepsy believed to be of neocortical origin and received electrode implants as part of routine clinical care. The location, number, and type of intracranial electrodes (grid and/or strip electrodes) were determined by a multidisciplinary team including neurosurgeons, neurologists, neuroradiologists, and neuropsychologists. Depth electrodes were implanted in some subjects; standard clinical depth leads were modified in two ways: 1) by embedding microwires around the circumference of the lead-body between the 2 mm long clinical contacts; and 2) by passing a bundle of microwires within the lumen of the lead, so that they protruded by approximately 7-8 mm from the distal tip. To ensure that the conclusions described herein pertain to neocortex, depth electrode data was excluded from all but one analysis, which is clearly described herein. The purpose of the latter analysis was to contrast depth and surface electrode results. Insufficient amounts of depth electrode data precluded comparative analyses elsewhere. Standard clinical grid and strip electrodes were modified under an Institutional Review Board (IRB)-approved research protocol by adding arrays of non-penetrating platinum-iridium microwires (40 μm diameter, with intra-array spacing of 0.5-1 mm center-to-center) between the clinical, 4 mm diameter contacts. Two "control" patients with chronic intractable face pain but no history of seizures, were similarly implanted, as part of an unrelated IRB-approved research protocol investigating electrical stimulation of motor cortex as a potential treatment for their condition.

Continuous, long-term data were acquired using the Digital Lynx Data Acquisition System (NEURALYNX, Inc., Bozeman, Mont.) at 32,556 samples per second and 20 bits per sample (stored), from up to 144 channels in each patient. The input dynamic range was ±1.32 mV and the noise level was ~1.3 μV root-mean-square (RMS), yielding approximately 18 effective bits. Recordings were made using direct-current (DC) capable amplifiers, and a 9 kHz analog low pass filter was employed to minimize aliasing effects. The bandwidth of the raw recordings was thus approximately near-DC −9 kHz.

Event data were extracted from the raw intracranial EEG (iEEG) using a three-stage process detailed in the methodology chapter. In the first stage, candidate events were detected within non-overlapping ten-minute windows of 100-500 Hz bandpass filtered iEEG (data were first decimated by a factor of 12, to 2,713 Hz), on a per-channel basis. Amplitude and duration thresholds were applied to the short-time energy of the signal in each window. Flagged segments were subject to waveform shape criteria to ensure robustly oscillatory characteristics. In the second stage, a Gaussian mixture model of the local background iEEG (~2.5 sec) surrounding each candidate was learned using the Expectation Maximization (EM) Algorithm, and events bearing too large a spectral similarity to background according to the model were discarded from candidacy. In the final stage, events were clustered using the k-mediods algorithm, with the gap statistic used to determine the optimal number of clusters. The approach yielded four clusters, which are described herein.

For each patient, recorded seizures were visually identified by a board-certified epileptologist prior to data analysis. The time of the earliest iEEG change was noted and the associated macroelectrode(s) were selected as the electrographic seizure onset zone. Time of earliest iEEG change was determined by identifying a clear electrographic seizure discharge in a macroelectrode recording and looking backward in the record for the earliest change from background contiguously associated with the discharge. As microelectrode recordings were not used in clinical determination of the SOZ, their labels were extrapolated from those of the macro-electrodes. A microelectrode was given the label of SOZ if it belonged to a cluster immediately adjacent to a non-peripheral SOZ macroelectrode.

A permutation test was used to test the null hypothesis that there was no difference in the average median event rate between control and NSOZ groups. The permutation distribution was generated by taking 55 (11-choose-2) possible groups of 9 and 2 subjects and computing the difference between the average median event rates for the two groups. Separate tests were carried out for each of the four clusters, and for macro- and microelectrodes, yielding eight total tests.

Because of the large variability in median event rates across seizure subjects, and because not all subjects were represented in all channel classes, two subjects had surface microelectrodes in the physician-labeled SOZ for example, subjects were not aggregated across in studying the difference between SOZ and NSOZ channels. Subjects were considered eligible for analysis if they had at least five SOZ channels and five NSOZ channels of a given channel class (i.e., macroelectrode or microelectrode). Of the nine seizure patients, five met this criterion for macroelectrodes (SZ 01, SZ 05, SZ 06, SZ 07, and SZ 09) and two for microelectrodes (SZ 02 and SZ 06). For each eligible patient, using event rate as the measured variable on channels, it was tested that the null hypothesis that the cumulative distribution function of event rates for SOZ channels was equal to that for NSOZ channels. This same test is commonly described as a test for a difference between the medians of two groups. Separate analyses were carried out for each of the four clusters, and for macro- and micro-electrodes, yielding a maximal total of eight tests per patient. The Mann-Whitney U test was used to test the null hypotheses, with the Bonferroni adjustment made to account for multiple comparisons.

For each of the 219,756 neocortical surface events, the peak frequency within the 100-500 Hz frequency band was computed using a multitaper method (3 tapers; 512-point Discrete Fourier Transform (zero-padded); adaptive nonlinear combination method). The null hypothesis, that the cumulative distribution functions of event peak 100-500 Hz frequencies were equal for macro- and microelectrodes, was tested, with the alternative hypothesis being that the microelectrode distribution was stochastically larger. The Mann-Whitney U test was used for the comparison. The same was then done for the 70,517 depth electrode events.

Across eleven subjects, a total of 219,756 putative high-frequency oscillations (100-500 Hz) were automatically detected on neocortical surface channels and clustered by the algorithm described herein. The statistical clustering approach that was used assumed no specific number of HFO groups in the data. It assumed that the number was somewhere between one and twenty. Four clusters were discovered. The methodology description herein demonstrated the stability of the clustering algorithm and qualitatively described the waveform morphologies representative of each cluster. The clustering outputs were analyzed, rather than the clustering method, quantitatively, and in relation to variables of clinical interest.

Figure 15:
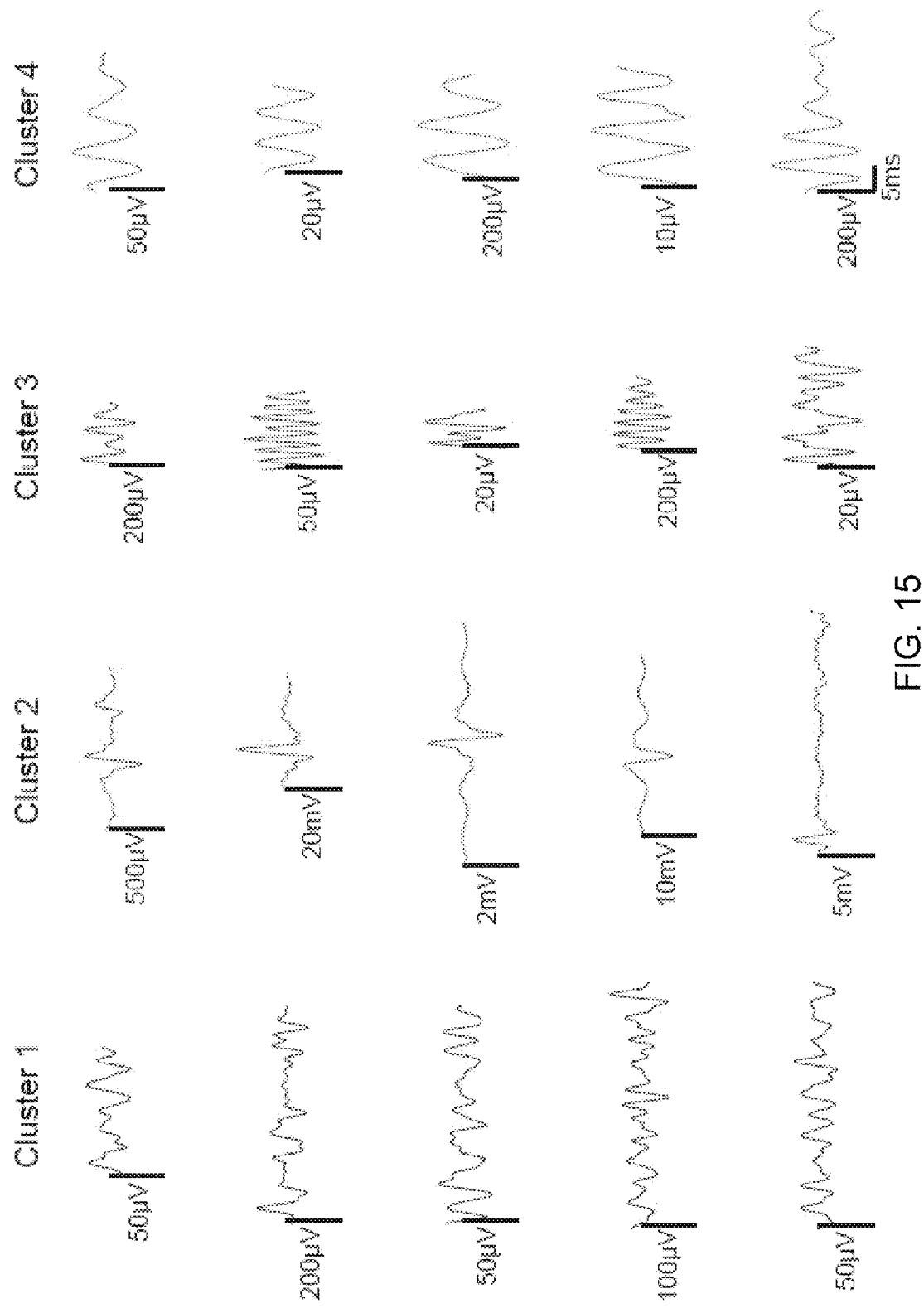
FIG. 15 illustrates five randomly selected waveforms from each of four clusters found using automated detection and/or unsupervised classification.

Twenty-nine percent (63,652) of detections belonged to a cluster (cluster 2) characterized by sharp, supra-physiological voltage transients. The sharp features yielded oscillations when bandpass filtered, thereby generating putatively false positive detections. Of the remaining putatively physiological events, 41% (64,392) belonged to a cluster (cluster 1) characterized by mixed-frequency, irregular waveforms; 11% (16,691) belonged to a cluster (cluster 3) characterized by relatively fast, regular waveforms; and 48% (75,021) belonged to a cluster (cluster 4) characterized by relatively slow, regular waveforms. FIG. 15 shows five randomly selected examples from each of the four clusters, illustrating these properties.

FIG. 15 illustrates five randomly selected waveforms from each of the four clusters found using automated detection and unsupervised classification. The waveforms are 100-500 Hz bandpass filtered segments corresponding to detections (truncated to 25 ms, if necessary, to put the waveforms on the same time scale for comparison). These waveforms differ from those shown in FIG. 8, at 804, in that they are drawn exclusively from neocortical surface channels.

Table 5.1 gives descriptive statistics for each cluster. In table 5.1 entries are (median, interquartile range); AU=arbitrary units; PR=power ratio; SC=spectral centroid; LL=line length; and SP=spectral peak. Four quantities were computed for each detection (i.e., cluster member). The four quantities include: 1) the ratio of the integrated power spectral density estimate (PSD) in the 250-500 Hz frequency band to that in the 100-200 Hz band (power ratio); 2) the centroid of the PSD within the 100-500 Hz frequency band (spectral centroid); 3) the line length of the spectrally equalized time-domain signal, normalized by signal duration (line length); and 4) the peak of the PSD in the 100-500 Hz band (spectral peak).

TABLE 5.1

| | Cluster statistics | | | |
|---|---|---|---|---|
| Feature | Cluster 1 (n = 64392) | Cluster 2 (n = 63652) | Cluster 3 (n = 16691) | Cluster 4 (n = 75021) |
| PR | (0.823, 0.986) | (0.833, 1.018) | (3.725, 3.196) | (0.0357, 0.1069) |
| SC (Hz) | (219, 49) | (220, 50) | (305, 37) | (137, 35) |
| LL (AU) | (0.0313, 0.0123) | (0.00657, 0.00881) | (0.0242, 0.0299) | (0.0263, 0.0110) |
| SO (Hz) | (193, 61) | (167, 64) | (302, 87) | (146, 32) |

Since these quantities represent a subset of the features used to derive the clusters themselves, statistical comparison of their values across groups (using, for example, nonparametric analysis of variance methods) may not be appropriate. Examining the values in table 5.1 may give a sense for the between-group differences that drove the clustering.

It may be seen, for example, that cluster 3 events tend to have higher peak 100-500 Hz frequencies than cluster 4 events. The relative proximity of the spectral centroid value to the spectral peak value in clusters 3 and 4, compared with clusters 1 and 2, suggests that the former pair (clusters 3 and 4) have their power concentrated in a narrower band within 100-500 Hz than the latter (clusters 1 and 2)—corroborating the descriptor "regular" for clusters 3 and 4 in the discussion above. Clusters 1 and 2 appear primarily distinguished by their line length values, which is consistent with the observation that cluster 2 events are characterized by sharp transients. Large sample-to-sample voltage differences that would contribute to high line-length values are present for a relatively smaller fraction of the overall segment duration in cluster 2 versus cluster 1 events. Cluster 1 events have spectral centroid values that are intermediate between those of clusters 3 and 4, supporting the observation that cluster 1 events tend to have relatively strong spectral components in both the 100-200 and 250-500 Hz band, and leading to their qualitative description as "irregular." Cluster 3 events have a median peak frequency that is consistent with that of "fast ripples," and cluster 4 events with that of "ripples."

Table 5.2 shows aggregated event rates for clusters 1, 3, and 4 (i.e., all but the putatively artifact class), broken down by patient and by channel class. In table 5.2, triplets are (number of channels, median event rate, interquartile range), where an "event" is any member of cluster 1, 3, or 4 (i.e., putative artifact cluster 2 excluded). Units for the medians and interquartile ranges are $\times 10^{-4}$ counts/sec. ChH=Channel hours, the sum over all channels of the length of time recorded for each channel. Each cell in the table gives the number of channels, the median aggregate event rate for those channels, and the interquartile range. The final column gives the total number of channel-hours of data recorded per patient.

TABLE 5.2

| | Channel statistics | | | | |
|---|---|---|---|---|---|
| | Channel Class | | | | |
| | NSOZ | | SOZ | | |
| Sub | Mac | Mic | Mac | Mic | ChH |
| CT 01 | (16, 26.87, 17.69) | (128, 14.29, 19.73) | (0, —, —) | (0, —, —) | 1176 |
| CT 02 | (24, 13.54, 8.71) | (104, 8.71, 11.27) | (0, —, —) | (0, —, —) | 1877 |
| SZ 01 | (34, 2.34, 3.13) | (6, 11.72, 8.07) | (5, 48.96, 131.25) | (0, —, —) | 480 |
| SZ 02 | (22, 13.43, 14.07) | (79, 10.19, 11.16) | (1, 12.78, 0.00) | (24, 12.59, 8.61) | 1890 |
| SZ 03 | (27, 31.37, 12.25) | (33, 37.84, 29.61) | (1, 32.55, 0.00) | (0, —, —) | 864 |
| SZ 04 | (51, 18.54, 7.86) | (28, 9.44, 8.51) | (3.18.87, 4.72) | (0, —, —) | 1921 |
| SZ 05 | (33, 19.32, 7.91) | (0, —, —) | (11, 22.91, 4.34) | (0, —, —) | 2860 |
| SZ 06 | (17, 2.65, 2.72) | (25, 8.03, 8.32) | (6, 7.75, 1.73) | (67, 8.35, 7.27) | 10139 |
| SZ 07 | (57, 23.97, 16.79) | (22, 0.00, 8.33) | (7, 35.24, 14.06) | (0, —, —) | 5615 |
| SZ 08 | (36, 5.05, 1.49) | (0, —, —) | (0, —, —) | (0, —, —) | 234 |
| SZ 09 | (81, 2.03, 1.22) | (22, 0.00, 1.63) | (7, 2.85, 0.71) | (0, —, —) | 735 |

The table provides context for the statistical analyses of the following descriptions, making sample sizes clear and indicating where data are unavailable. For seven of the eight (all but SZ 02) seizure subjects for whom the comparison can be made, the median aggregate event rate is higher in the seizure onset zone than the non-seizure onset on macroelectrodes. The same is true on microelectrodes for two of the two subjects for whom the comparison may be made.

Figure 16:
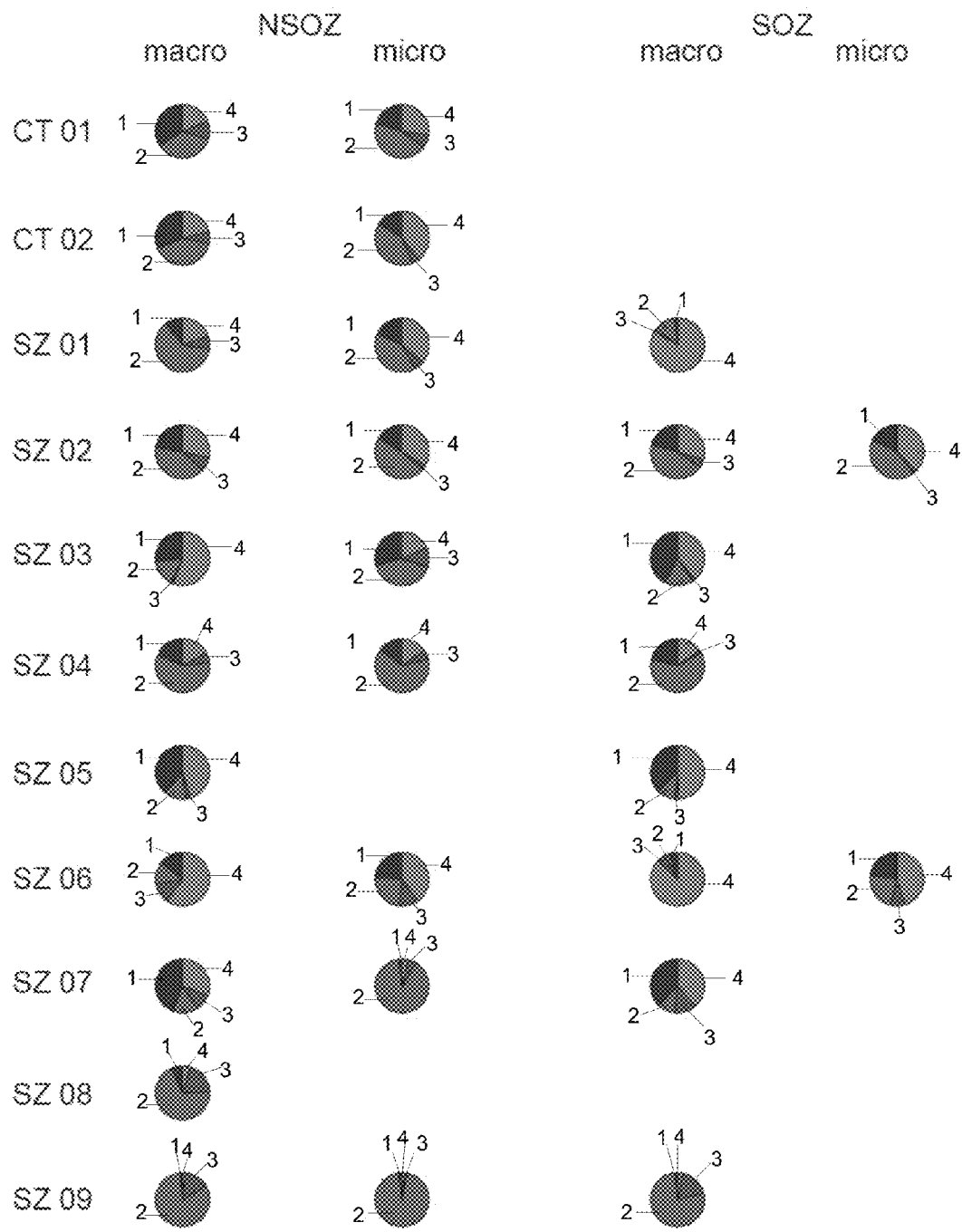
FIG. 16 is a group of pie charts illustrating the average proportion of events falling into each of four clusters, broken down by patient and channel class.

FIG. 16 complements table 5.2, showing the average proportion of events falling into each of the four clusters, broken down by patient and channel class. Clusters are indicated with a number corresponding to the cluster numbers represented in FIG. 15. The area of each pie chart wedge corresponds to the mean proportion of events in a given cluster (1=cluster 1; 2=cluster 2; 3=cluster 3; and 4=cluster 4), where the mean is over all channels in the category defined by the row and column of the pie. Empty cells in the table indicate that no data was available.

Two trends are apparent in subjects whose pie charts represent more than a single channel (SZ 02 and SZ 03 each have only one macroelectrode in the SOZ): 1) cluster 3 typically accounts for the smallest proportion of events; and 2) cluster 4 typically accounts for a greater proportion of events in SOZ than in NSOZ channels. It is tested, as described below, whether the trends toward higher event rates in the SOZ apparent in Table 2 and FIG. 16 are statistically significant, disaggregating clusters to discern which are responsible for any significant effects.

Even at the liberal alpha level of 0.1, no significant differences were found between control and seizure patient-NSOZ groups. For macroelectrodes, p-values for permutation tests of differences between the average median event rates of control versus seizure patient NSOZ groups, before correcting for multiple comparisons, were: 0.25, 0.82, 0.56, and 0.69 for clusters 1, 2, 3, and 4, respectively. The corresponding p-values for microelectrodes were 0.92, 0.63, 0.92, and 0.94. Given the small number of control subjects these tests may have little power, but they lead to the conclusion that there is no evidence to reject the null hypothesis of no difference between control and seizure-NSOZ groups.

Event rates were compared on SOZ channels to NSOZ channels on an individual subject basis, by electrode type (macro or micro) and by cluster. Five of nine seizure patients met the inclusion criterion (at least 5 channels in each class, SOZ and NSOZ) for macroelectrode comparisons, and two of nine met the same inclusion criterion for microelectrode comparisons. For microelectrodes, no significant differences were found between SOZ and NSOZ for any of the clusters, in either of the eligible patients. For macroelectrodes, no significant differences between SOZ and NSOZ were found in any of the patients for clusters 1-3.

For cluster 4, four of five eligible patients had higher median event rates on SOZ macroelectrodes. Uncorrected p-values for the Mann Whitney U test in these subjects—SZ 01, SZ 05, SZ 06, and SZ 07—were 0.00036, 0.037, 0.00069, and 0.098. The marginally significant (at alpha=0.1) results for patients SZ 05 and SZ 07 do not survive the Bonferroni correction.

One eligible subject that did not have a higher median cluster 4 event rate for macroelectrode SOZ channels was SZ 09, who, anomalously, had median rates of zero on both channels. Though the median rate was not higher in SOZ channels for this subject, the mean rate was higher, by a factor of 1.7. High percentages of NSOZ and SOZ channels without any cluster 4 events was not surprising for this subject, given the uniquely poor quality of SZ 09's recordings, which is evidenced by the predominance of cluster 2 represented in that subject's plots in FIG. 16. The results of the NSOZ to SOZ comparisons for macroelectrodes are summarized in the box plots of FIG. 17.

Figure 17:
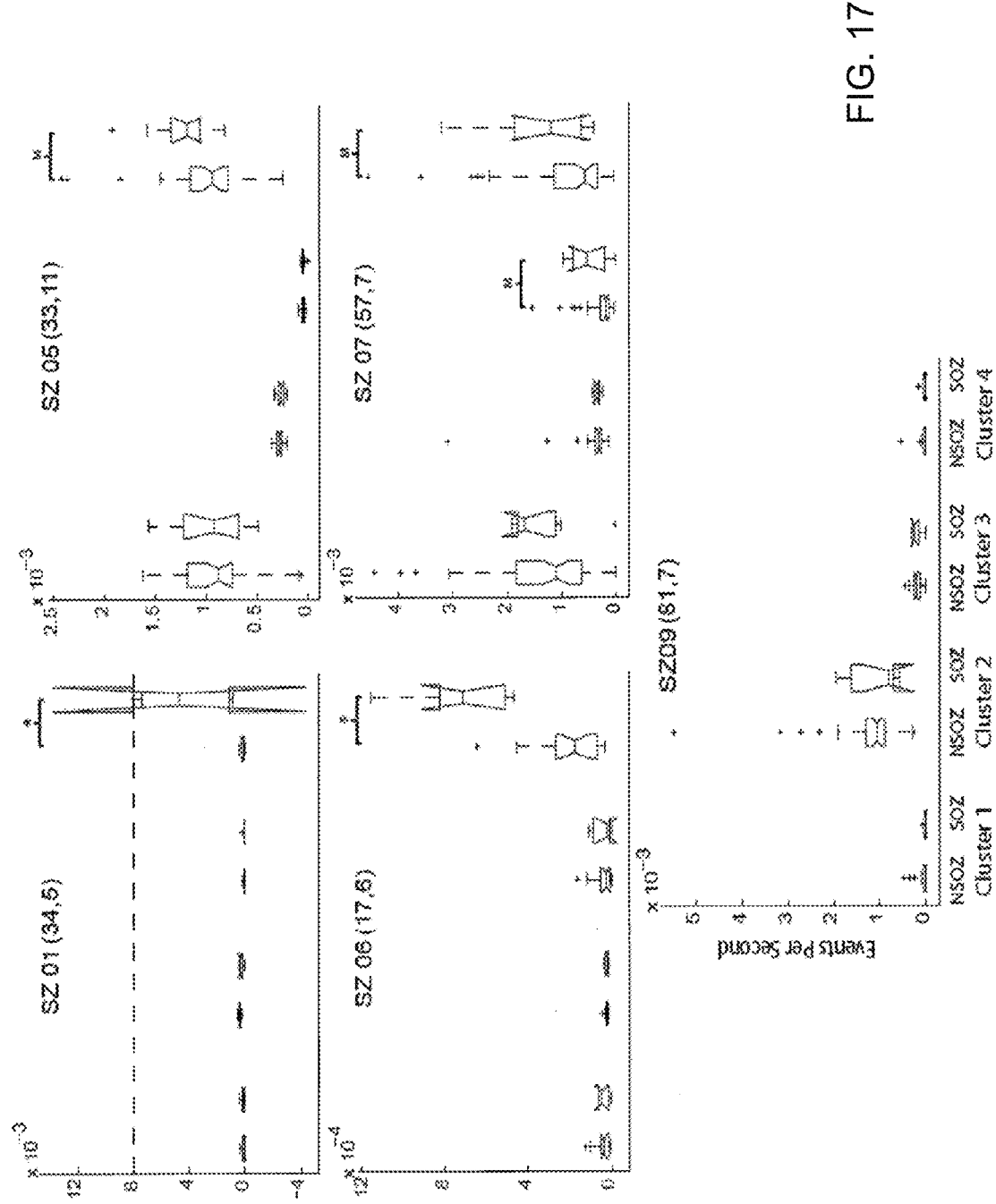
FIG. 17 shows the results of an NSOZ to SOZ comparisons for macroelectrodes.

In FIG. 17, each panel corresponds to results for one of the five subjects who met the inclusion criterion (at least 5 channels in each of the SOZ and NSOZ). Numbers of channels upon which box-and-whisker plots are based are shown in parentheses at the top of each panel, next to the subject name as (#NSOZ, #SOZ). There are two box-and-whisker plots for each of the four clusters, one corresponding to NSOZ channels (left) and one to SOZ channels. On each box, the central mark is the median event rate (counts/sec) and the edges are the $25^{th}$ and $75^{th}$ percentiles. Whiskers extend to the most extreme data points not considered outliers. Outliers are defined as points greater than 1.5 times the interquartile range above the $75^{th}$ percentile or below the $25^{th}$ percentile. Outliers are plotted individually as crosses. Dotted line in top left panel represents an arbitrary value to which a single large outlier ($34.7 \times 10^{-3}$) was clipped for visualization purposes. Notch widths are computed. Lack of notch overlap is a rough test for significant differences in medians at the 5% significance level. The Mann-Whitney U test is used on the distributions to more formally test significance. (*=Bonferroni corrected p-value for Mann-Whitney U test <0.1, M=marginally significant at alpha level 0.1, but may not survive the Bonferroni correction).

In contrast to findings from human temporal lobe, in neocortex no evidence ($p \approx 1$) is found to reject the null hypothesis of no difference in favor of the alternative hypothesis that the cumulative distribution function of event peak 100-500 Hz frequencies is stochastically larger for microelectrodes than macroelectrodes.

Figure 18:
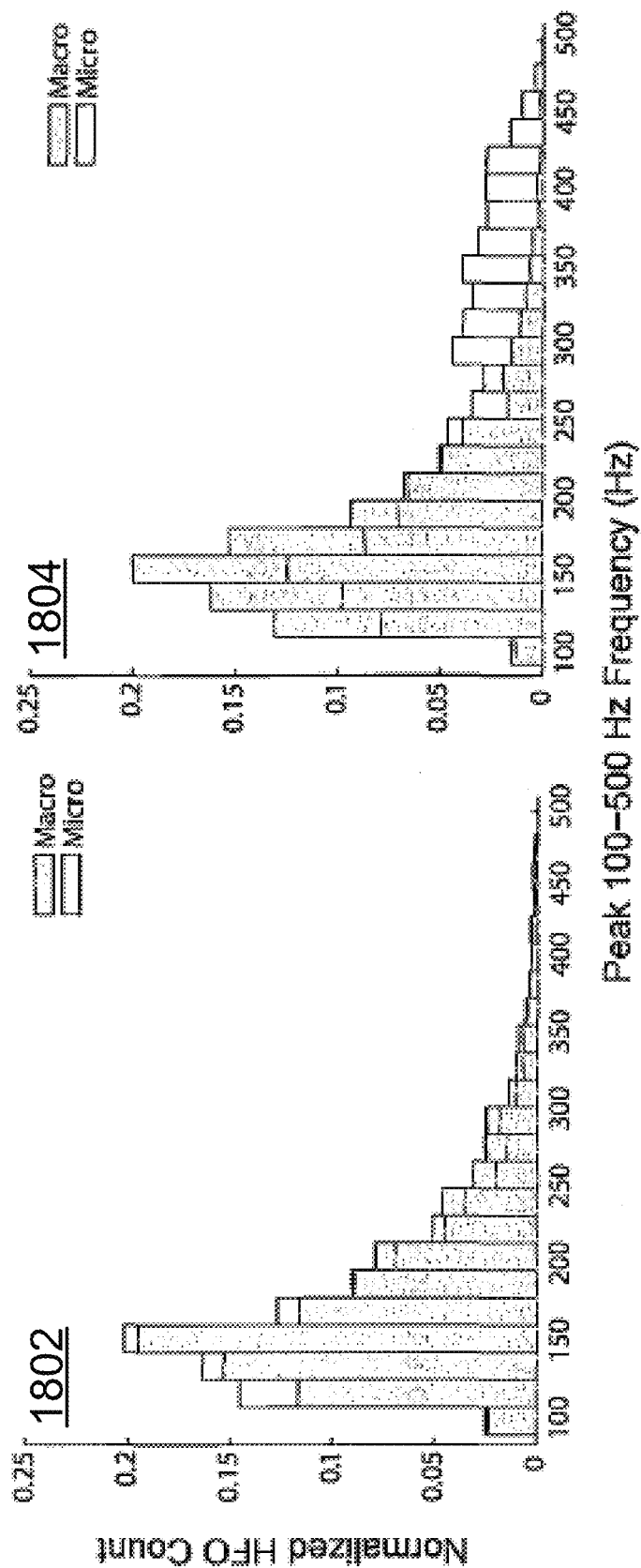
FIG. 18 shows two graphs illustrating histogram density estimates for the peak 100-500 Hz frequency of events on micro- and macro-electrodes.

FIG. 18 show two graphs illustrating histogram density estimates for the peak 100-500 Hz frequency of events (clusters 1-4, aggregated) on macro-(white) and macro-(hatched) electrodes, for surface electrodes (in graph 1802) and depth electrodes (in graph 1804). As illustrated in FIG. 18, in graph 1802, the distributions for macroelectrode events (n=130, 098) and microelectrode events (n=89, 658) look qualitatively similar, and the medians are close (macro median, interquartile range: 170,69; micro median, interquartile range: 164,61). In fact, a post-hoc two-sided Mann Whitney U test finds evidence for the opposite effect (p<<0.001), namely that macroelectrodes have a tendency to record events with peak 100-500 Hz frequencies that are slightly higher than those for microelectrodes.

FIG. 18, at graph 1804, shows a result that does agree with findings from the temporal lobe. It depicts the same two distributions as in FIG. 18 at graph 1802, but for depth electrodes, which were implanted in four of the nine seizure patients (SZ 03, SZ 04, SZ 05, and SZ 08) in addition to surface electrodes. Depth macroelectrodes yielded 11,179 events on 40 total channels in these four subjects. Depth microelectrodes, present in two of the four subjects, yielded 59,338 events on 84 total channels. In FIG. 18, at graph 1804, the distributions show a strong qualitative difference. The medians are much farther apart than for the surface electrodes (macro median, interquartile range: 167,58; micro median, interquartile range: 209,154). Here, the one-sided Mann-Whitney U test, with alternative hypothesis that microelectrodes have stochastically larger peak (100-500 Hz) event frequencies than macroelectrodes, leads to the rejection of the null hypothesis of no difference (p<<<0.0001).

There are four findings from the experiments that are further described herein. These findings include: 1) in a group of neocortical epilepsy patients, using automated detection and classification techniques without data preselection, a class of HFOs have been identified corresponding to ripples whose rate of occurrence is increased in the physician-labeled seizure onset-zone; 2) a class of oscillations corresponding to fast ripples is relatively rare, and may not show a rate increase in the neocortical seizure onset-zone; 3) no evidence is found that control neocortex is different from neocortex outside the seizure onset zone in epilepsy patients, when considering the rate at which HFOs are generated; and 4) while microelectrodes on the neocortical surface may not appear to preferentially record HFOs of higher frequency, microelectrodes embedded in the parenchyma do.

Described herein is an analysis of over two-hundred thousand automatically detected HFO candidates in neocortical recordings from nine epilepsy and two control patients, originating in over 27,000 channel-hours of iEEG. The overall volume of data processed was significantly larger than any other studies. Analyzing multi-hour continuous recordings may permit more reliable estimates of global HFO rates across brain states. These estimates may be more reliable than, for example, a short (e.g., 10-minute) iEEG segment examined under the constraints of human processing. Larger data sets may produce more stable statistical estimates of the number of HFO classes.

The findings include an increase in ripple-like oscillations in the neocortical SOZ. The finding also include that fast ripple-like events are rare and not increased in the neocortical SOZ.

Events of all four classes in both control patients has been observed. Rates for control regions were not particularly large or small for any cluster when compared with seizure-subject NSOZ regions. With two control patients, the permutation tests had low power and these conclusions may be weak. They may be discouraging for the prospect of finding a universally "normal" rate of HFOs, which may serve as a baseline for patient-independent detection of the SOZ.

Microelectrodes may record HFOs of higher frequency than macroelectrodes on depth but not surface electrodes. There are cellular architectural differences between hippocampus, for example, and neocortex. This result may reflect genuine physiologic differences. Alternatively, surface microelectrodes may be non-penetrating and may rest atop the pia mater, which may act as a lowpass filter, while the depth microelectrodes may penetrate the parenchyma.

The data-mining approach used (as well as subsequent analyses) treats all iEEG equally. The methods used may not explicitly attempt to parse whether HFO detections are occurring ictally or interictally, or during specific states of arousal, or in conjunction with epileptiform, events such as sharp waves, or within or outside of lesions, for example. Interpreting the finding of an increase in cluster 4 event rates in SOZ may be done with suboptimal precision and the detections described herein may not provide certain information beyond that of potentially correlated phenomena. HFOs may provide localizing information independent from that of interictal spikes, lesions, and/or seizures themselves (and others for example).

This algorithmic naivete leads to certain conclusions of HFOs in epilepsy. For example, a signal was found that increases in the SOZ without special selection of patients, channels, or time-epochs for processing, which suggests that the signal is strong. It may also suggest that similar findings in studies of HFOs in mesial temporal lobe, which use restrictive data pre-selection criteria, may be more generalizable, and/or more practically useful in the clinical setting. These signals are able to be detected and/or classified automatically, without human intervention. It may portend increases in the efficiency and reliability with which presurgical evaluations may be done. It may also open a door to the possibility that HFOs may be used as control signals in closed-loop implantable seizure therapy devices, which may not have to pre-identify optimal data for processing. Such devices may offer hope to patients who are not surgical candidates.

Systems, methods, and apparatus are described herein for automatically detecting and/or classifying 100-500 Hz field potential oscillations in intracranial electroencephalographic records. In an example experiment, the algorithm implemented in such systems, methods, and apparatus was run on over 31,000 channel-hours of human iEEG, at data set orders of magnitude larger than those previously processed in the context of high-frequency oscillation analysis. The outputs of the machine executing the algorithm were compared with human performance on the HFO classification task. In this experiment, it was determined that the algorithm may be as proficient as human experts at labeling ground truth events. The algorithm was used to investigate HFOs in neocortical epilepsy patients, providing a systematic study in this patient population, and including a direct comparison with control patients having no history of seizures.

All four automatically identified classes of spontaneous neocortical HFOs in both epilepsy patients and controls were observed. No significant differences were found between the rate at which HFOs occurred in control neocortex and that in nonseizure-onset neocortex in epilepsy patients. One class of oscillations (median bandpassed spectral centroid ~140 Hz) corresponding to ripples was increased in rate in the seizure onset zone. This was demonstrated in an unselected data set without human intervention. A class of oscillations corresponding to fast ripples was rare in occurrence and, in contrast to findings from temporal lobe structures, showed no significant rate differences between non-seizure-onset and seizure-onset neocortices. Significant differences in neocortical surface HFO rates within and outside the SOZ were found only on macroelectrode recordings. None were found on microelectrode recordings. For depth electrodes, events detected by microelectrodes had stochastically higher peak frequencies than those detected by macroelectrodes, though this was not true for neocortical surface electrodes.

The systems, methods, and apparatus described herein may be integrated as a research tool into the clinical workflow for SOZ localization. For example, spatial maps of HFO rates, or other event rates for example, may be produced, such as the one shown in FIG. 19 for example. These spatial maps may be produced for each sensor device implanted in a patient, in a time frame sufficiently short for the data to inform the surgical decision, if desired.

Figure 19:
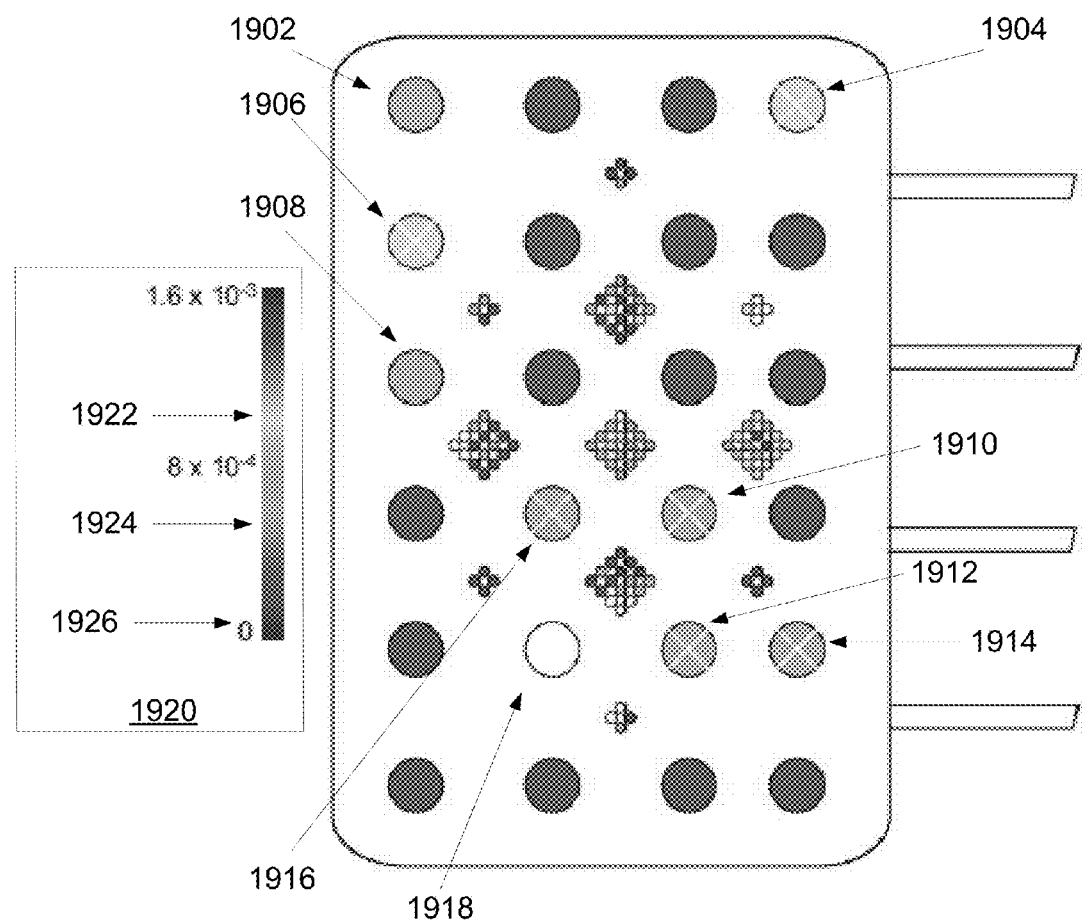
FIG. 19 illustrates spatial maps of HFO rates.

FIG. 19 illustrates a spatial HFO map for subject SZ 06, showing cluster 4 event rate (events/sec) at each channel on a hybrid 6×4 subdural grid. As illustrated in FIG. 19, each channel may correspond to an event rate indicated in the event rate legend 1920. In an example embodiment, the relationship between a given channel its corresponding event rate in the legend may be indicated by a similar color or other form of indication to a user for example. The channels indicated at 1902-1918 may each correspond to a different rate indicated in the event rate legend 1920. For example, channels 1904 and 1906 may correspond to the event rate indicated at 1922; channels 1902 and 1908-1916 may correspond to the event rate indicated at 1924; and the other channels indicated in the subdural grid (e.g., excluding channel 1918) may correspond to the event rate indicated at 1926. The subdural grid may also indicate channels for which tissue may be resected. For example, in FIG. 19, the white crosses, indicated at channels 1906, 1904, 1910, 1912, 1914, and 1916, mark macroeletrode channels for which underlying tissue may be surgically resected. Channel 1918 is an unfilled circle, which may indicate that there is no data available for this channel.

In an example embodiment, similar mapping displays, as the one illustrated in FIG. 19 for example, may be integrated with 3-D brain renderings to indicate the location of the rates on the brain. For example, the 3-D brain renderings may be generated from MRI images, or other imaging techniques for example. In another example embodiment, time-series images (e.g., in the form of movie or sequence of static images) of HFO-rate spatial maps may be produced for the user. In an example embodiment, the images described herein may be discrete maps indicating color in the regions bounded by the electrode perimeters. In another example embodiment, the images may be interpolated or otherwise smoothed to produce continuous images.

The embodiments described herein may be used to find a signal that increases in the neocortical SOZ in the absence of stringent data selection and other human processing. HFO rates may also be used to identify neocortical or non-neocortical SOZ. Observing an increase in the rate of (cluster 4) HFOs relative to a "baseline" NSOZ rate may strongly suggest that a channel is in the SOZ. Areas of secondary spread may be confounded with areas of seizure onset in making decisions about which brain areas to resect. One approach may be to visually identify channels of secondary spread and/or conduct analyses similar to those described herein, such as using three groups—secondary spread, SOZ, and NSOZ—instead of two, and substituting Kruskal-Wallis analysis of variance in place of Mann-Whitney U tests for example.

In using HFO rates as biomarkers for epileptogenic tissue, appropriate thresholds may be determined for declaring them abnormal. HFO rates were found both within and outside the SOZ to be highly variable among patients. While the sample size of control patients was small, HFO rates in these subjects were not extreme relative to those in seizure patient NSOZ regions, making the prospect of using controls to establish global baseline "normal" absolute HFO rates unlikely. The correlation of event rates between cluster pairs (e.g., where observations are made on patients) may be examined. If a high correlation is found between cluster 4 rates and those of another cluster, a differential (or ratio) may be used instead of absolute measurement to permit the establishment of a generic baseline.

As mentioned above, the increases detected in SOZ were with respect to patient-internal baseline NSOZ rates. Establishing these baselines was done using knowledge of which channels were flagged as SOZ (and, implicitly, NSOZ) by the clinician. It is possible that such knowledge may be similarly utilized in future automated attempts at prospectively identifying the SOZ. If clinicians may identify channels with high likelihood of being NSOZ, the parameters of a baseline distribution for NSOZ cluster 4 HFO rates may be learned, and SOZ channel identification may be treated in an outlier detection framework. This may be done by controlling for multiple comparisons. A nonparametric alternative may be to use permutation tests. Without prior information about an individual's baseline NSOZ rate distribution, identifying high-probability SOZ channels may be difficult. Monte-Carlo-type permutation may be implemented, for example, if constraints may be placed on the sample space using assumptions on estimates of the marginal probability of being an NSOZ channel, for example, or on the spatial structure of NSOZ or SOZ channels. Approaches that attempt to find extreme values (e.g., "unusually" high rates of HFOs) in the absence of any other information, may run the risk of missing a large number of SOZ channels in cases where they are relatively numerous.

An orthogonal approach to SOZ channel prediction using HFOs may be to learn a boundary separating NSOZ and SOZ channels in an HFO-derived feature space. Each channel in a training sample whose SOZ-NSOZ label is known may be summarized by a multivariate feature vector whose elements were, for example, median values of the features used in unsupervised classification. Cluster labels may be ignored, used to determine which events were included in calculating the feature medians, or built into the construction of the feature vector itself, such as by representing each channel by a 12-dimensional (4×3, where 4 is the number of features used in clustering and 3 is the number of non-artifact clusters) feature vector for example. Augmenting this vector by including the rates of cluster 4 events, and/or those of other clusters, may be a logical and fruitful extension. Any of a wide array of supervised learning algorithms (e.g., k-nearest neighbors, logistic regression, support vector machines, and/or others) may be used to learn an effective input-output mapping, that may be used to classify unseen channels as SOZ or NSOZ. This approach may permit a richer description of the relationship between HFOs and seizure generating areas than may be achieved by using the univariate measure of HFO rate alone. It may also rely on labeling of both the NSOZ and SOZ classes.

In stage 1 detection, a detection scheme and parameter set may be chosen that closely mirrors accepted approaches. Having accumulated evidence that cluster 4 events may be important, stage 1 may be tuned to detect this class with higher sensitivity and precision. Such tuning may be used to increase performance gains which may lead to improved SOZ localization. Shrinking the window for computing the per-segment RMS energy threshold may be a refinement of the stage 1 detector. Reasonable optimization criteria may be generated using the data presented herein in manipulating this parameter. Using a nonparametric thresholding approach may give some performance boost, though this may be at increased computational cost.

Redesigning the stage 1 detection scheme may be an alternative to making incremental improvements. With a large collection of cluster 4 exemplars available, matched-filter type approaches may be used. Another implementation may include using power law detectors. An example statistic, known to a person of ordinary skill in the art, may be used for detecting events, such as in HFO detection for example. This statistic may include the sum of magnitude-squared Discrete Fourier Transform (DFT) coefficients, each raised to a power that may be in the range of 2 to 3. Similar statistics, known to a person of ordinary skill in the art, may include colored Gaussian noise, which may eliminate the assumption of known noise power, block processing to mitigate the effects of potential background nonstationarity, and/or leverage the observation that rather than being completely unknown in structure, many transient signals tend to aggregate their energy in a band. These extensions may be implemented for the HFO detection application, where transient nonstationary signals with partially known structure but unknown duration, strength, and/or location, may be extracted from the physiologic "1/f" background. Wavelet, rather than Fourier decomposition, may be used to take advantage of the temporal concentration of transient signals. An approximation method may be used for setting thresholds for the statistics they present.

Both real-time HFO rate display, and/or real-time HFO-based SOZ identification may be performed using the embodiments described herein. The speed with which SOZ inferences, whether made by human or machine for example, may be updated may be directly tied to the frequency with which events occur. HFOs are rare, such as 3-10 per hour for example. The tracking and/or control of HFOs may be performed using implantable, and/or external, devices.

The embodiments described herein may be used to improve the understanding of HFO dynamics, such as the way rates change over time and/or the spatial trajectory of "hot" regions for example. The combination of temporally sparse occurrence and high inter-patient variability of HFOs implies that long iEEG records may need to be analyzed in large numbers of patients—volumes of data for which analysis by humans may be wholly untenable. The automated approach discussed herein may be implemented in such occurrences.

Provide below is a more a detailed description of some of the features described herein.

For example, a power ratio is a feature that may be implemented in the embodiments described herein. The power ratio may include a ratio such as (250-500 Hz)/(100-200 Hz) for example. The power ratio may be computed on the band-passed data; frequency domain input. The power ratio may include a ratio of estimated power in the "fast-ripple" band to that in the "ripple" band. If there are two distinct populations of HFOs whose respective energy is concentrated in these two bands, the distribution of data along this feature may be strongly bimodal. An example equation of the power ratio feature is provided below:

$$fi = \frac{\hat{P}[250,000]}{\hat{P}[100,200]} \quad (A.1)$$

where $$\hat{P}_{[a,b]} = \sum_{\{k \in Z | \zeta(a) \le k \le \zeta(b)\}} |M[k]|^2, \ (a < b) \in (0, F_s/2) \quad (A.2)$$

M[k] may be a multitaper power spectral density estimate. To lessen computational burden the modified periodogram estimate may be used.

$$M[k] = \sum_{n=0}^{N-1} w[n]\tilde{x}[n]e^{-j\frac{2w}{N}nk},$$

k∈{0, 1, . . . , N−1} with an N-point Discrete Fourier Transform (DFT). {w[n]} is the Hanning window of length L and {x̃[n]} is the detrended signal, obtained by subtracting the least squares fit of a line from the original length L signal, {x[n]}. The signal m[n]=w[n]x̃[n], n ∈ {0, 1, . . . , L−1} is padded with N−L zeros before computing the DFT. ζ(μ)=⌊0.5+NTu⌋, with T the sampling period, and ⌊•⌋ the "floor" operator, which as used in this context accomplishes rounding to the nearest integer. This may handle cases when a and b do not coincide precisely with the frequency values sampled by the DFT. Fs is the sampling frequency.

A spectral centroid is another feature that may be implemented in the embodiments described herein. The spectral centroid may be computed on the bandpassed data; frequency domain input. The spectral centroid may include the frequency corresponding to the "center of mass" of the spectrum. This feature may distinguish events whose energy is relatively concentrated in either the ripple or fast ripple sub-band alone from those with narrow components in both bands, with relatively broadband spectra, or with predominant energy in an intermediate band. An example equation of the spectral centroid feature is provided below:

$$f_2 = \frac{\sum_{k=0}^{N/2} \frac{k}{NT}|M[k]|^2}{\sum_{k=0}^{N/2} |M[k]|^2} \quad (A.3)$$

A spectral peak is another feature that may be implemented in the embodiments described herein. The spectral peak may be computed on the raw data; frequency domain input. The spectral peak may include a frequency corresponding to the peak of the estimated power spectral density. This feature may capture some differences in the spectral characteristics of the background signal upon which the detections are superimposed. An example equation for the spectral centroid feature is provided below:

$$f_3 = \frac{1}{NT} \arg\max_k |M[k]|^2, \ k \in \{0, 1, \cdots, N/2\} \quad (A.4)$$

Line-length is another feature that may be implemented in the embodiments described herein. The line-length may be computed on the raw data, after first-order backward differencing; time domain input. Detections may be detrended and energy normalized by dividing by their Euclidean length. As detections are of different durations, normalization may be performed by the signal length (i.e., number of samples). This measure may be included as it has proven broadly applicable in automatic EEG discrimination tasks, such as seizure and gamma oscillation detection. An example equation for the line-length is provided below:

$$f_4 = \frac{1}{L}\sum_{n=0}^{L-2} |x[n+1] - x[n]| \quad (A.5)$$

Three additional features that may be implemented in the embodiments described herein may include a global/average-local peak ratio feature, an entropy of the squared and normalized Teager Energy Vector feature, and/or a wavelet packet-based energy feature. Each of these three features may be implemented for their ability to separate a small training set of detections labeled as either "stereotypical artifact" or "other." A characteristic example of each group from this training set is shown in FIG. 20.

Figure 20:
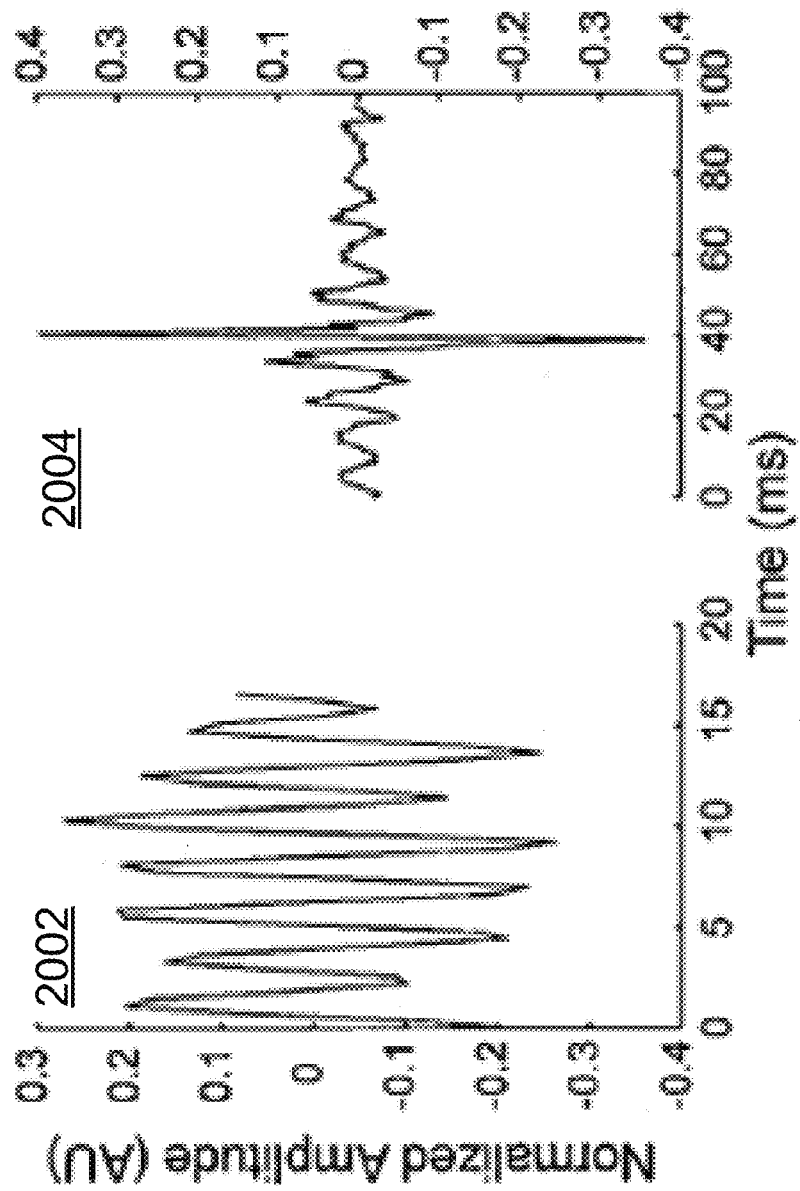
FIG. 20 illustrates 100-500 Hz bandpassed examples of human-labeled positive stereotypical artifact and negative stereotypical artifact classes.

FIG. 20 illustrates 100-500 Hz bandpassed examples of human-labeled positive stereotypical artifact, at graph 2002, and negative stereotypical artifact, at graph 2004, classes. The class in graph 2004 is a heterogeneous "other" category including all non-stereotypical artifacts and not as well represented by a single exemplar as the stereotypical artifact class. A small training sample (n=500) of randomly selected stage 1 detections from two patients (CT 01 and SZ 05) was labeled and three features were empirically chosen for their strong ability to distinguish these two classes. The three features are described below.

One feature is the global/average-local peak ratio feature. This feature may be computed on the bandpassed, data; time domain input. The global/average-local peak ratio feature may include a ratio of the global maximum value to the average of other local maxima (i.e., excluding the global maximum). Detections may be detrended and smoothed using a 3-point moving average filter. An example equation is provided below:

$$f_5 = \frac{g^*}{\frac{1}{J-1}\sum_{\{g_i \in G | g_i < g^*\}} g_i} \quad (A.6)$$

where G={$g_1$, . . . $g_J$} is the set of all local maxima and g*=max G.

Another feature is an entropy of the squared and normalized Teager Energy Vector feature. This feature may be computed on the bandpassed data; time domain input. Detections are detrended and energy normalized by dividing by their Euclidean length. For a signal composed of a single time-varying (or not) frequency and sampled at a sufficiently high rate, the Teager Energy sequence may have a value at any time that approximates, to within a constant, the energy required to "generate" the signal using a mechanical spring-and-mass analogy. It is given by:

$$T[n] = \begin{cases} x[n]^2 - x[n+1]x[n-1] & n = \{1, \ldots, L-2\} \\ 0 & \text{otherwise} \end{cases} \quad (A.7)$$

where a definition has been imposed by necessity at the endpoints. The signal is squared, making it everywhere positive, and normalize by its sum to make it a pseudo probability mass function before computing its entropy, so that:

$$S[n] = \hat{T}^2[n] = \frac{T^2[n]}{\sum_{n=0}^{L-1} T^2[n]}, n = \{0, \ldots, L-1\} \quad (A.8)$$

$$f_6 = -\sum_{n=0}^{L-1} S[n]\log_2 S[n] \quad (A.9)$$

Another feature that may be implemented in the embodiments described herein is a wavelet packet-based energy feature. This feature may be computed on the bandpassed data; time domain input. The signal is made even length, if necessary, by appending a single sample equal in value to the last sample (sample L-1). It is then made length-512 by either truncation or periodized extension on both sides, and energy-normalized by dividing by its Euclidean length. A 4-level wavelet packet decomposition using the wavelet packet system generated from the Daubechies $\phi_{D8}$ scaling function is performed.

For understanding the wavelet packet decomposition, a sufficient background may be given below to make the operational description of the wavelet packet-based energy feature understood to a person of ordinary skill in the art.

Any continuous-time signal $f(t) \in L^2(R)$ may be expressed using the expansion:

$$f(t) = \sum_{k=-\infty}^{\infty} c_{j_0}(k) 2^{j_0/2} \varphi(2^{j_0} t - k) + \sum_{k=-\infty}^{\infty} \sum_{j=j_0}^{\infty} d_j(k) 2^{j/2} \psi(2^j t - k) \quad (A.10)$$

where $j_0$ is an arbitrary initial scale and $\Phi(t)$, the basic scaling function, and $\phi(t)$, the mother wavelet, are non-unique functions that obey the following relations:

$$\varphi(t) = \sum_{n=-\infty}^{\infty} h_o(n)\sqrt{2}\,\varphi(2t-n), \ n \in Z \ \text{and} \quad (A.11)$$

$$\psi(t) = \sum_{n=-\infty}^{\infty} h_1(n)\sqrt{2}\,\varphi(2t-n), \ n \in Z \quad (A.12)$$

for some sequences $\{h_0(n)\}$ and $\{h_1(n)\}$. The scaling and wavelet coefficients (i.e., c's and d's, respectively) in (A.10) are called the discrete wavelet transform of f(t), and if the set of expansion functions forms an orthonormal basis (or tight frame), they may be computed as the inner products:

$$c_j(k) = \int_{-\infty}^{\infty} f(t) 2^{j/2} \phi(2^j t - k) dt \quad (A.13)$$

and $$d_j(k) = \int_{-\infty}^{\infty} f(t) 2^{j/2} \phi(2^j t - k) dt \quad (A.14)$$

In the case where the expansion set is a frame, a dual frame may be specified such that the inner products in (A.13) and (A.14) are identical after substituting the dual frame functions for their counterparts in the original expansion set.

In practice, the DWT coefficients may be computed without explicitly considering the functions in the expansion set, using Mallat's algorithm for example, which may achieve the signal decomposition by passing it through a filter bank. The discrete-time wavelet transform (DTWT) coefficients, which arise from an analogous decomposition of a sequence rather than a continuous-valued function, and are what may be calculated from sampled representations of signals stored in computers, are computed identically. The DWT/filter bank equivalence is not shown here, but rather simply state how the DWT (and DTWT) are implemented via filter banks, to illuminate the wavelet packet decomposition described below.

The scaling and wavelet coefficients at scale j−1 may be computed by passing the scaling coefficients at scale j through lowpass and highpass filters, respectively, followed by downsampling by a factor of 2. The impulse responses of the lowpass and highpass filters are the time-reversed recursion coefficients from (A.11), $\{h_0(-n)\}$, and from (A.12), $\{h_1(-n)\}$, respectively. At each stage, the wavelet coefficients may be "left behind" and the filter bank may be iterated on the scaling coefficients, yielding the set of scaling and wavelet coefficients for the next lower (i.e. coarser) scale. The filtering tree may continue down to scale $j=j_0$. For practical signals that are band-limited there may be an upper scale J above which the wavelet coefficients are negligible, and so by having as the initial input the fine scale coefficients $c_j$ (which may be approximated by the samples of the signal itself), the filter bank may yield an approximation to the full decomposition in (A.10).

If at each stage the filter bank is iterated on both the scaling and the wavelet coefficients, the resultant full binary tree is known as a wavelet packet decomposition. The effective expansion set analogous to that in (A.10) may be overcomplete, but viewed as a time-scale decomposition of the input signal, the procedure yields completely evenly spaced frequency (i.e. scale) resolution, in contrast to the logarithmic resolution of the DWT. The cost of this increase in resolution is increased computational complexity (O(N log(N)) rather than O(N)).

Considering as a "node" of the decomposition tree each sequence of coefficients that is the output of high- or lowpass filtering followed by downsampling of the signal at the parent node, then a 4-level tree may have a total of 31 nodes. For each of the 31 nodes in the binary decomposition tree, the ratio of the node's total energy may be computed to the cumulative energy of the nodes at the same level (for the top node, the input signal itself, this trivially equals 1). An energy vector, E, may be formed by concatenating these node relative energies, traversing the tree from top to bottom and left to right. The feature returned, $f_7$, may be the projection of this energy vector along a predetermined direction in 31-dimensional space, $V_1$, found via PCA on a training set comprised of a subset of detections from two patients with putative artifacts labeled. An energy vector may be formed for each detection using the method described above; the first principal component, $V_1$, may be found and stored for later use in computing $f_7$:

$$F7 = E^T V_1 \quad (A.15)$$

To ease the computational burden in the clustering stage, after forming the 7-dimensional feature vectors $\{F_1, \ldots, F_I\}$, where I is the total number of detections (anomalies) that pass through stage 2, $\{\hat{F}_1, \ldots, \hat{F}_I\}$ may be formed by projecting onto the first four principal components. This set of 4-dimensional feature vectors may be the input to the clustering algorithm described herein.

Described herein is a method for fully automated detection and/or classification of high frequency brain oscillations (HFOs; that may be described in this embodiment as transient signals (~5-100 ms) with high power in the 100-500 Hz range, but these concepts are easily extended to signals of higher/lower frequency, longer duration, different physiologic origin). One reason for detecting these oscillations may be their potential use in seizure localization and/or prediction.

Highly anomalous putative HFO events may be retained from a candidate set of hypersensitive but highly nonspecific initial detections. One example of the choice of time-window for defining the "local" background may be ~2.5 s. An example of the dimension of the space in which the background model is learned may be 2.

Putative HFOs may be clustered coming out of stage 2, of the algorithm described herein, in some feature space (which may be the raw data itself). A statistical method may be used, such as the gap statistic for example, to choose the optimal number of clusters automatically. The clustering of HFOs is not limited to the gap statistic or other methods described herein. Other methods may be used for clustering the HFOs coming out of stage 2 and/or deciding on a number of clusters, such as k-means, fuzzy c-means, decision trees, silhouette statistic, and/or other statistical methods for example.

The algorithm described herein may be used in an implantable system for facilitating localization of seizure onset channels, but may not be limited to such implementations. For example, the algorithm described herein may be used for detecting any known physiological condition. Any oscillatory signal may be detected that is a putative biomarker for some physiologic condition for example. The algorithm may be utilized in an offline mode and/or in real-time. The systems, methods, and apparatus described herein may be implemented in any physiological system that may generate oscillations (e.g., the heart, the brain, etc.). Several embodiments of the implantable system are described below. While embodiments described herein may be directed to determining one or more clusters of events indicative of a region of the brain, the described embodiments may be used to determine anomalous physiologic events indicative of other portions of the body as well.

In the implantable system, stages 1 and 2 of the algorithm described herein may proceed as described elsewhere herein. Stage 3 of the algorithm may be a supervised learning step. For example, a given candidate may be assigned, such as by using k-nearest-neighbors for example, to its most probable cluster (among those discovered utilizing the algorithm and data set described herein), and e.g. cluster 4 events, may be counted (or otherwise processed) and displayed for the clinician as an evolving "heat-map" of activity that that may be periodically updated. The clinician may integrate information gleaned from this imaging modality into the surgical decision making process.

Each channel may assign a probability of being located in the seizure onset zone based on pre-establishment of a patient-specific threshold, such as on the cluster 4 event rate (or other characteristic) for example. Baseline upon which threshold is based may be formed using channels strongly which may be distant from the seizure source.

Periodic re-tuning of the algorithm may be performed as new patient data may be acquired and/or new hypotheses arise about what features of HFOs are relevant for seizure localization and prediction. The feature set used as inputs to clustering and/or the number and nature of the clusters discovered and used for localization and/or prediction may change without changing embodiments described herein.

For the epilepsy application, preoperative offline learning of HFO clusters may be performed using the algorithm described herein. Subsequently, in the intraoperative setting, established clusters may be used in conjunction with nearest-neighbor type methods to generate a "heat map" superimposed upon a live brain image. The channels may be indicated by flashes different colors at different times in accordance with the spatiotemporal evolution of HFOs of different predetermined clusters for example. Doctors may associate patterns they see in this imaging modality with surgical outcomes, and use the information to perform more effective surgeries. Real-time online clustering and/or cluster updating may be performed using the embodiments described herein, and/or automated localization of the seizure focus based on clustering results for example.

Figure 21:
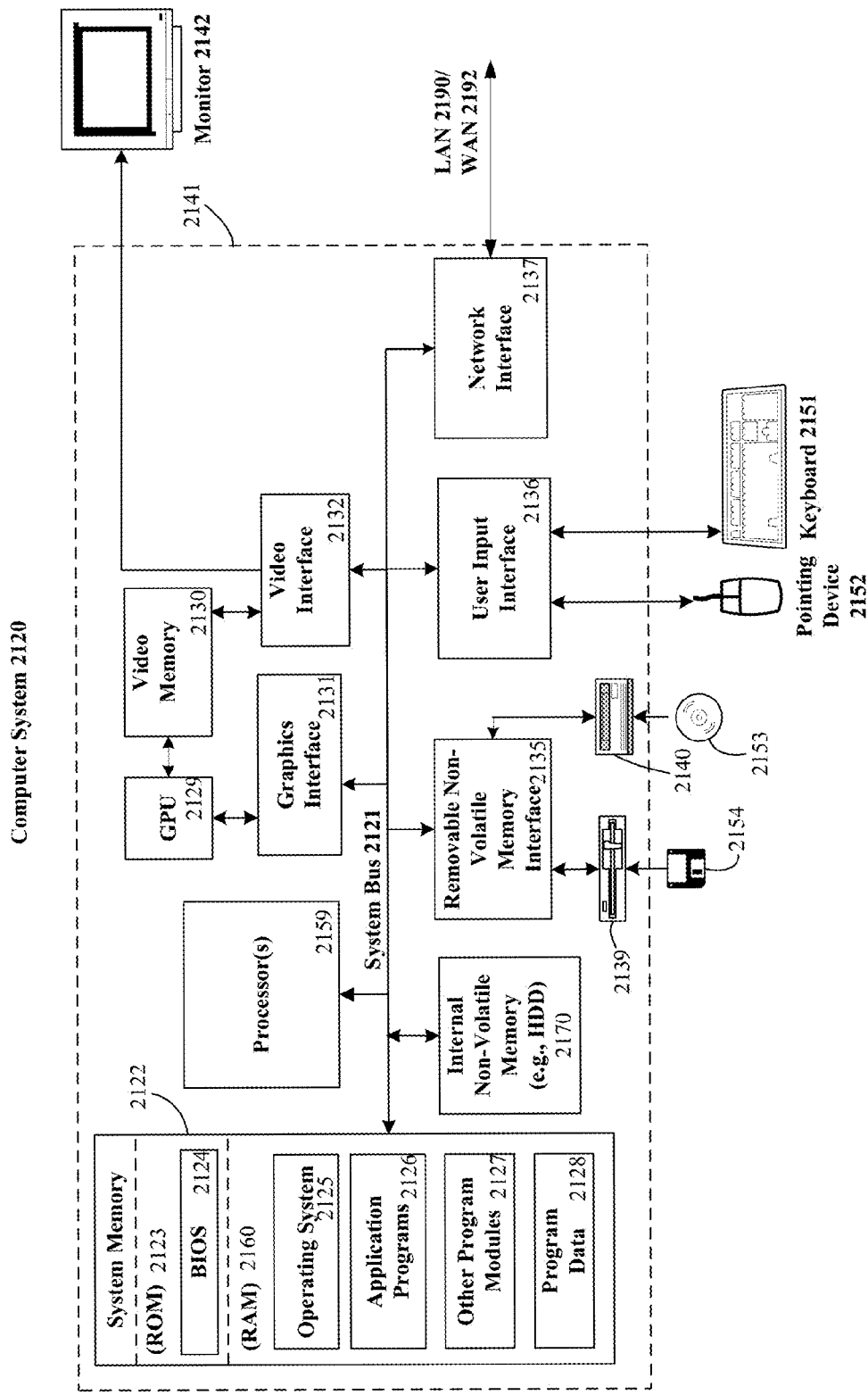
FIG. 21 is a block diagram of one embodiment of a computer system in which aspects of the disclosed systems and methods may be implemented.

FIG. 21 is a block diagram of an example computer system 2120 on which the embodiments described herein and/or various components thereof may be implemented. For example, the functions performed by the entities described in the various embodiments above may be performed by one or more such example computer systems. For example, the algorithm described herein may be implemented in software (i.e., computer executable instructions or program code) executing on one or more such computer systems 2120. It is understood, however, that the computer system 2120 is just one example of a suitable computing environment and is not intended to suggest any limitation as to the scope of use or functionality of the presently disclosed subject matter. For example, the embodiments described herein may be performed on an implantable device or system that is capable of being implanted in a patient. Neither should the computer system 2120 be interpreted as having any dependency or requirement relating to any one or combination of components illustrated in FIG. 21. In some embodiments, the various depicted computing elements may include modules or components configured to instantiate specific aspects of the present disclosure. For example, the terms "module" or "component" used in this description may include specialized hardware components configured to perform function(s) by firmware or switches. In other example embodiments, the terms "module" and "component" may include a general purpose processor, memory, etc., configured by software instructions that embody logic operable to perform function(s). In example embodiments where modules or components include a combination of hardware and software, an implementer may write source code embodying logic and the source code may be compiled into machine readable code that can be processed by the general purpose processor. Since the state of the art has evolved to a point where there is little difference between hardware, software, or a combination of hardware/software, the selection of hardware versus software to effectuate specific functions is a design choice left to an implementer. More specifically, a software process may be transformed into an equivalent hardware structure, and a hardware structure may itself be transformed into an equivalent software process. Thus, the selection of a hardware implementation versus a software implementation is one of design choice and left to the implementer.

In FIG. 21, the computer system 2120 comprises a computer 2141, which may include a variety of computer readable media. Computer readable media may be available media that may be accessed by computer 2141 and may include volatile and/or nonvolatile media, removable and/or non-removable media. The system memory 2122 may include computer storage media in the form of volatile and/or nonvolatile memory such as read only memory (ROM) 2123 and random access memory (RAM) 2160. A basic input/output system 2124 (BIOS), containing the basic routines that help to transfer information between elements within computer 2141, such as during start-up, may be stored in ROM 2123. RAM 2160 may contain data and/or program modules that are immediately accessible to and/or presently being operated on by processing unit 2159. By way of example, and not limitation, FIG. 21 illustrates operating system 2125, application programs 2126, other program modules 2127, and program data 2128. As a further example, detected signals and/or clustering information may be stored in the system memory 2122, as well as in any of a variety of non-volatile memory media discussed herein.

The computer 2141 may also include other removable/non-removable, volatile/nonvolatile computer storage media. By way of example, the computer 2141 may include a hard disk drive 2170 that reads from or writes to non-removable, non-volatile magnetic media, a magnetic disk drive 2139 that reads from or writes to a removable, nonvolatile magnetic disk 2154, and an optical disk drive 2140 that reads from or writes to a removable, nonvolatile optical disk 2153 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. Magnetic disk drive 2139 and optical disk drive 2140 may be connected to the system bus 2121 by a removable memory interface, such as interface 2135. The drives and their associated computer storage media discussed herein, and illustrated in FIG. 21, may provide storage of computer readable instructions, data structures, program modules and other data for the computer 2141.

A user may enter commands and information into the computer 2141 through input devices such as a keyboard 2151 and/or pointing device 2152, commonly referred to as a mouse, trackball, or touch pad. Other input devices (not shown) may include a microphone, joystick, game pad, satellite dish, scanner, sensors (e.g., remote sensing device), a high sensitivity, low specificity detector, or the like. These and other input devices may be connected to the processing unit 2159 through a user input interface 2136 that is coupled to the system bus, but may be connected by other interface and/or bus structures, such as a parallel port, game port, or a universal serial bus (USB) for example. The computer may connect to a local area network or wide area network, such as LAN 2190 and/or WAN 2192, through a network interface or adapter 2137.

As is apparent from the embodiments described herein, all or portions of the various systems, methods, and aspects of the present invention may be embodied in hardware, software, or a combination of both. When embodied in software, the methods and apparatus of the present invention, or certain aspects or portions thereof, may be embodied in the form of program code (i.e., computer executable instructions). This program code may be stored on a computer-readable storage medium, such as a magnetic, electrical, or optical storage medium, including without limitation a floppy diskette, CD-ROM, CD-RW, DVD-ROM, DVD-RAM, magnetic tape, flash memory, hard disk drive, or any other machine-readable storage medium, wherein, when the program code is loaded into and executed by a machine, such as a computer or server, the machine becomes an apparatus for practicing the described embodiments. A computer on which the program code executes may include a processor, a storage medium readable by the processor (including volatile and/or non-volatile memory and/or storage elements), at least one input device, and/or at least one output device. The program code may be implemented in a high level procedural or object oriented programming language. Alternatively, the program code may be implemented in an assembly or machine language. In any case, the language may be a compiled or interpreted language. When implemented on a general-purpose processor, the program code may combine with the processor to provide a unique apparatus that operates analogously to specific logic circuits. As used herein, the terms "computer-readable medium" and "computer-readable storage medium" do not include a signal.

Changes may be made to the embodiments described above without departing from the broad inventive concepts thereof. For example, the frequency ranges provided herein are approximate and embodiments herein are not materially changed if the frequency ranges are slightly, or even dramatically, different. Additionally, while embodiments described may include the use of neocortical or non-neocortical oscillations (e.g., brain oscillations), the described embodiments may include the use of neocortical and/or non-neocortical oscillations. Accordingly, the present invention is not limited to the particular embodiments disclosed, but is intended to cover all modifications that are within the spirit and scope of the invention as defined by the appended claims.

What is claimed:

1. A method for automatically detecting, classifying, and processing oscillatory signals for use as a biomarker for a physiologic physiological event in a patient, the method comprising:
   detecting and classifying oscillatory signals representative of discrete physiologic events in a patient's body using a high sensitivity, low specificity detector;
   processing, using a processor, the detected signals by:
      testing the detected signals in the context of surrounding background activity to identify anomalous discrete physiologic events that are sufficiently different from the surrounding background activity; and
      automatically clustering said anomalous discrete physiologic events into clusters of anomalous physiologic events having correlative morphological, time, or location characteristics;
   determining at least one cluster of anomalous physiologic events as a biomarker indicative of at least one region of the patient's body that is associated with a medical condition; and
   providing treatment, using a treatment device responsive to said biomarker, of said medical condition to the at least one region of the patient's body identified by said biomarker.

2. The method of claim 1, wherein the discrete physiologic events are associated with the patient's brain, wherein the at least one region of the patient's body comprises at least one region of the brain, and wherein the medical condition comprises epileptic seizure.

3. The method of claim 2, comprising the further steps of implanting said high sensitivity, low specificity detector in the patient's body and processing outputs of said high sensitivity, low specificity detector to localize seizure onset channels of said patient.

4. The method of claim 1, wherein each discrete physiologic event is a high frequency oscillation event.

5. The method of claim 4, wherein each discrete physiologic event is detected by bandpass filtering and thresholding electroencephalographic recordings in at least one of a time domain, a frequency domain, or a domain of another set of applicable basis functions.

6. The method of claim 5, comprising the further step of determining a power ratio in the frequency domain by estimating power in a fast ripple band to that in a ripple band.

7. The method of claim 5, comprising the further step of determining a spectral centroid in the frequency domain by distinguishing physiologic events having energy concentrated in a ripple sub-band or a fast ripple sub-band alone from those with components in the ripple and fast ripple band, with relatively broadband spectra, or with predominant energy in an intermediate band.

8. The method of claim 5, comprising the further step of determining a line length in the time domain by detrending and normalizing detections.

9. The method of claim 5, comprising the further step of determining a spectral peak in the frequency domain by identifying a frequency corresponding to a peak of an estimated power spectral density.

10. The method of claim 5, comprising the further step of determining a global/average local peak ratio in the time domain, wherein the global/average local peak ratio comprises a ratio of a global maximum value to an average of other local maxima.

11. The method of claim 5, comprising the further step of determining an entropy of a Teager Energy vector in the time domain by computing a value of a Teager Energy sequence that approximates the energy used to generate a signal.

12. The method of claim 5, comprising the further step of determining a wavelet packet decomposition in the time domain by performing a 4-level wavelet packet decomposition.

13. The method of claim 1, wherein each discrete physiologic event comprises an artifact, a physiologic event unrelated to seizure localization, or a physiologic event related to seizure localization.

14. The method of claim 1, comprising the further steps of creating or selecting templates of clusters of anomalous physiologic events representative of the discrete physiologic events, and comparing detected physiologic events or clusters to said templates to identify the discrete physiologic events represented by the detected physiologic events or clusters.

15. The method of claim 1, further comprising recording a time at which each anomalous physiologic event occurs.

16. The method of claim 1, wherein the processing step is performed by a processor programmed to implement the testing and clustering steps.

17. The method of claim 16, wherein the determining step is performed by said processor.

18. The method of claim 16, comprising the further step of generating a spatial map of an event rate of the signals representative of the discrete physiologic events.

19. The method of claim 18, wherein the spatial map comprises a time-evolving heat map in the form of a movie or a sequence of static images.

20. A system for automatically detecting, classifying, and processing oscillatory signals for use as a biomarker for a physiologic event in a patient, the system comprising:
at least one high sensitivity, low specificity detector configured to detect and classify oscillatory signals representative of discrete physiologic events in a patient's body;
a processor configured to:
test the detected signals in the context of surrounding background activity to identify anomalous discrete physiologic events that are sufficiently different from the surrounding background activity;
automatically cluster said anomalous discrete physiologic events into clusters of anomalous physiologic events having correlative morphological, time, or location characteristics; and
determine at least one cluster of anomalous physiologic events as a biomarker indicative of at least one region of the patient's body that is associated with a medical condition; and
a treatment device responsive to said biomarker that is adapted to provide therapy for said medical condition to the at least one region of the patient's body identified by said biomarker.

21. The system of claim 20, wherein each discrete physiologic event is a high frequency oscillation event.

22. The system of claim 21, wherein the processor is further configured to identify each discrete physiologic event by bandpass filtering and thresholding electroencephalographic brain recordings of the patient in at least one of a time domain, a frequency domain, or a domain of another set of applicable basis functions.

23. The system of claim 20, wherein each discrete physiologic event comprises an artifact, a physiologic event unrelated to seizure localization, or a physiologic event related to seizure localization.

24. The system of claim 20, wherein the processor is further configured to create or select templates of clusters of anomalous physiologic events representative of discrete physiologic events, and compare detected physiologic events or clusters to said templates to identify discrete physiologic events represented by the detected physiologic events or clusters.

25. The system of claim 20, the system being configured for implementation in a patient and wherein the processor is further configured to localize seizure onset channels of said patient.

26. The system of claim 20, wherein the processor is further configured to generate a spatial map of an event rate or other descriptive statistic for the signals representative of the discrete physiologic events.

27. The system of claim 26, wherein the spatial map comprises a time-evolving heat map.

28. The system of claim 20, wherein the processor is further configured to assign each signal a probability of being located in a seizure onset zone based on pre-establishment of a patient-specific threshold.

* * * * *